(12) United States Patent
Studdert et al.

(10) Patent No.: US 6,171,592 B1
(45) Date of Patent: Jan. 9, 2001

(54) EQUINE RHINOVIRUS 1 PROTEINS

(75) Inventors: Michael J. Studdert; Brendan S. Crabb, both of Parkville (AU); Li Feng, Pittsburgh, PA (US)

(73) Assignee: The University of Melbourne, Parkville (AU)

( * ) Notice: Under 35 U.S.C. 154(b), the term of this patent shall be extended for 0 days.

(21) Appl. No.: 09/091,219

(22) PCT Filed: Dec. 18, 1996

(86) PCT No.: PCT/AU96/00815

§ 371 Date: Oct. 5, 1998

§ 102(e) Date: Oct. 5, 1998

(87) PCT Pub. No.: WO97/22701

PCT Pub. Date: Jun. 26, 1997

(30) Foreign Application Priority Data

Dec. 18, 1995 (AU) .................................................. PN7201

(51) Int. Cl.[7] ........................... A61K 39/12; A61K 38/00
(52) U.S. Cl. ................................... 424/186.1; 424/204.1; 530/300; 530/324; 536/23.72; 930/220
(58) Field of Search ............................. 424/186.1, 204.1; 530/300, 324; 536/23.72; 930/220

(56) References Cited

PUBLICATIONS

Forss et al. Nucleic Acid Research, 1984, vol. 12, No. 16, pp. 6587–6601, 1984.*
Ditchfield et al., "The properties and Classifications of Two New Rhinoviruses Recovered from Horses in Toronto, Canada", pp. 181–189, (1965).
Li et al., "Equine Rhinovirus 1 is More Closely Related to Foot–And–Mouth Disease Virus Than to Other Picornaviruses", *Proc. Natl. Acad. Sci.*, vol. 93:990–995, (1996).
Wutz et al., Equine Rhinovirus Serotypes 1 and 2: Relationship to Each Other and to Aphthoviruses and Cardioviruses, *Journal of General Virology*, vol. 77:1719–1730, (1996).

* cited by examiner

*Primary Examiner*—Ali Salimi
(74) *Attorney, Agent, or Firm*—Foley & Lardner

(57) ABSTRACT

Equine rhinovirus 1 (ERhV1) is a respiratory pathogen of horses which has an uncertain taxonomic status. The nucleotide sequence of the ERhV1 genome and amino acid sequence have been substantially determined (FIG. 2). The predicted polyprotein was encoded by 6,741 nucleotides and possessed a typical picornavirus proteolytic cleavage pattern, including a leader polypeptide. The genomic structure and predicted amino acid sequence of ERhV1 were more similar to those of foot-and-mouth disease viruses (FMDV), the only members of the aphthovirus genus, than other picornaviruses. Nucleotide sequences coding for the complete polyprotein, the polymerase, and VP1 were analyzed separately. The phylogenetic trees confirmed that ERhV1 was more closely related to aphthoviruses than to other picornaviruses. Virion proteins and virus-like particles are described and probes, primers, antigens, vectors, diagnostics and tests developed.

10 Claims, 27 Drawing Sheets

FIG. 2A-1

Figure 1A:
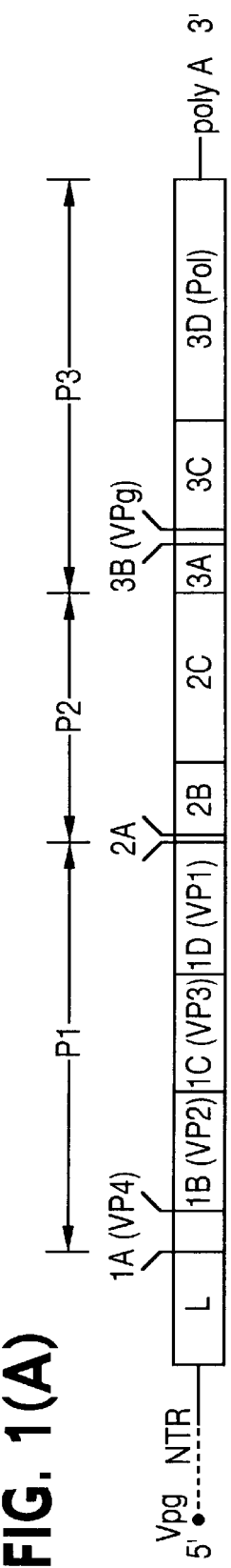

CCGTCAAGCCCGTTGCCTGTATAGCCAGGTAACCGGACAGCGGCTTGCTGGATTTTCCCG
   -430                    -410                  -390

ACACGCCTGTGGTAGCGCTGCCCAAAAGGGAGCGGAACTCCCCGCCGAGGCGGTCCTCTC
   -310                    -290                  -270

TGAAGTGGAGTGAGCGGATCTCCAATTTGGTCTGTTCTGAACTACACCATTTACTGCTGT
   -190                    -170                  -150

ACCGGCGCAGGGTCAAAAATTGTCTAAGCAGCAGCAGGAACGCGGGAGCG<u>TTTCTTTTCC</u>
   -70                     -50                   -30

A  G  A  V  R  M  M  D  K  F  L  Q  K  R  T  V  F  V  P  H
GCAGGTGCCGTTCGC<u>ATGATG</u>GACAAATTCTTGCAAAAGAGAACTGTTTTTGTCCCCCAT
       50                   70                    90

A  L  T  Q  L  T  Q  I  L  G  I  R  L  F  D  E  H  F  G  N
GCCTTGACACAACTGACACAGATTCTTGGAATTCGGCTTTTTGATGAACACTTCGGCAAT
      170                  190                  210

L  K  S  G  A  P  P  L  V  V  V  Y  K  L  W  Q  H  G  H  L
CTAAAATCAGGAGCACCGCCACTCGTGGTGGTGTACAAACTGTGGCAACATGGACACTTG
      290                  310                  330

L  S  D  F  W  A  C  V  S  A  K  P  G  H  A  V  F  Y  L  L
CTTTCTGATTTCTGGGCCTGTGTTTCGGCAAAACCGGGACATGCAGTATTCTACCTTCTC
      410                  430                  450

E  D  V  L  V  F  A  P  Y  D  F  E  S  L  G  K  D  P  P  K
GAGGATGTACTTGTTTTTGCGCCCTATGACTTTGAGTCACTGGGCAAGGACCCACCAAAG
      530                  550                  570

T  G  N  Q  N  M  S  G  N  S  G  S  I  V  Q  N  F  Y  M  Q
ACTGGCAACCAAAACATGTCCGGAAACAGTGGTTCAATTGTTCAAAATTTTTACATGCAA
      650                  670                  690

FIG. 2A-2

```
         GTGCCATTGCTCTGGATGGTGTCACCAAGCTGACAAATGCGGAGTGAACCTCACAAAGCG
             -370              -350              -330

TGGCCAAAAGCCCAGCGTTGATAGCGCCTTTTGGGATGCAGGAACCCCACCTGCCAGGTG
             -250              -230              -210

GAAGAATGCCCTGGAGGCAAGCTGGTTACAGCCCTGACCAGGCCCTGCCCGTGACTCTCG
             -130              -110               -90
                            L
                   M  A  A  S  K  V  Y  R  V  C  E  Q  T  L  L
         TTTTGTACTGACATGATGGCGGCGTCTAAGGTGTATAGAGTTTGCGAGCAGACTCTGCTG
             -10               10                30

L  D  K  T  I  R  L  T  G  L  H  N  Y  D  N  T  C  W  L  N
         CTTGACAAAACAATTCGTTTGACTGGACTCCACAATTATGACAATACTTGCTGGTTGAAT
             110               130               150

R  G  L  F  T  R  K  T  I  D  W  V  S  D  Q  T  G  I  K  D
         AGAGGTCTGTTCACTCGGAAAACAATTGATTGGGTGAGTGACCAGACTGGTATAAAAGAT
             230               250               270

D  V  G  T  M  E  K  P  R  S  I  T  L  W  S  G  P  K  V  C
         GATGTCGGTACGATGGAGAAACCCCGGTCGATTACTCTATGGTCTGGCCCCAAAGTGTGT
             350               370               390

T  S  E  G  W  I  C  V  D  D  K  K  I  Y  P  E  T  P  K  T
         ACAAGCGAGGGTTGGATCTGTGTTGATGACAAGAAAATATACCCAGAAACACCCAAAACA
             470               490               510
                                              L ↓ VP4
          L  H  Q  R  Y  E  K  A  F  E  L  S  G  G  G  T  S  T  P  T
         CTACACCAGAGATATGAAAAAGCATTTGAGCTCAGTGGCGGAGGTACATCCACTCCAACA
             590               610               630

Q  Y  Q  N  S  I  D  A  D  L  G  D  N  V  I  S  P  E  G  Q
         CAGTACCAGAATTCAATTGACGCAGACCTGGGAGACAATGTGATTAGCCCTGAAGGCCAG
             710               730               750
```

FIG. 2B-1

```
      G  S  N  T  S  S  T  S  S  S  Q  S  S  G  L  G  G  W  F
      GGCAGCAACACTAGTAGTTCAACCTCATCAAGCCAATCCTCTGGCTTGGGCGGGTGGTTC
      770                      790                      810

N  I  E  D  R  I  E  T  T  V  V  G  V  T  I  I  N  S  Q  G
      AACATTGAAGACAGAATTGAAACAACAGTGGTTGGAGTCACTATTATTAATTCACAAGGA
      830              850              870              890

D  P  V  T  R  L  G  P  T  L  S  R  H  Y  T  F  K  V  G  E
      GACCCAGTTACCAGACTTGGACCCACGCTTTCCAGGCACTACACATTTAAGGTAGGTGAG
      910              930              950              970

K  K  M  G  S  F  H  E  V  V  K  A  H  H  L  V  K  N  G  W
      AAGAAGATGGGCAGTTTTCATGAGGTTGTCAAAGCCCACCACCTGGTCAAGAACGGCTGG
      990              1010             1030             1050

V  P  E  Y  E  H  T  H  E  K  A  L  K  W  S  E  L  E  E  P
      GTGCCGGAGTACGAACACACACATGAGAAAGCACTCAAGTGGTCTGAGCTTGAGGAACCA
      1070             1090             1110             1130

S  S  V  H  L  V  M  P  Y  I  G  P  G  Q  P  T  N  L  T  L
      TCATCAGTGCATTTGGTGATGCCCTACATTGGGCCAGGCCAACAAATCTGACTTTG
      1150             1170             1190             1210

V  P  V  T  M  S  V  A  P  I  D  A  M  V  N  G  P  L  P  N
      GTGCCTGTGACCATGTCGGTGGCTCCCATGCGATGCAATGGTTAATGGGCCTCTTCCAAAT
      1230             1250             1270             1290

P  D  N  S  T  P  L  Y  P  K  V  V  V  P  P  R  Q  V  P  G
      CCTGATAATTCGACTCCACTATACCCCAAGGTTGTGGTCCCACCGCGCCAAGTTCCTGGC
      1310             1330             1350             1370
```

FIG. 2B-2

```
          S  S  L  L  N  L  G  T  K  L  L  A  D  K  K  T  E  E  T  T
          TCTAGTTGCTGAACCTTGGAACAAACTACTGGCTGACAAGAAGACAAGAGAGACTACA
                      830              850              870
                                       VP4 ↓ VP2

S  V  G  T  T  Y  C  Y  S  K  P  D  G  R  P  P  S  T  V  S
          TCTGTTGGAACAACCTACTGTTACTCCAAACCGGATGGTAGACCACCATCCACAGTGTCA
                      950              970              990

W  P  H  S  Q  S  H  G  H  A  W  I  C  P  L  P  G  D  K  L
          TGGCCCCATTCTCAATCACACATGGTCACGCATGGGATCTGTCCGTTGCCAGGTGACAAACTC
                     1070             1090             1110

D  V  V  V  Q  V  N  P  S  F  A  H  S  G  P  L  C  V  A  A
          GATGTGGTTGTGCAGGTGAATCCCTCATTTGCTCACTCCGGGCCGCTGTGTGTAGCAGCA
                     1190             1210             1230

A  Y  T  Y  Q  Q  L  S  V  F  P  H  Q  L  L  N  L  R  T  N
          GCTTACACATACCAACAACTTTCAGTTTTTCCCCACCAGTTGCTAAATTTGAGGACAAAT
                     1310             1330             1350

H  N  P  W  T  I  V  I  L  I  L  S  E  L  T  G  P  G  Q  T
          CACAACCCGTGGACCATTGTTATTTTAATTTTGTCTGAATTGACAGGACCTGGCCAAACT
                     1430             1450             1470
          VP2 ↓ VP3
          P  E  A  P  I  R  V  V  S  V  P  E  S  D  S  F  M  S  S  V
          CCAGAGGCACCGATTAGAGTGGTCTGTGCCTGAATCAGATTCTTTTATGTCTTCAGTA
                     1550             1570             1590

R  F  T  N  F  I  D  V  A  K  Q  T  Y  S  F  C  S  I  S  G
          CGGTTTACAAATTTCATTGATGTGGCAAAACAGACATATTCATTTTGTTCCATTTCTGGA
                     1670             1690             1710
```

FIG. 2C-1

```
  K   P   Y   F   E   V   T   N   T   S   G   D   E   P   L   F   Q   M   D   V
AAACCTTATTTTGAGGTTACCAACACCTCTGGGGACGAGCCACTGTTTCAGATGGATGTG
         1730                1750                1770

Q   Y   R   G   S   L   N   F   N   F   I   F   T   G   A   A   A   T   K   A
CAGTACAGAGGCTCACTTAATTTCAACTTTATTTTCACTGGTGCAGCAGCCACTAAGGCA
         1850                1870                1890

M   A   C   I   H   A   V   W   D   V   G   L   N   S   A   F   S   F   N   V
ATGGCGTGCATCCATGCCGTGTGGGATGTTGGCCTTGAACTCAGCTTTTCTTTTAATGTA
         1970                1990                2010

V   S   G   W   L   Q   V   Y   A   L   T   A   L   T   S   T   D   I   A   V
GTCTCTGGATGGCTTCAAGTTTATGCACTAACAGCTCTAACTTCAACTGACATTGCCGTG
         2090         2110↓                    2130
                      VP3  VP1
  P   A   D   L   P   D   K   Q   V   T   N   V   G   E   D   G   E   P   G   E
CCGGCGGACCTGCCCGACAAGCAGGTTACCAATGTGGGAGAGGATGGTGAACCCGGTGAG
         2210                2230                2250

L   L   D   R   F   F   F   D   V   E   T   L   E   L   S   N   L   T   G   S   P
TTGCTTGACCGGTTCTTTGATGTTGAGACACTTGAGCTTTCAAATTTGACAGGTTCTCCT
         2330                2350                2370

N   T   C   T   Y   F   F   S   D   L   E   L   S   I   Q   F   K   F   T   T
AACACTTGCACCTACTTCTTTTCTGATTTGGAATTGTCAATCCAGTTTAAATTTACCACC
         2450                2470                2490
```

FIG. 2C-2

```
  S  L  S  A  A  E  L  H  G  T  Y  V  A  S  L  S  S  F  F  A
TCGCTCAGTGCGGCAGAGCTACATGGCACTTACGTAGTAGCTAGTTTGTCATCATTTTTGCA
                             1790                    1810                    1830

K  F  L  V  A  F  V  P  P  H  S  A  A  P  K  T  R  D  E  A
AAGTTTCTGGTTGCCTTTGTGCCTCCCCACAGTGCAGCCCCAAAACGCGCGATGAAGCA
                             1910                    1930                    1950

P  Y  P  S  P  A  D  F  M  A  V  Y  S  A  E  R  T  V  V  N
CCTTATCCCTCCCCTGCTGACTTCATGGCCGTTTATTCTGCGGAACGGACGGTTGTGAAT
                             2030                    2050                    2070

N  S  K  G  R  V  L  V  A  V  S  A  G  P  D  F  S  L  R  H
AACAGTAAAGGCCGTGTGCTGGTTGCTGTTTCCGCCGGCCCAGACTTCTCCCTTCGTCAC
                             2150                    2170                    2190

T  E  P  R  H  A  L  S  P  V  D  M  H  V  H  T  D  V  S  F
ACAGAGCCTCGTCATGCTTTGTCACCCGTGGACATGCACGTGCACACAGATGTCAGTTTC
                             2270                    2290                    2310

A  T  H  V  L  D  P  F  G  S  T  A  Q  L  A  W  A  R  L  L
GCCACACATGTTCTGGATCCGTTTGGCTCGACTGCCCAACTGGCTTGGGCACGTCTGCTA
                             2390                    2410                    2430

T  P  S  S  V  G  E  G  F  V  W  V  K  W  L  P  V  G  A  P
ACTCCGTCCTCTGTTGGAGAGGGCTTTGTGTGGGTGAAGTGGCTCCCTGTTGGAGCACCA
                             2510                    2530                    2550
```

FIG. 2D-I

```
      T  K  T  T  D  A  W  Q  L  E  G  G  G  N  S  V  R  I  Q  K
      ACCAAGACCACAGATGCTTGGCAGTTAGAAGGAGGTGGAAATTCAGTAGAATTCAAAAA
              2570                     2590                  2610

A  C  A  S  A  L  P  Y  T  S  M  W  R  V  V  P  V  F  Y  N
      GCCTGTGCTTCAGCGTTGCCATATACATCAATGTGGCTGTGTGCCAGTCTTTTACAAT
              2690                      2710                 2730

G  S  I  L  L  T  S  D  A  H  D  K  G  G  C  Y  L  R  Y  A
      GGTTCCATCTTGCTGACTTCTGATGCGCATGATAAGGAGGTGCTACTTGCGGTATGCT
              2810                     2830                  2850
                                                           VP1 ↓ 2A
      D  K  T  R  H  K  F  P  T  N  I  N  K  Q  C  T  N  Y  S  L
      GACAAAACCAGACATAAATTCCCACTAACATCAACAACAGTGTACTAATTACTCTCTC
              2930                     2950                  2970

A  D  L  N  A  L  S  T  S  L  G  E  L  T  G  M  L  K  D  L
      GCAGACCTGAATGCCTTGTCAACGTCGCTAGGTGAATTGACTGGCATGCTAAAAGATCTT
              3050                     3070                  3090

A  T  L  A  V  A  A  M  R  T  K  D  P  V  V  V  M  L  I
      GCAACACTAGCTGTGGCAGCTATGAGGACAAAGGACCCAGTAGTGGTTATGTTGATT
              3170                     3190                  3210

L  Q  P  Y  M  K  T  I  P  G  K  I  S  D  L  V  T  D  A  A
      TTGCAGCCTTATATGAAAACTATTCCTGGTAAGATTTCTGATTTGGTCACTGATGCGGCT
              3290                    3310                   3330
                                    2B ↓ 2C
      P  E  G  V  V  E  K  Q  V  S  L  R  T  V  N  D  I  F  A  L
      CCTGAAGGAGTGGTTGAGAAGCAGGTGTCTCTTCGGACACTGAATGACATATTTGCTTTG
              3410                     3430                  3450
```

FIG. 2D-2

```
     L   A   V   A   G   M   C   P   T   V   V   F   K   I   A   G   S   R   S   Q
     TTGGCCGTTGCAGGAATGTGCCCCACTGTTGTGTTCAAGATTGCAGGCTCCCGTTCACAA
                              2650                    2670

G   W   G   A   P   T   K   E   K   A   T   Y   N   W   L   P   G   A   H   F
     GGCTGGGGTGCACCTACCAAAGAAAAGGCAACCTACAATTGGCTTCCTGGTGCACACTTT
              2750                    2770                    2790

F   R   A   P   A   M   Y   C   P   R   P   I   P   P   A   F   T   R   P   A
     TTCCGCGCCCCAGCGATGTATTGCCCTCGACCCATTCCGCCGGCTTTTACGCGTCCAGCG
              2870                    2890              2910
                                                 2A ↓ 2B
     L   K   L   A   G   D   V   E   S   N   P   G   P   T   I   F   S   K   A   S
     CTCAAATTGGCTGGAGATGTTGAGAGCAACCCTGGCCCCACTATTTTTCCAAAGCATCA
              2990                    3010                    3030

K   A   K   A   E   T   Y   S   P   F   Y   K   M   A   K   M   L   F   K   L
     AAAGCCAAGGCAGAGAAACTTATTCCCCGTTTTACAAAATGGCCAAAATGCTTTTCAAACTT
              3110                    3130                    3150

A   D   F   G   L   E   V   F   D   T   G   F   F   F   S   Y   F   Q   E   K
     GCTGATTTCGGATTGGAGGTCTTTGACACTGGGTTTTTTCTTTTCCTACTTTCAAGAGAAG
              3230                    3250                    3270

T   A   A   A   Q   I   P   K   G   V   Y   S   F   V   S   S   F   F   E   T
     ACGGCTGCCGCCCAAATTCCCAAAGGAGTGTATTCTTTTGTGTCGTCATTTTTCGAAACG
              3350                    3370                    3390

L   K   N   S   D   W   F   I   K   T   L   V   A   L   K   K   W   L   T   S
     CTTAAAAATTCTGATTGGTTCATAAAGACTCTTGTTGCCCTCAAGAAATGGCTGACATCC
              3470                    3490                    3510
```

FIG. 2E-1

```
     W  F  A  Q  E  Q  Q  A  D  D  D  A  L  Y  S  E  L  E  K  Y  P
     TGGTTTGCTCAAGAACAACAGGCAGATGATGCGCTCTATTCAGAATTGGAAAAATATCCC
        3530                   3550                   3570

D  M  Q  Q  R  A  L  A  V  R  D  K  G  L  F  S  L  L  Q  I
     GACATGCAGCAGCGTGCTCTCGCTGTGAAGGACAAAGGTCTCTTTTCCCTCCTGCAAATT
        3650                   3670                   3690

S  G  Q  G  K  S  Y  L  A  N  L  M  A  Q  A  I  S  L  L  L
     TCAGGGCAAGGCAAATCTTATTTGGCAAATCTGATGGCTCAAGCAATTTCGCTTCTCTTG
        3770                   3790                   3810

N  G  Q  A  V  V  I  M  D  A  L  G  Q  D  P  N  G  A  D  F
     AACGGACAGGCTGTGGTGATTATGGATGCATTGGGCCAGGATCCGAATGGTGCTGACTTT
        3890                   3910                   3930

D  K  G  I  P  F  T  S  P  V  V  I  C  T  T  N  L  H  S  S
     GATAAAGGCATTCCATTTACTTCTCCTGTGTTATTTGTACTACAAATTTGCATTCATCT
        4010                   4030                   4050

T  V  S  A  R  P  G  F  V  R  T  V  G  S  N  Q  L  L  N  L
     ACGGTGTCCGCTAAACCGGGCTTTGTGCGCACTGTGGTTCAAACCAGCTTTGAATCTC
        4130                   4150                   4170

I  I  N  G  Q  A  V  K  L  A  L  S  G  G  E  V  T  A  F  E
     ATTATAAATGGGCAGGCTGTTAAATTGGCTCTTTCTGGTGGAGAAGTGACAGCTTTTGAG
        4250                   4270                   4290
        2C ↓3A
     F  K  Q  S  W  S  D  L  F  R  K  C  T  T  D  E  E  Q  K  M
     TTTAAACAATCATGGTCTGATTTGTTCAGAAAGTGTACAACTGATGAGGAACAGAAAATG
        4370                   4390                   4410
```

FIG. 2E-2

```
     L  Y  K  L  K  L  K  E  P  D  T  Q  E  E  A  R  Q  W  F  K
     TTGTACAAGTTAAAATTGAAGGAACCTGATACTCAAGAGGAAGCGGCCAGTGTTTAAA
              3590              3610              3630

P  L  V  N  L  P  Q  S  R  P  E  P  V  V  C  V  L  R  G  A
     CCATTAGTTAACTTGCCCCAGAGCCGTCCAGAGCCCGTGTATGCGTCTTCCGGGGCA
              3710              3730              3750

V  G  K  Q  D  S  V  W  S  C  P  P  D  P  T  Y  F  D  G  Y
     GTTGGCAAGCAGGACAGTGTGTGGAGTTGTCCTCCTGACCCCACATATTTGATGGCTAT
              3830              3850              3870

K  Y  F  C  Q  M  V  S  T  T  A  F  V  P  P  M  A  H  L  D
     AAATATTTTTGCCAGATGGTCTCTACAACAGCTTTTGTACCACCTATGGCCCATTTGGAT
              3950              3970              3990

F  T  P  I  T  V  S  C  P  E  A  L  K  R  R  F  R  F  D  V
     TTTACCCCTATTACTGTGTTTCTTGTCCTGAAGCTCTTAAGAGAGGAGGTTTCGGTTTGATGTG
              4070              4090              4110

P  L  A  L  K  P  A  G  L  P  P  H  P  I  F  E  N  D  M  P
     CCACTTGCTCTTAAGCCAGCTGGTCTTCCCCCACACCCTATCTTTGAAAATGACATGCCC
              4190              4210              4230

L  I  E  M  I  L  S  E  V  Q  N  R  Q  D  T  H  K  M  P  I
     CTTATTGAGATGATACTGTCAGAAGTTCAAAACAGACAAGACACACAAAATGCCCATT
              4310              4330              4350

L  Q  F  L  I  D  N  K  D  S  E  I  L  R  A  F  V  S  E  R
     TTGCAGTTTTTAATTGACAATAAAGATTCAGAAATTCTCAGGGCGTTTGTTTCAGAACGC
              4430              4450              4470
```

FIG. 2F-1

```
    S  I  L  L  H  E  E  Y  L  K  W  E  S  Y  M  T  R  R  A  K
    TCCATTTTACTACATGAAGAGTATCTTAAATGGAGTCATATATGACCAGGAGACCAAG
             4490                      4510                      4530
                                                          3A ↓ 3B
    I  F  C  L  V  Y  S  M  Y  Q  L  F  K  T  P  D  E  Q  S  A
    ATTTTTTGTTTAGTTATTCTATGTATCAACTTTTTAAGACCCCTGACGAGCAATCAGCT
             4610                      4630                      4650
        3B ↓ 3C
    T  E  T  G  V  P  A  T  D  L  Q  Q  S  I  M  K  N  V  Q  P
    ACTGAGACTGGTGTACCAGCAACTGACTTGCAACAATCCATCATGAAAAATGTTCAGCCA
             4730                      4750                      4770
    N  S  Y  L  V  P  L  H  L  F  E  F  D  F  D  T  I  V  L  G
    AATTCATATTTGGTGCCCCTTCATTTGTTTGAATTTGATTTTGATACCATTGTGCTTGGT
             4850                      4870                      4890
    D  V  V  S  S  D  A  C  L  L  R  V  S  S  G  P  K  V  R  N
    GACGTGGTGTCATCAGATGCGTGTCTACTTCGAGTGTCATCGGGGCCTAAAGTTAGAAAT
             4970                      4990                      5010
    M  N  S  P  H  Q  A  R  T  V  F  F  G  S  F  L  T  V  R  K
    ATGAATTCACCACACCAGGCACCGTGTTTTTTGGCAGTTTTTTGACAGTGAGGAAG
             5090                      5110                      5130
    S  R  G  Y  C  G  A  A  I  V  A  G  S  P  A  R  I  I  G  I
    TCGCGTGGGTATTGTGGCGCTGCAATTGTGTGCTGGCTCACCTGCCCCGCATAATTGGTATC
             5210                      5230                      5250
                      3C ↓ 3D
    Q  L  W  P  Q  K  Q  G  N  V  S  R  L  D  D  D  V  R  V  S
    CAACTCTGGCCCCAGAAACAGGGCAACGTTAGTCGCCTTGATGACGATGTGAGGGTGTCT
             5330                      5350                      5370
```

FIG. 2F-2

```
       F  H  R  L  A  A  D  F  A  M  F  L  S  I  L  T  S  L  I  V
       TTTCACCGCCTGGCTGCTGATTTTGCTATGTTTCTATCCATTCTTACTTCACTGATTGTT
                              4550                              4570                              4590

Y  D  P  S  T  K  P  K  P  K  T  Q  E  V  K  T  L  K  I  R
       TATGATCCTTCAACTAAGCCAAAGCCAAAGACCCAGGAAGTGAAAACACTGAAGATTAGG
                              4670                              4690                              4710

I  E  L  Y  L  D  N  E  L  V  T  D  C  S  A  L  G  V  Y  D
       ATTGAGCTTTACCTTGACAATGAATTGGTTACTGACTGCTCTGCCTTGGGTGTTTATGAC
                              4790                              4810                              4830

G  R  H  Y  K  K  A  E  C  E  K  V  E  F  E  L  E  V  N  G
       GGACGTCATTACAAGAAAGCTGAGTGTGAGAAGGTAGAGTTTGAGCTTGAAGTGAATGGA
                              4910                              4930                              4950

I  V  H  L  F  T  N  E  I  E  L  K  K  M  T  Q  V  T  G  I
       ATTGTTCATCTTTTTACAAATGAAATTGAATTGAAGAAAATGACCCAAGTGACAGGAATC
                              5030                              5050                              5070

S  I  L  T  S  D  G  T  V  M  P  N  V  L  S  Y  A  A  Q  T
       TCCATCTTAACATCGGATGGACTGTAATGCCCAATGTTTGTCCTATGCCGCTCAGACC
                              5150                              5170                              5190

H  S  A  G  T  G  S  V  A  F  C  S  L  V  S  R  D  A  L  E
       CATTCAGCTGGCACTGGATCTGTTGCATTTTGCTCCCTGGTGTCCAGAGACGCGCTGGAG
                              5270                              5290                              5310

V  P  R  R  S  K  L  V  K  S  L  A  Y  P  I  F  K  P  D  Y
       GTTCCGCGCCGCTCCAAATTGGTGAAATCATTGGCTTACCCCATTTTCAAACCTGACTAT
                              5390                              5410                              5430
```

FIG. 2G-1

```
        G   P   A   P   L   S   Q   F   D   K   R   L   S   D   G   V   K   L   D   E
     GGCCCAGCGCCACTCTCTCAATTTGACAAGCGCCTGTCAGACGGCGTGAAGCTGGATGAA
         5450                5470                5490

L   R   A   A   H   V   Y   A   Q   K   V   F   S   R   I   G   F   D   N   Q
     TTGCGTGCGGCGCATGTATACGCCCAGAAGGTTTTCTCCCGGATTGGATTTGACAACCAG
         5570                5590                5610

T   A   P   G   L   P   Y   A   Q   Q   N   K   R   R   K   D   I   C   D   F
     ACCGCTCCCGGGCTGCCCTATGCTCAGCAAAATAAGAGAAGGAAAGACATCTGTGATTTT
         5690                5710                5730

S   N   L   V   Y   Q   S   F   L   K   D   E   I   R   P   L   E   K   V   R
     TCTAATTTGGTCTATCAATCATTTTTGAAAGATGAGATCCGCCCACTTGAGAAAGTTAGG
         5810                5830                5850

L   L   G   R   F   V   A   K   F   H   E   A   N   G   F   D   I   G   S   A
     CTCTTGGGCCGGTTTGTGGCAAAATTTCATGAAGCAAATGGATTTGACATTGGCTCAGCC
         5930                5950                5970

Y   V   Y   A   C   D   Y   S   R   F   D   A   N   H   A   A   D   A   M   R
     TATGTATATGCCTGTGACTACTCACGGTTCGATGCCAACCATGCAGCTGATGCAATGAGA
         6050                6070                6090

I   E   S   L   V   D   S   V   H   A   Y   E   E   K   R   Y   N   I   Y   G
     ATTGAGTCACTGGTTGATTCAGTGCATGCCTATGAAGAGAAAAGGTATAACATCTACGGT
         6170                6190                6210

I   L   A   A   M   M   K   A   Y   E   N   F   E   P   D   D   I   Q   V   I
     ATTCTTGCAGCTATGATGAAGGCTTATGAGAATTTTGAGCCAGATGACATTCAGGTCATT
         6290                6310                6330

P   V   F   S   S   F   G   Q   V   I   T   T   A   D   K   T   D   F   F   K
     CCTGTCTTTTCTAGTTTTGGACAGGTAATAACTACAGCTGACAAGACTGATTTTTTTAAA
         6410                6430                6450

K   P   V   M   D   V   K   T   L   E   A   I   L   S   F   V   R   P   G   T
     AAGCCAGTGATGGATGTGAAGACCCTTGAAGCAATCTTAAGCTTTGTTCGCCCAGGCACA
         6530                6550                6570

E   R   L   F   E   P   F   A   G   M   Y   F   V   P   T   W   R   L   A   P
     GAGCGCCTGTTTGAGCCCTTTGCTGGGATGTATTTCGTCCCTACTTGGCGACTTGCGCCT
         6650                6670                6690

TTTAGGCTTTTAAGGTGTTAAGTTTAAAGGTTAAGAGTTTTAGAAGTTAAGATAGAGTT
         6770                6790                6810
```

FIG. 2G-2

```
  V   V   F   A   K   H   T   G   D   K   E   I   S   A   Q   D   Q   K   W   L
GTGGTTTTTGCTAAACATACTGGAGACAAGGAGATTTCCGCACAGGACCAGAAATGGCTC
     5510                5530                5550

A   L   T   E   K   E   A   I   C   G   I   P   G   L   D   K   M   E   Q   D
GCTTTGACTGAAAAAGAGGCCATTTGTGGCATTCCTGGCCTTGACAAGATGGAGCAGGAC
     5630                5650                5670

E   E   G   R   L   K   G   A   E   L   Q   K   D   R   F   M   A   G   D   Y
GAAGAGGGCCGGCTGAAGGGCGCCGAACTCCAAAAGGACAGATTTATGGCTGGTGACTAC
     5750                5770                5790

A   G   K   T   R   L   I   D   V   P   P   M   P   H   V   V   V   G   R   Q
GCTGGAAAGACCCGCCTGATTGACGTGCCGCCGATGCCCCATGTGGTGGTTGGTAGGCAG
     5870                5890                5910

I   G   C   D   P   D   V   D   W   T   R   F   G   L   E   L   E   R   F   R
ATTGGATGTGACCCAGATGTGGACTGGACTCGGTTTGGCCTCGAGTTGGAGCGTTTCAGG
     5990                6010                6030

V   V   L   N   Y   F   F   S   E   D   H   G   F   D   P   G   V   P   A   F
GTTGTGCTTAACTACTTTTTCTCTGAGGACCACGGTTTCGACCCTGGTGTGCCTGCTTTT
     6110                6130                6150

G   L   P   S   G   C   S   C   T   S   I   L   N   T   I   L   N   N   V   Y
GGCTTGCCATCCGGGTGTTCCTGCACATCAATTTTGAATACCATCTTGAACAATGTTTAC
     6230                6250                6270

C   Y   G   D   D   C   L   I   A   S   D   F   E   I   D   F   Q   Q   L   V
TGCTATGGGGACGACTGCCTCATTGCTTCTGATTTTGAAATTGATTTCCAACAACTGGTG
     6350                6370                6390

L   T   T   L   S   E   V   T   F   L   K   R   A   F   V   L   T   A   F   Y
CTGACAACGCTTTCGGAGGTGACCTTCCTTAAGCGCGCTTTTGTTCTGACGGCCTTTTAC
     6470                6490                6510

Q   A   E   K   L   L   S   V   A   Q   L   A   G   H   C   E   P   E   Q   Y
CAGGCTGAAAAGCTCCTGTCCGTGGCGCAGTTGGCAGGCCACTGCGAACCGGAGCAGTAT
     6590                6610                6630
                                              3D
  A   V   V   D   E   A   W   M   L   N   S   F
GCAGTGGTTGATGAAGCTTGGATGCTAAATTCTTTTTGACTTTGTTTTTCTTTGTTTTCT
     6710                6730                6750

TAGTTTTTAGTTTTGAGC-poly(A)
     6830
```

FIG. 2H-I

```
-790                -770                -750
TAAGTAAAACGCTGTAACTGCATGATTTGCGCCTGTAGCCCAGTAAAACGCAGAAACCA
      -730                -710                -690
CAAGCAAAAACCTGTAGCGTCAGTAAAACGGGCACATTCACATACAGAGCTTCCGGCTT
      -670                -650                -630
TAAGGGTTACTGCTCGTAATGAGAGCACATGACAACTTGTCGAGATTACGCAACTGTCA
      -610                -590                -570
CGGGAGAGAGGAGCCCGTTTTCGGGCACTTGTCTCCTAAACAATGTTGGCGCATTTGC
      -550                -530                -510
GCGCCCCCCCTTTTTCAGCCCCCTGTCATTGACTGGTCGAAGCGTTCGCAATAAGACT
      -490                -470                -450
GGTCGTCACTTGGCTGTGTTCTATCGTTCAGGCTTTAGCGCCCTTGCGCGGGGCCGT
      -430                -410                -390
CAAGCCCGTGCGCTGTATAGCGCAGTAACCGGACAGCGGGTGCTGGATTTTCCGGT
      -370                -350                -330
GCCATTGCTCTGGATGGTGTCACCAAGCTGACAAATGCGGAGTGAACCTCACAAGCGAC
```

FIG. 2H-2

```
-310                    -290                    -270
ACGCCTGTGTAGCGCTGCCAAAAGGGAGCGGAACTCCCGCGAGGGTCCTCTG
      -250                    -230                    -210
GCCAAAAGCCCAGCGTTGATAGCGCCTTTGGGATGCAGGAACCCACCTGCCAGGTGTG
      -190                    -170                    -150
AAGTGGAGTGAGCGGATCTCCAATTGGTCTGTTCTGAACTACACCATTTACTGCTGTGA
      -130                    -110                     -90
AGAATGCCCTGGTTACAGCCCTGACCAGCCCTGCCCGTGACTCTCGAC
      -70                     -50                     -30
CGGCGCAGGGTCAAAAATTGTCTAAGCAGCAGGAACGCGGAGCGTTCTTTTCCTT
                                  -10                      30
TTGTACTGACATGATGGGCGTCTAAGGTGTATAGAGTTTGCGAGCAGACTCTGCTGGC
                 M  A  A  S  K  V  Y  R  V  C  E  Q  T  L  L  A
                                       70
AGGTGCCGTTCGCATGATGACAAA
 G  A  V  R  M  M  D  K
 50
```

FIG. 3(A)

```
FMDVO1K    1  MNTTDCFIALVQAIREIKALFLSRTTGKMELTLYNGEKKTFYSRPNNHDN-CWLNAILQL   59
              *.....:  :.:     *.: :   :.   *.:   .  :.** *****:. **
ERhV1      1  MAASKVYRVCEQTLLAGAVRMMDKFLQKRTVFPHLDKTIRLTGLHNYDNTCWLNALTQL   60

FMDVO1K   60  FRYVEEPFFDWVYSSPENLTLEAIKQLEDLTGL-ELHEGGPPALVIWNIKHLLHTGIGTA  118
              .:   :: ::** .:.::.*.:  :.  *:: * **  ****:**: .* :: *  **
ERhV1     61  TQILGIRLFDEHFGNRGLFTRKTIDWVSDQTGIKDLKSGAPPLVVVYKLWQHGHLDVGTM  120

FMDVO1K  119  SRPSEVCMVDGTDMCLADFHAGIFLKGQEHAVFACVTSNGWYAIDDEDFYPWTPDPSDVL  178
              :*.: *.  *: :.**  **:*.**  *. **: *. :*  :  :*.:. * .***
ERhV1    121  EKPRSITLWSGPKVCLSDFWACVSAK-PGHAVFYLLTSEGWICVDDKKIYPETPKTEDVL  179
                                       L ↓ VP4

FMDVO1K  179  VFVPYDQEPLNGEWKAKVQR----KLKGAGQSSPATGSQNQSGNTGSIINNYYMQQYQN  233
              **.***.*:  *.: *:.  .     .   *. :***  .*:  **.:*:::*******
ERhV1    180  VFAPYDFESLGKDPPKLHQRYEKAFELSGGGTSTPTTGNQNMSGNSGSIVQNFYMQQYQN  239
                                      L ↑ VP4             VP4 ↓ VP2

FMDVO1K  234  SMDTQLGDNAISGGSNEGSTDTTSTHTTNTQNNDWFSKLASSAFSGLFGALLADKKTEET  293
              *:*:.****.**  : ..:: :*. *.::.*  .. *:.**  *     ***********
ERhV1    240  SIDADLGDNVISPEGQGSNTSSSTSSSQSSGLGGWFSSLL----NLGTKLLADKKTEET  294
                                                             VP4 ↑ VP2

FMDVO1K  294  TLLEDRILTTRNGHTTSTTQSSVGVTYGYATAEDFVSGPNTSGLETRVVQAERFFKTHLF  353
              * :**** *.** .:**:..::  ****.***. .:. :: .  :  :* :
ERhV1    295  TNIEDRIETTVVGVTIINSQGSVGTTYCYSKPDGRPPSTVSDPVTRLGPTLSRHYTFKVG  354

FMDVO1K  354  DWVTSDSFGRCHLLELPTDHKGVYGSLTD---SYAYMRNGWDVEVTAVGNQFNGGCLLVA  410
              :**.:.**: :: :***. .*.  .:. .       ** ******:.** . .:****
ERhV1    355  EWPHSQSHGHAWICPLPGDKLKKMGSFHEVVKAHHLVKNGWDVVQVNPSFAHSGPLCVA  414
```

FIG. 3(B)

```
FMDVO1K  411 MVPELYSIQKREL----------YQLTLFPHQFINPRTNMTAHITVPFVGVNRYDQYK 458
             ***  .  . : . *     **.:*****:*.***   .*:.:*.******.....
ERhV1    415 AVPEYEHTHEKALKWSELEEPAYTYQQLSVFPHQLLNLRTNSSVHLVMPYIGPGQPTNLT 474
                                              VP2 ↓ VP3

FMDVO1K  459 VHKPWTLVVMVVAPLTVNTEGAPQIKVYANIAPTNVHVAGEFPSKEGIFPVACSDGYGGL 518
             :*.****:*::::..**. .:..*    *    .:**.:.*.*:.:*:. :: .:::
ERhV1    475 LHNPWTIVILILSELTGPGQTVP---VTMSVAPIDAMVNGPLPNPEAPIRVVSVPESDSF 531
                                                    VP2 ↑ VP3

FMDVO1K  519 VTTDPKTADPVYGKVFNPPRNQLPGRFTNLLDVAEACPTFLRFEGGVPYVTTKTDSDRVL 578
             : . *.*.*.*  ***** *:******:   .:*    .:    .   .
ERhV1    532 MSSVPDNSTPLYPKVVVPPR-QVPGRFTNFIDVAKQTYSFCSISGKPYFEVTNTSGDEPL 590

FMDVO1K  579 AQFDMSLAAKQMSNTFLAGLAQYYTQYSGTINLHFMFTGPTDAKARYMVAYAPPGMEPPK 638
             :* . *:*.** ::  ** *:.******:::  .. .*****...  **    .:**
ERhV1    591 FQMDVSLSAAELHGTYVASLSSFFAQYRGSLNFNFIFTGAAATKAKFLVAFVPPHSAAPK 650

FMDVO1K  639 TPEAAAHCIHAEWDTGLNSKFTFSIPYLSAADYAYTASGVAETTNVQGWVCLFQITHGKA 698
             *.:**.* ****:* .***.:: :***.:**.*      .:**:*:
ERhV1    651 TRDEAMACIHAVWDVGLNSAFSFNVPYPSPADFMAVYSAERTVVNVSGWLQVYALTALTS 710
                                                    VP3 ↓ VP1

FMDVO1K  699 DGDA------LVVLASAGKDFELRLPVD-ARAETTSAGESADPVTTVENYGGETQIQRR 751
              :*        ::*  .*:*:* :*..*: *    .**:: ***. ..
ERhV1    711 TDIAVNSKGRVLVAVSAGPDFSLRHPADLPDKQVTNVGEDGEPGETEPRH--ALSPVDMH 768
                                                    VP3 ↑ VP1

FMDVO1K  752 QHTDVSFIMDRFVKV---------TPQNQINILDLMQIPSHTLVGALLRASTYYFSDLEIA 803
             *******::****..*        *....:.:**  . ..:..    .:.******:*:
ERhV1    769 VHTDVSFLLDRFFDVETLELSNLTGSPATHVLDPFGSTAQLAWARLLNTCTYFFSDLELS 828
```

FIG. 3(C)

```
FMDVO1K   804  VKHEGDLT---------WVPNGAPEKALDNTTNPTAYHKAPLTRLALPYTAPHRVL-  850
                 :.        *  :* ****.*. *    .:  .:::.     *    .*: :
ERhV1     829  IQFKFTTTPSSVGEGFVWVKWLPVGAPTKTTDAWQLEGGNSVRIQKLAVAGMCPTVVFK  888

FMDVO1K   851  -----------ATVYNGECRYNRNAVPNLRGDLQVLAQKVAR-------TLPTSFNYGAIKATR  896
                          *..   . :  **    .  :.::.  .         *  :
ERhV1     889  IAGSRSQACASALPYTSMWRVVPVFYNGWGAPTKEKATYNWLPGAHFGSILLTSDAHDKG  948

VP1 ↓ 2A           2A ↓ 2B
FMDVO1K   897  VTELLYRMKRAETYCPRPL-LAIHPTEARHKQKIVAPV-KQTLNFDLLKLAGDVESNPGP  954
                 * * *    *  :: **** *  *: .*   *:::** *:.************
ERhV1     949  GCYLRYAFRAPAMYCPRPIPPAFTRPADKTRHKFPTNINKQCTNYSLLKLAGDVESNPGP 1008
                                                              VP1 ↑ 2A           2A ↑ 2B

FMDVO1K   955  FFFSDVRSNFSKLVETINQMQEDMSTKHGPDFNRLVSAFEELAIGVKAIRTGLDEAKPWY 1014
                :**                              * ::::: :**  ..*  :*    *
ERhV1    1009  TIFS-------------------------KASADLNALSTSLGELTGMLKDLKAKAETYSPFY 1046

FMDVO1K   1015 KLIKLLSRLSCMAAVAARSKDPVLVAIMLADTGLEILDSTFVVKKISDSLSSLFHVPAPV 1074
                *: *    *  :.:..*:.**::*******:*.*..*  :*  *: :..:  :
ERhV1    1047 KMAKMLFKLATLAVAAMRTKDPVVVMLIADFGLEVFDTGFFFSYFQEKLQPYMKTIPGK  1106

2B ↓ 2C
FMDVO1K   1075 FS----FGAPVLLAGLVKVASSFFRSTPEDLE-RAEKQLKARDINDIFAILKNGEWLVKLI 1130
                :*    :*.  :*.:*.** :  .****.:*. .**::::****::::*:
ERhV1    1107 ISDLVTDAATAAAQIPKGVYSFVSSFFETPEGVVEKQVSLRTVNDIFALLKNSDWFIKTL 1166
                                     2B ↑ 2C

FMDVO1K   1131 LAIRDWIKAWIASEEKF-VTMTDLVPGILEKQRDLNDPSKYKEAKEWLDNARQACLKSGN 1189
                :*::*::   ***:.:  .       . *      :       *    .   * *   :
ERhV1    1167 VALKKWLTSWFAQEQQADDALYSELEKYPLYKLKLKEPDTQEEARQWFKDMQQRALAVKD 1226
```

FIG. 3(D)

```
FMDVO1K  1190  VHIANLCKVVAPAPSKSRPEPVVCLRGKSGQGKSFLANVLAQAISTHFTGRIDSVWYCP  1249
ERhV1    1227  KGLFSLLQIPLVNLPQSRPEPVVCVLRGASGQGKSYLANLMAQAISLLLVGKQDSVWSCP  1286
                : *   .. :..  .. ******..***  *** ****::****   .:  **** **

FMDVO1K  1250  PDPDHFDGYNQQTVVVMDDLGQNPDGKDFKYFAQMVSTTGFIPPMASLEDKGKPFNSKVI  1309
ERhV1    1287  PDPTYFDGYNGQAVVIMDALGQDPNGADFKYFCQMVSTTAFVPPMAHLDDKGIPFTSPVV  1346
                *** .***** *.**:**.**:*.* ****.****** *:****  *:***:**.. *:

FMDVO1K  1310  IATTNLYSGFTPRTMVCPDALNRRFHFDIDVSAKDGY----KINSKLDIIKALEDTHANP  1365
ERhV1    1347  ICTTNLHSSFTPITVSCPEALKRRFRFDVTVSAKPGFVRTVSNQLLNLPLALKPAGLPP  1406
                * ****:*.*** *: ***:****.**:****     *:    **..  **** .*  *
                                                                  2C ↓ 3A
FMDVO1K  1366  VAMFQYDCALLNGMAVEMKRMQQDMFKPQPPLQNVYQLVQEVIDRVELHEKVSSHPIFKQ  1425
ERhV1    1407  HPIFENDMPIINGQAVKLALSGGEV------TAFELIEMILSEVQNRQDTHKMPIFKQ  1458
                  * :*: .::**:**::  .. :       ::*: *:: ..**:.:: :  ******
                                                                        2C ↑ 3A

FMDVO1K  1426  ISIPSQKSVLYFLIEKGQHEAAIEFFEGMVHDSIKEELRPLIQQTSFVKRAFKRLKENFE  1485
ERhV1    1459  SWSD-------LFRKCTTDEEQKMLQFLIDNKDSEILRAFVSERSILLHEEYLKWESYM  1510
                * . :      * .:   *:::: :**:   *:* * :: .: :   *  :*  * :

FMDVO1K  1486  IVALCLTLLANIVIMIRETRKRQKMVDDAVNEYIEKANITTDDKTLDEAEKSPLETSGAS  1545
ERhV1    1511  TRRAKFHRLAADFAMFLSILTSLIVIFCLVYSMYQLFKTPDEQSAYDPSTKPKPKTQEVK  1570
                  * : .**:.:.:: : :. :*:* *:  * ::: :.  :  :.   *     : .

3A ↓ 3B
FMDVO1K  1546  TVGFRERTLPGQKACDDVNSEPAQPVEEQPQAEGPYAGPLERQKPLKVRAKLPQQEGPYA  1605
ERhV1    1571  TLKIR-------------------------------------------------------  1575
                *  :*
```

FIG. 3(E)

```
                          3A ↓ 3B                                                      3B ↓ 3C
FMDVO1K  1606  GPMERQKPLKVKAKAPVVKEGPYEGPVKKPVALKVKAKNLIVTESGAPPTDLQKMVMGNT  1665
                                                  **.*.:*****.:*.*.
ERhV1    1576  ------------------------------------TETGVPATDLQQSIMKNV       1593
                                                                3B ↑ 3C

FMDVO1K  1666  KPVELILDGKTVAICCATGVFGTAYLVPRHLFAEKYDKIMVDGRAMTDSDYRVFEFEIKV  1725
               *:**.**..*.*:.****.***.::.:****.***..:*.:::**
ERhV1    1594  QPIELYLDNELVTDCSALGVYDNSYLVPLHLFEFDFTIVLGGRHYKAECEKVEFELEV   1653

FMDVO1K  1726  KGQDMLSDAALMVLHRGNRVRDITKHFRDTARMKKGTPVVGVINNADVGRLIFSGEALTY 1785
               *: : ****: :***.**::::***: . ; .:*****.:* .:* .* **
ERhV1    1654  NGDVVSSDACLLRVSSGPKVRNIVHLFTNEIELKKMTQVTGIMNSPHQARTVFFGSFLTV 1713

FMDVO1K  1786  KDIVVCMDGDTMPGLFAYRAATKAGYCGGAVLAKDGADTFIVGTHSAGGNGVGYCSCVSR 1845
               :. .***.::.****.*****. : .******.:::*   *.****.:.:****..***
ERhV1    1714  RKSILTSDGTVMPNVLSYAAQTSRGYCGAAIVA--GSPARIIGIHSAGTGSVAFCSLVSR 1771
                                                 3C ↓ 3D

FMDVO1K  1846  SMLLLKMKAHIDPEPHHEGLIVDTRDVEERVHVMRKTKLAPTVAHGVFNPEFGPAALSNKD 1905
               *   : .::.: :*    *     .  * :  *.*:.*.: : * ..:*:.**:::*
ERhV1    1772  DALEQLWPQKQGN------VSRLDDDVRVSVPRRSKLVKSLAYPIFKPDYGPAPLSQFD   1824
                                 3C ↑ 3D

FMDVO1K  1906  PRLNEGVVLDEVIFSKHKGDTKMSEEDKALFRRCAADYASRLHSVLGTANAPLSIYEAIK 1965
               ***.:** *****: *:* ****:..: .*: .:*. ** :***
ERhV1    1825  KRLSDGVKLDEVVFAKHTGDKEISAQDQKWLLRAAHVYAQKVFSRIGFDNQALTEKEAIC 1884

FMDVO1K  1966  GVDGLDAMEPDTAPGLPWALQGKRRGALIDFENGTVGPEVEAALKLMEKREYKFVCQTFL 2025
               *:.** **.****:* *.****:*   : * .:****.
ERhV1    1885  GIPGLDKMEQDTAPGLPYAQQNKRRKDICDFEEGRLKGAELQKDRFMAGDYSNLVYQSFL 1944
```

FIG. 3(F)

```
FMDVO1K  2026  KDEIRPLEKVRAGKTRIVDVLPVEHILYTRMMIGRFCAQMHSNNGPQIGSAVGCNPDVDW  2085
               ****************:;:**   . *  .:*::  .*  :;****;****:**;:****
ErhV1    1945  KDEIRPLEKVRAGKTRLIDVPPMPHVVVGRQLLGRFVAKFHEANGFDIGSAIGCDPDVDW  2004

FMDVO1K  2086  QRFGTHFAQYRNVWDVDYSAFDANHCSDAMNIMFEEVFRTEFGFHPNAEWILKTLVNTEH  2145
               ***  .: ..:  *:;:*** .***..:: : .   ::::: :.  ..  ..  :   *
ErhV1    2005  TRFGLELERFRYVYACDYSRFDANHAADAMRVVLNYFFSEDHGFDPGVPAFIESLVDSVH  2064

FMDVO1K  2146  AYENKRITVGGGMPSGCSATSIINTILNNIYVLYALRRHYEGVELDTYTMISYGDDIVVA  2205
               ***;:**..; :*:;*:****.****:*****;*:*: .  * ..*  .*::****..:*
ErhV1    2065  AYEEKRYNIYGGLPSGCSCTSILNTILNNVYILAAMMKAYENFEPDDIQVICYGDDCLIA  2124

FMDVO1K  2206  SDYDLDFEALKPHFKSLGQTITPADKSDKGFVLGHSITDVTFLKRHFHMDYGTGFYKPVM  2265
               *:  :**.. :.  :   *.*;.;. . ;   .: ;.*: *  *****   ********
ErhV1    2125  SDFEIDFQQLVPVFSSFGQVITTADKTD--FFKLTTLSEVTFLKRAFVL---TAFYKPVM  2179

FMDVO1K  2266  ASKTLEAILSFARRGTIQEKLISVAGLAVHSGPDEYRRLFEPFQGLFEIPSYR        2318
               ** *****:**.* *.****:****..:****;. **:****** .**:*::*
ErhV1    2180  DVKTLEAILSFVRPGTQAEKLLSVAQLAGHCEPEQYERLFEPFAGMYFVPTWR        2232
```

POLYPROTEIN

POLYMERASE

| VP1F | 5' | GTTGTGTTCAAGATTGCAGGC | 3' |
| VP1R1 | 5' | TTGCTCTCAACATCTCCAGC | 3' |
| VP1R2 | 5' | TAGCACCCTCCTTTATCATGCG | 3' |

SEQUENCE LISTING

```
<160> NUMBER OF SEQ ID NOS: 25

<210> SEQ ID NO 1
<211> LENGTH: 7278
<212> TYPE: DNA
<213> ORGANISM: equine rhinovirus 1
<220> FEATURE:
<221> NAME/KEY: CDS
```

-continued

<222> LOCATION: (436)..(7176)

<400> SEQUENCE: 1

```
ccgtcaagcc cgttgcctgt atagccaggt aaccggacag cggcttgctg gattttcccg     60
gtgccattgc tctggatggt gtcaccaagc tgacaaatgc ggagtgaacc tcacaaagcg    120
acacgcctgt ggtagcgctg cccaaaaggg agcggaactc cccgccgagg cggtcctctc    180
tggccaaaag cccagcgttg atagcgcctt ttgggatgca ggaaccccac ctgccaggtg    240
tgaagtggag tgagcggatc tccaatttgg tctgttctga actacaccat ttactgctgt    300
gaagaatgcc ctggaggcaa gctggttaca gccctgacca ggccctgccc gtgactctcg    360
accggcgcag ggtcaaaaat tgtctaagca gcagcaggaa cgcgggagcg tttcttttcc    420
ttttgtactg acatg atg gcg gcg tct aag gtg tat aga gtt tgc gag cag    471
              Met Ala Ala Ser Lys Val Tyr Arg Val Cys Glu Gln
                1               5                  10 act ctg ctg gca ggt gcc gtt cgc atg atg gac aaa ttc ttg caa aag    519
Thr Leu Leu Ala Gly Ala Val Arg Met Met Asp Lys Phe Leu Gln Lys
         15                  20                  25 aga act gtt ttt gtc ccc cat ctt gac aaa aca att cgt ttg act gga    567
Arg Thr Val Phe Val Pro His Leu Asp Lys Thr Ile Arg Leu Thr Gly
 30                  35                  40 ctc cac aat tat gac aat act tgc tgg ttg aat gcc ttg aca caa ctg    615
Leu His Asn Tyr Asp Asn Thr Cys Trp Leu Asn Ala Leu Thr Gln Leu
 45                  50                  55                  60 aca cag att ctt gga att cgg ctt ttt gat gaa cac ttc ggc aat aga    663
Thr Gln Ile Leu Gly Ile Arg Leu Phe Asp Glu His Phe Gly Asn Arg
                 65                  70                  75 ggt ctg ttc act cgg aaa aca att gat tgg gtg agt gac cag act ggt    711
Gly Leu Phe Thr Arg Lys Thr Ile Asp Trp Val Ser Asp Gln Thr Gly
         80                  85                  90 ata aaa gat cta aaa tca gga gca ccg cca ctc gtg gtg gtg tac aaa    759
Ile Lys Asp Leu Lys Ser Gly Ala Pro Pro Leu Val Val Val Tyr Lys
                 95                 100                 105 ctg tgg caa cat gga cac ttg gat gtc ggt acg atg gag aaa ccc cgg    807
Leu Trp Gln His Gly His Leu Asp Val Gly Thr Met Glu Lys Pro Arg
        110                 115                 120 tcg att act cta tgg tct ggc ccc aaa gtg tgt ctt tct gat ttc tgg    855
Ser Ile Thr Leu Trp Ser Gly Pro Lys Val Cys Leu Ser Asp Phe Trp
125                 130                 135                 140 gcc tgt gtt tcg gca aaa ccg gga cat gca gta ttc tac ctt ctc aca    903
Ala Cys Val Ser Ala Lys Pro Gly His Ala Val Phe Tyr Leu Leu Thr
                145                 150                 155 agc gag ggt tgg atc tgt gtt gat gac aag aaa ata tac cca gaa aca    951
Ser Glu Gly Trp Ile Cys Val Asp Asp Lys Lys Ile Tyr Pro Glu Thr
        160                 165                 170 ccc aaa aca gag gat gta ctt gtt ttt gcg ccc tat gac ttt gag tca    999
Pro Lys Thr Glu Asp Val Leu Val Phe Ala Pro Tyr Asp Phe Glu Ser
175                 180                 185 ctg ggc aag gac cca cca aag cta cac cag aga tat gaa aaa gca ttt   1047
Leu Gly Lys Asp Pro Pro Lys Leu His Gln Arg Tyr Glu Lys Ala Phe
        190                 195                 200 gag ctc agt ggc gga ggt aca tcc act cca aca act ggc aac caa aac   1095
Glu Leu Ser Gly Gly Gly Thr Ser Thr Pro Thr Thr Gly Asn Gln Asn
205                 210                 215                 220 atg tcc gga aac agt ggt tca att gtt caa aat ttt tac atg caa cag   1143
Met Ser Gly Asn Ser Gly Ser Ile Val Gln Asn Phe Tyr Met Gln Gln
                225                 230                 235
```

-continued

| | |
|---|---|
| tac cag aat tca att gac gca gac ctg gga gac aat gtg att agc cct<br>Tyr Gln Asn Ser Ile Asp Ala Asp Leu Gly Asp Asn Val Ile Ser Pro<br>240                       245                          250 | 1191 |
| gaa ggc cag ggc agc aac act agt agt tca acc tca tca agc caa tcc<br>Glu Gly Gln Gly Ser Asn Thr Ser Ser Ser Thr Ser Ser Ser Gln Ser<br>       255                      260                      265 | 1239 |
| tct ggc ttg ggc ggg tgg ttc tct agt ttg ctg aac ctt gga aca aaa<br>Ser Gly Leu Gly Gly Trp Phe Ser Ser Leu Leu Asn Leu Gly Thr Lys<br>270                       275                       280 | 1287 |
| cta ctg gct gac aag aag aca gaa gag act aca aac att gaa gac aga<br>Leu Leu Ala Asp Lys Lys Thr Glu Glu Thr Thr Asn Ile Glu Asp Arg<br>285                       290                       295                      300 | 1335 |
| att gaa aca aca gtg gtt gga gtc act att att aat tca caa gga tct<br>Ile Glu Thr Thr Val Val Gly Val Thr Ile Ile Asn Ser Gln Gly Ser<br>                     305                      310                       315 | 1383 |
| gtt gga aca acc tac tgt tac tcc aaa ccg gat ggt aga cca cca tcc<br>Val Gly Thr Thr Tyr Cys Tyr Ser Lys Pro Asp Gly Arg Pro Pro Ser<br>       320                      325                      330 | 1431 |
| aca gtg tca gac cca gtt acc aga ctt gga ccc acg ctt tcc agg cac<br>Thr Val Ser Asp Pro Val Thr Arg Leu Gly Pro Thr Leu Ser Arg His<br>335                       340                       345 | 1479 |
| tac aca ttt aag gta ggt gag tgg ccc cat tct caa tca cat ggt cac<br>Tyr Thr Phe Lys Val Gly Glu Trp Pro His Ser Gln Ser His Gly His<br>350                       355                       360 | 1527 |
| gca tgg atc tgt ccg ttg cca ggt gac aaa ctc aag aag atg ggc agt<br>Ala Trp Ile Cys Pro Leu Pro Gly Asp Lys Leu Lys Lys Met Gly Ser<br>365                       370                       375                      380 | 1575 |
| ttt cat gag gtt gtc aaa gcc cac cac ctg gtc aag aac ggc tgg gat<br>Phe His Glu Val Val Lys Ala His His Leu Val Lys Asn Gly Trp Asp<br>                     385                      390                       395 | 1623 |
| gtg gtt gtg cag gtg aat ccc tca ttt gct cac tcc ggg ccg ctg tgt<br>Val Val Val Gln Val Asn Pro Ser Phe Ala His Ser Gly Pro Leu Cys<br>                     400                      405                      410 | 1671 |
| gta gca gca gtg ccg gag tac gaa cac aca cat gag aaa gca ctc aag<br>Val Ala Ala Val Pro Glu Tyr Glu His Thr His Glu Lys Ala Leu Lys<br>               415                      420                      425 | 1719 |
| tgg tct gag ctt gag gaa cca gct tac aca tac caa caa ctt tca gtt<br>Trp Ser Glu Leu Glu Glu Pro Ala Tyr Thr Tyr Gln Gln Leu Ser Val<br>430                       435                       440 | 1767 |
| ttt ccc cac cag ttg cta aat ttg agg aca aat tca tca gtg cat ttg<br>Phe Pro His Gln Leu Leu Asn Leu Arg Thr Asn Ser Ser Val His Leu<br>445                       450                       455                      460 | 1815 |
| gtg atg ccc tac att ggg cca ggc caa cca aca aat ctg act ttg cac<br>Val Met Pro Tyr Ile Gly Pro Gly Gln Pro Thr Asn Leu Thr Leu His<br>                     465                      470                       475 | 1863 |
| aac ccg tgg acc att gtt att tta att ttg tct gaa ttg aca gga cct<br>Asn Pro Trp Thr Ile Val Ile Leu Ile Leu Ser Glu Leu Thr Gly Pro<br>                     480                      485                      490 | 1911 |
| ggc caa act gtg cct gtg acc atg tcg gtg gct ccc atc gat gca atg<br>Gly Gln Thr Val Pro Val Thr Met Ser Val Ala Pro Ile Asp Ala Met<br>             495                      500                      505 | 1959 |
| gtt aat ggg cct ctt cca aat cca gag gca ccg att aga gtg gtg tct<br>Val Asn Gly Pro Leu Pro Asn Pro Glu Ala Pro Ile Arg Val Val Ser<br>510                       515                      520 | 2007 |
| gtg cct gaa tca gat tct ttt atg tct tca gta cct gat aat tcg act<br>Val Pro Glu Ser Asp Ser Phe Met Ser Ser Val Pro Asp Asn Ser Thr<br>525                       530                       535                      540 | 2055 |
| cca cta tac ccc aag gtt gtg gtc cca ccg cgc caa gtt cct ggc cgg<br>Pro Leu Tyr Pro Lys Val Val Val Pro Pro Arg Gln Val Pro Gly Arg<br>                     545                      550                      555 | 2103 |

-continued

| | |
|---|---|
| ttt aca aat ttc att gat gtg gca aaa cag aca tat tca ttt tgt tcc<br>Phe Thr Asn Phe Ile Asp Val Ala Lys Gln Thr Tyr Ser Phe Cys Ser<br>560                              565                          570 | 2151 |
| att tct gga aaa cct tat ttt gag gtt acc aac acc tct ggg gac gag<br>Ile Ser Gly Lys Pro Tyr Phe Glu Val Thr Asn Thr Ser Gly Asp Glu<br>          575                          580                        585 | 2199 |
| cca ctg ttt cag atg gat gtg tcg ctc agt gcg gca gag cta cat ggc<br>Pro Leu Phe Gln Met Asp Val Ser Leu Ser Ala Ala Glu Leu His Gly<br>590                              595                          600 | 2247 |
| act tac gta gct agt ttg tca tca ttt ttt gca cag tac aga ggc tca<br>Thr Tyr Val Ala Ser Leu Ser Ser Phe Phe Ala Gln Tyr Arg Gly Ser<br>605                              610                        615                        620 | 2295 |
| ctt aat ttc aac ttt att ttc act ggt gca gca gcc act aag gca aag<br>Leu Asn Phe Asn Phe Ile Phe Thr Gly Ala Ala Ala Thr Lys Ala Lys<br>          625                          630                        635 | 2343 |
| ttt ctg gtt gct ttt gtg cct ccc cac agt gca gcg ccc aaa acg cgc<br>Phe Leu Val Ala Phe Val Pro Pro His Ser Ala Ala Pro Lys Thr Arg<br>                  640                          645                        650 | 2391 |
| gat gaa gca atg gcg tgc atc cat gcc gtg tgg gat gtt ggc ttg aac<br>Asp Glu Ala Met Ala Cys Ile His Ala Val Trp Asp Val Gly Leu Asn<br>655                              660                        665 | 2439 |
| tca gct ttt tct ttt aat gta cct tat ccc tcc cct gct gac ttc atg<br>Ser Ala Phe Ser Phe Asn Val Pro Tyr Pro Ser Pro Ala Asp Phe Met<br>670                              675                        680 | 2487 |
| gcc gtt tat tct gcg gaa cgg acg gtt gtg aat gtc tct gga tgg ctt<br>Ala Val Tyr Ser Ala Glu Arg Thr Val Val Asn Val Ser Gly Trp Leu<br>685                              690                        695                        700 | 2535 |
| caa gtt tat gca cta aca gct cta act tca act gac att gcc gtg aac<br>Gln Val Tyr Ala Leu Thr Ala Leu Thr Ser Thr Asp Ile Ala Val Asn<br>                  705                          710                        715 | 2583 |
| agt aaa ggc cgt gtg ctg gtt gct gtt tcc gcc ggc cca gac ttc tcc<br>Ser Lys Gly Arg Val Leu Val Ala Val Ser Ala Gly Pro Asp Phe Ser<br>                  720                          725                        730 | 2631 |
| ctt cgt cac ccg gcg gac ctg ccc gac aag cag gtt acc aat gtg gga<br>Leu Arg His Pro Ala Asp Leu Pro Asp Lys Gln Val Thr Asn Val Gly<br>                  735                          740                        745 | 2679 |
| gag gat ggt gaa ccc ggt gag aca gag cct cgt cat gct ttg tca ccc<br>Glu Asp Gly Glu Pro Gly Glu Thr Glu Pro Arg His Ala Leu Ser Pro<br>750                              755                        760 | 2727 |
| gtg gac atg cac gtg cac aca gat gtc agt ttc ttg ctt gac cgg ttc<br>Val Asp Met His Val His Thr Asp Val Ser Phe Leu Leu Asp Arg Phe<br>765                              770                        775                        780 | 2775 |
| ttt gat gtt gag aca ctt gag ctt tca aat ttg aca ggt tct cct gcc<br>Phe Asp Val Glu Thr Leu Glu Leu Ser Asn Leu Thr Gly Ser Pro Ala<br>          785                          790                        795 | 2823 |
| aca cat gtt ctg gat ccg ttt ggc tcg act gcc caa ctg gct tgg gca<br>Thr His Val Leu Asp Pro Phe Gly Ser Thr Ala Gln Leu Ala Trp Ala<br>                  800                          805                        810 | 2871 |
| cgt ctg cta aac act tgc acc tac ttc ttt tct gat ttg gaa ttg tca<br>Arg Leu Leu Asn Thr Cys Thr Tyr Phe Phe Ser Asp Leu Glu Leu Ser<br>          815                          820                        825 | 2919 |
| atc cag ttt aaa ttt acc acc act ccg tcc tct gtt gga gag ggc ttt<br>Ile Gln Phe Lys Phe Thr Thr Thr Pro Ser Ser Val Gly Glu Gly Phe<br>830                              835                        840 | 2967 |
| gtg tgg gtg aag tgg ctc cct gtt gga gca cca acc aag acc aca gat<br>Val Trp Val Lys Trp Leu Pro Val Gly Ala Pro Thr Lys Thr Thr Asp<br>845                              850                        855                        860 | 3015 |
| gct tgg cag tta gaa gga ggt gga aat tca gtt aga att caa aaa ttg<br>Ala Trp Gln Leu Glu Gly Gly Gly Asn Ser Val Arg Ile Gln Lys Leu<br>          865                          870                        875 | 3063 |

-continued

| | |
|---|---|
| gcc gtt gca ggg atg tgc ccc act gtt gtg ttc aag att gca ggc tcc<br>Ala Val Ala Gly Met Cys Pro Thr Val Val Phe Lys Ile Ala Gly Ser<br>           880                  885                890 | 3111 |
| cgt tca caa gcc tgt gct tca gcg ttg cca tat aca tca atg tgg cgt<br>Arg Ser Gln Ala Cys Ala Ser Ala Leu Pro Tyr Thr Ser Met Trp Arg<br>           895                  900                905 | 3159 |
| gtt gtg cca gtc ttt tac aat ggc tgg ggt gca cct acc aaa gaa aag<br>Val Val Pro Val Phe Tyr Asn Gly Trp Gly Ala Pro Thr Lys Glu Lys<br>910                  915                920 | 3207 |
| gca acc tac aat tgg ctt cct ggt gca cac ttt ggt tcc atc ttg ctg<br>Ala Thr Tyr Asn Trp Leu Pro Gly Ala His Phe Gly Ser Ile Leu Leu<br>925                  930                935                940 | 3255 |
| act tct gat gcg cat gat aaa gga ggg tgc tac ttg cgg tat gct ttc<br>Thr Ser Asp Ala His Asp Lys Gly Gly Cys Tyr Leu Arg Tyr Ala Phe<br>           945                  950                955 | 3303 |
| cgc gcg cca gcg atg tat tgc cct cga ccc att ccg ccg gct ttt acg<br>Arg Ala Pro Ala Met Tyr Cys Pro Arg Pro Ile Pro Pro Ala Phe Thr<br>           960                  965                970 | 3351 |
| cgt cca gcg gac aaa acc aga cat aaa ttt ccc act aac atc aac aaa<br>Arg Pro Ala Asp Lys Thr Arg His Lys Phe Pro Thr Asn Ile Asn Lys<br>           975                  980                985 | 3399 |
| cag tgt act aat tac tct ctc ctc aaa ttg gct gga gat gtt gag agc<br>Gln Cys Thr Asn Tyr Ser Leu Leu Lys Leu Ala Gly Asp Val Glu Ser<br>990                  995                1000 | 3447 |
| aac cct ggc ccc act att ttt tcc aaa gca tca gca gac ctg aat gcc<br>Asn Pro Gly Pro Thr Ile Phe Ser Lys Ala Ser Ala Asp Leu Asn Ala<br>1005                1010              1015              1020 | 3495 |
| ttg tca acg tcg cta ggt gaa ttg act ggc atg cta aaa gat ctt aaa<br>Leu Ser Thr Ser Leu Gly Glu Leu Thr Gly Met Leu Lys Asp Leu Lys<br>              1025              1030              1035 | 3543 |
| gcc aag gca gaa act tat tcc ccg ttt tac aaa atg gcc aaa atg ctt<br>Ala Lys Ala Glu Thr Tyr Ser Pro Phe Tyr Lys Met Ala Lys Met Leu<br>            1040              1045              1050 | 3591 |
| ttc aaa ctt gca aca cta gct gtg gca gct atg agg aca aag gac cca<br>Phe Lys Leu Ala Thr Leu Ala Val Ala Ala Met Arg Thr Lys Asp Pro<br>            1055              1060              1065 | 3639 |
| gta gtg gtg gtt atg ttg att gct gat ttc gga ttg gag gtc ttt gac<br>Val Val Val Val Met Leu Ile Ala Asp Phe Gly Leu Glu Val Phe Asp<br>     1070              1075              1080 | 3687 |
| act ggg ttt ttc ttt tcc tac ttt caa gag aag ttg cag cct tat atg<br>Thr Gly Phe Phe Phe Ser Tyr Phe Gln Glu Lys Leu Gln Pro Tyr Met<br>1085              1090              1095              1100 | 3735 |
| aaa act att cct ggt aag att tct gat ttg gtc act gat gcg gct acg<br>Lys Thr Ile Pro Gly Lys Ile Ser Asp Leu Val Thr Asp Ala Ala Thr<br>            1105              1110              1115 | 3783 |
| gct gcc gcc caa att cca aag gga gtg tat tct ttt gtg tcg tca ttt<br>Ala Ala Ala Gln Ile Pro Lys Gly Val Tyr Ser Phe Val Ser Ser Phe<br>            1120              1125              1130 | 3831 |
| ttc gaa acg cct gaa gga gtg gtt gag aag cag gtg tct ctt cgg aca<br>Phe Glu Thr Pro Glu Gly Val Val Glu Lys Gln Val Ser Leu Arg Thr<br>            1135              1140              1145 | 3879 |
| gtg aat gac ata ttt gct ttg ctt aaa aat tct gat tgg ttc ata aag<br>Val Asn Asp Ile Phe Ala Leu Leu Lys Asn Ser Asp Trp Phe Ile Lys<br>1150              1155              1160 | 3927 |
| act ctt gtt gcc ctc aag aaa tgg ctg aca tcc tgg ttt gct caa gaa<br>Thr Leu Val Ala Leu Lys Lys Trp Leu Thr Ser Trp Phe Ala Gln Glu<br>1165              1170              1175              1180 | 3975 |
| caa cag gca gat gat gcg ctc tat tca gaa ttg gaa aaa tat ccc ttg<br>Gln Gln Ala Asp Asp Ala Leu Tyr Ser Glu Leu Glu Lys Tyr Pro Leu<br>            1185              1190              1195 | 4023 |

-continued

| | |
|---|---|
| tac aag tta aaa ttg aag gaa cct gat act caa gag gaa gcg cgc cag<br>Tyr Lys Leu Lys Leu Lys Glu Pro Asp Thr Gln Glu Glu Ala Arg Gln<br>         1200                1205                1210 | 4071 |
| tgg ttt aaa gac atg cag cag cgt gct ctc gct gtg aag gac aaa ggt<br>Trp Phe Lys Asp Met Gln Gln Arg Ala Leu Ala Val Lys Asp Lys Gly<br>1215                1220                1225 | 4119 |
| ctc ttt tcc ctc ctg caa att cca tta gtt aac ttg ccc cag agc cgt<br>Leu Phe Ser Leu Leu Gln Ile Pro Leu Val Asn Leu Pro Gln Ser Arg<br>         1230                1235                1240 | 4167 |
| cca gag ccc gtt gta tgc gtc ctt cgg ggc gca tca ggg caa ggc aaa<br>Pro Glu Pro Val Val Cys Val Leu Arg Gly Ala Ser Gly Gln Gly Lys<br>1245                1250                1255                1260 | 4215 |
| tct tat ttg gca aat ctg atg gct caa gca att tcg ctt ctc ttg gtt<br>Ser Tyr Leu Ala Asn Leu Met Ala Gln Ala Ile Ser Leu Leu Leu Val<br>         1265                1270                1275 | 4263 |
| ggc aag cag gac agt gtg tgg agt tgt cct cct gac ccc aca tat ttt<br>Gly Lys Gln Asp Ser Val Trp Ser Cys Pro Pro Asp Pro Thr Tyr Phe<br>              1280                1285                1290 | 4311 |
| gat ggc tat aac gga cag gct gtg gtg att atg gat gca ttg ggc cag<br>Asp Gly Tyr Asn Gly Gln Ala Val Val Ile Met Asp Ala Leu Gly Gln<br>         1295                1300                1305 | 4359 |
| gat ccg aat ggt gct gac ttt aaa tat ttt tgc cag atg gtc tct aca<br>Asp Pro Asn Gly Ala Asp Phe Lys Tyr Phe Cys Gln Met Val Ser Thr<br>1310                1315                1320 | 4407 |
| aca gct ttt gta cca cct atg gcc cat ttg gat gat aaa ggc att cca<br>Thr Ala Phe Val Pro Pro Met Ala His Leu Asp Asp Lys Gly Ile Pro<br>1325                1330                1335                1340 | 4455 |
| ttt act tct cct gtt gtt att tgt act aca aat ttg cat tca tct ttt<br>Phe Thr Ser Pro Val Val Ile Cys Thr Thr Asn Leu His Ser Ser Phe<br>         1345                1350                1355 | 4503 |
| acc cct att act gtt tct tgt cct gaa gct ctt aag agg agg ttt cgg<br>Thr Pro Ile Thr Val Ser Cys Pro Glu Ala Leu Lys Arg Arg Phe Arg<br>              1360                1365                1370 | 4551 |
| ttt gat gtg acg gtg tcc gct aaa ccg ggc ttt gtg cgc act gtt ggt<br>Phe Asp Val Thr Val Ser Ala Lys Pro Gly Phe Val Arg Thr Val Gly<br>         1375                1380                1385 | 4599 |
| tca aac cag ctt ttg aat ctc cca ctt gct ctt aag cca gct ggt ctt<br>Ser Asn Gln Leu Leu Asn Leu Pro Leu Ala Leu Lys Pro Ala Gly Leu<br>1390                1395                1400 | 4647 |
| ccc cca cac cct atc ttt gaa aat gac atg ccc att ata aat ggg cag<br>Pro Pro His Pro Ile Phe Glu Asn Asp Met Pro Ile Ile Asn Gly Gln<br>1405                1410                1415                1420 | 4695 |
| gct gtt aaa ttg gct ctt tct ggt gga gaa gtg aca gct ttt gag ctt<br>Ala Val Lys Leu Ala Leu Ser Gly Gly Glu Val Thr Ala Phe Glu Leu<br>         1425                1430                1435 | 4743 |
| att gag atg ata ctg tca gaa gtt caa aac aga caa gac aca cac aaa<br>Ile Glu Met Ile Leu Ser Glu Val Gln Asn Arg Gln Asp Thr His Lys<br>              1440                1445                1450 | 4791 |
| atg ccc att ttt aaa caa tca tgg tct gat ttg ttc aga aag tgt aca<br>Met Pro Ile Phe Lys Gln Ser Trp Ser Asp Leu Phe Arg Lys Cys Thr<br>1455                1460                1465 | 4839 |
| act gat gag gaa cag aaa atg ttg cag ttt tta att gac aat aaa gat<br>Thr Asp Glu Glu Gln Lys Met Leu Gln Phe Leu Ile Asp Asn Lys Asp<br>1470                1475                1480 | 4887 |
| tca gaa att ctc agg gcg ttt gtt tca gaa cgc tcc att tta cta cat<br>Ser Glu Ile Leu Arg Ala Phe Val Ser Glu Arg Ser Ile Leu Leu His<br>1485                1490                1495                1500 | 4935 |
| gaa gag tat ctt aaa tgg gag tca tat atg acc agg aga gcc aag ttt<br>Glu Glu Tyr Leu Lys Trp Glu Ser Tyr Met Thr Arg Arg Ala Lys Phe<br>         1505                1510                1515 | 4983 |

-continued

```
cac cgc ctg gct gct gat ttt gct atg ttt cta tcc att ctt act tca      5031
His Arg Leu Ala Ala Asp Phe Ala Met Phe Leu Ser Ile Leu Thr Ser
        1520                1525                1530 ctg att gtt att ttt tgt tta gtt tat tct atg tat caa ctt ttt aag      5079
Leu Ile Val Ile Phe Cys Leu Val Tyr Ser Met Tyr Gln Leu Phe Lys
    1535                1540                1545 acc cct gac gag caa tca gct tat gat cct tca act aag cca aaa cca      5127
Thr Pro Asp Glu Gln Ser Ala Tyr Asp Pro Ser Thr Lys Pro Lys Pro
1550                1555                1560 aag acc cag gaa gtg aaa aca ctg aag att agg act gag act ggt gta      5175
Lys Thr Gln Glu Val Lys Thr Leu Lys Ile Arg Thr Glu Thr Gly Val
1565                1570                1575                1580 cca gca act gac ttg caa caa tcc atc atg aaa aat gtt cag cca att      5223
Pro Ala Thr Asp Leu Gln Gln Ser Ile Met Lys Asn Val Gln Pro Ile
        1585                1590                1595 gag ctt tac ctt gac aat gaa ttg gtt act gac tgc tct gcc ttg ggt      5271
Glu Leu Tyr Leu Asp Asn Glu Leu Val Thr Asp Cys Ser Ala Leu Gly
    1600                1605                1610 gtt tat gac aat tca tat ttg gtg ccc ctt cat ttg ttt gaa ttt gat      5319
Val Tyr Asp Asn Ser Tyr Leu Val Pro Leu His Leu Phe Glu Phe Asp
1615                1620                1625 ttt gat acc att gtg ctt ggt gga cgt cat tac aag aaa gct gag tgt      5367
Phe Asp Thr Ile Val Leu Gly Gly Arg His Tyr Lys Lys Ala Glu Cys
1630                1635                1640 gag aag gta gag ttt gag ctt gaa gtg aat gga gac gtg gtg tca tca      5415
Glu Lys Val Glu Phe Glu Leu Glu Val Asn Gly Asp Val Val Ser Ser
1645                1650                1655                1660 gat gcg tgt cta ctt cga gtg tca tcg ggg cct aaa gtt aga aat att      5463
Asp Ala Cys Leu Leu Arg Val Ser Ser Gly Pro Lys Val Arg Asn Ile
        1665                1670                1675 gtt cat ctt ttt aca aat gaa att gaa ttg aag aaa atg acc caa gtg      5511
Val His Leu Phe Thr Asn Glu Ile Glu Leu Lys Lys Met Thr Gln Val
    1680                1685                1690 aca gga atc atg aat tca cca cac cag gca cgc act gtg ttt ttt ggc      5559
Thr Gly Ile Met Asn Ser Pro His Gln Ala Arg Thr Val Phe Phe Gly
1695                1700                1705 agt ttt ttg aca gtg agg aag tcc atc tta aca tcg gat ggg act gta      5607
Ser Phe Leu Thr Val Arg Lys Ser Ile Leu Thr Ser Asp Gly Thr Val
1710                1715                1720 atg ccc aat gtt ttg tcc tat gcc gct cag acc tcg cgt ggg tat tgt      5655
Met Pro Asn Val Leu Ser Tyr Ala Ala Gln Thr Ser Arg Gly Tyr Cys
1725                1730                1735                1740 ggc gct gca att gtt gct ggc tca cct gcc cgc ata att ggt atc cat      5703
Gly Ala Ala Ile Val Ala Gly Ser Pro Ala Arg Ile Ile Gly Ile His
        1745                1750                1755 tca gct ggc act gga tct gtt gca ttt tgc tcc ctg tgt cca aga gac      5751
Ser Ala Gly Thr Gly Ser Val Ala Phe Cys Ser Leu Val Ser Arg Asp
    1760                1765                1770 gcg ctg gag caa ctc tgg ccc cag aaa cag ggc aac gtt agt cgc ctt      5799
Ala Leu Glu Gln Leu Trp Pro Gln Lys Gln Gly Asn Val Ser Arg Leu
1775                1780                1785 gat gac gat gtg agg gtg tct gtt ccg cgc cgc tcc aaa ttg gtg aaa      5847
Asp Asp Asp Val Arg Val Ser Val Pro Arg Arg Ser Lys Leu Val Lys
1790                1795                1800 tca ttg gct tac ccc att ttc aaa cct gac tat ggc cca gcg cca ctc      5895
Ser Leu Ala Tyr Pro Ile Phe Lys Pro Asp Tyr Gly Pro Ala Pro Leu
1805                1810                1815                1820 tct caa ttt gac aag cgc ctg tca gac ggc gtg aag ctg gat gaa gtg      5943
Ser Gln Phe Asp Lys Arg Leu Ser Asp Gly Val Lys Leu Asp Glu Val
        1825                1830                1835
```

```
gtt ttt gct aaa cat act gga gac aag gag att tcc gca cag gac cag      5991
Val Phe Ala Lys His Thr Gly Asp Lys Glu Ile Ser Ala Gln Asp Gln
        1840                1845                1850 aaa tgg ctc ttg cgt gcg gcg cat gta tac gcc cag aag gtt ttc tcc      6039
Lys Trp Leu Leu Arg Ala Ala His Val Tyr Ala Gln Lys Val Phe Ser
    1855                1860                1865 cgg att gga ttt gac aac cag gct ttg act gaa aaa gag gcc att tgt      6087
Arg Ile Gly Phe Asp Asn Gln Ala Leu Thr Glu Lys Glu Ala Ile Cys
1870                1875                1880 ggc att cct ggc ctt gac aag atg gag cag gac acc gct ccc ggg ctg      6135
Gly Ile Pro Gly Leu Asp Lys Met Glu Gln Asp Thr Ala Pro Gly Leu
1885                1890                1895                1900 ccc tat gct cag caa aat aag aga agg aaa gac atc tgt gat ttt gaa      6183
Pro Tyr Ala Gln Gln Asn Lys Arg Arg Lys Asp Ile Cys Asp Phe Glu
        1905                1910                1915 gag ggc cgg ctg aag ggc gcc gaa ctc caa aag gac aga ttt atg gct      6231
Glu Gly Arg Leu Lys Gly Ala Glu Leu Gln Lys Asp Arg Phe Met Ala
    1920                1925                1930 ggt gac tac tct aat ttg gtc tat caa tca ttt ttg aaa gat gag atc      6279
Gly Asp Tyr Ser Asn Leu Val Tyr Gln Ser Phe Leu Lys Asp Glu Ile
1935                1940                1945 cgc cca ctt gag aaa gtt agg gct gga aag acc cgc ctg att gac gtg      6327
Arg Pro Leu Glu Lys Val Arg Ala Gly Lys Thr Arg Leu Ile Asp Val
    1950                1955                1960 ccg ccg atg ccc cat gtg gtg gtt ggt agg cag ctc ttg ggc cgg ttt      6375
Pro Pro Met Pro His Val Val Val Gly Arg Gln Leu Leu Gly Arg Phe
1965                1970                1975                1980 gtg gca aaa ttt cat gaa gca aat gga ttt gac att ggc tca gcc att      6423
Val Ala Lys Phe His Glu Ala Asn Gly Phe Asp Ile Gly Ser Ala Ile
        1985                1990                1995 gga tgt gac cca gat gtg gac tgg act cgg ttt ggc ctc gag ttg gag      6471
Gly Cys Asp Pro Asp Val Asp Trp Thr Arg Phe Gly Leu Glu Leu Glu
    2000                2005                2010 cgt ttc agg tat gta tat gcc tgt gac tac tca cgg ttc gat gcc aac      6519
Arg Phe Arg Tyr Val Tyr Ala Cys Asp Tyr Ser Arg Phe Asp Ala Asn
2015                2020                2025 cat gca gct gat gca atg aga gtt gtg ctt aac tac ttt ttc tct gag      6567
His Ala Ala Asp Ala Met Arg Val Val Leu Asn Tyr Phe Phe Ser Glu
        2030                2035                2040 gac cac ggt ttc gac cct ggt gtg cct gct ttt att gag tca ctg gtt      6615
Asp His Gly Phe Asp Pro Gly Val Pro Ala Phe Ile Glu Ser Leu Val
2045                2050                2055                2060 gat tca gtg cat gcc tat gaa gag aaa agg tat aac atc tac ggt ggc      6663
Asp Ser Val His Ala Tyr Glu Glu Lys Arg Tyr Asn Ile Tyr Gly Gly
        2065                2070                2075 ttg cca tcc ggg tgt tcc tgc aca tca att ttg aat acc atc ttg aac      6711
Leu Pro Ser Gly Cys Ser Cys Thr Ser Ile Leu Asn Thr Ile Leu Asn
    2080                2085                2090 aat gtt tac att ctt gca gct atg atg aag gct tat gag aat ttt gag      6759
Asn Val Tyr Ile Leu Ala Ala Met Met Lys Ala Tyr Glu Asn Phe Glu
        2095                2100                2105 cca gat gac att cag gtc att tgc tat ggg gac gac tgc ctc att gct      6807
Pro Asp Asp Ile Gln Val Ile Cys Tyr Gly Asp Asp Cys Leu Ile Ala
    2110                2115                2120 tct gat ttt gaa att gat ttc caa caa ctg gtg cct gtc ttt tct agt      6855
Ser Asp Phe Glu Ile Asp Phe Gln Gln Leu Val Pro Val Phe Ser Ser
2125                2130                2135                2140 ttt gga cag gta ata act aca gct gac aag act gat ttt ttt aaa ctg      6903
Phe Gly Gln Val Ile Thr Thr Ala Asp Lys Thr Asp Phe Phe Lys Leu
        2145                2150                2155
```

-continued

```
aca acg ctt tcg gag gtg acc ttc ctt aag cgc gct ttt gtt ctg acg     6951
Thr Thr Leu Ser Glu Val Thr Phe Leu Lys Arg Ala Phe Val Leu Thr
            2160                2165                2170 gcc ttt tac aag cca gtg atg gat gtg aag acc ctt gaa gca atc tta     6999
Ala Phe Tyr Lys Pro Val Met Asp Val Lys Thr Leu Glu Ala Ile Leu
        2175                2180                2185 agc ttt gtt cgc cca ggc aca cag gct gaa aag ctc ctg tcc gtg gcg     7047
Ser Phe Val Arg Pro Gly Thr Gln Ala Glu Lys Leu Leu Ser Val Ala
    2190                2195                2200 cag ttg gca ggc cac tgc gaa ccg gag cag tat gag cgc ctg ttt gag     7095
Gln Leu Ala Gly His Cys Glu Pro Glu Gln Tyr Glu Arg Leu Phe Glu
2205                2210                2215                2220 ccc ttt gct ggg atg tat ttc gtc cct act tgg cga ctt gcg cct gca     7143
Pro Phe Ala Gly Met Tyr Phe Val Pro Thr Trp Arg Leu Ala Pro Ala
                2225                2230                2235 gtg gtt gat gaa gct tgg atg cta aat tct ttt tgactttgtt tttctttgtt   7196
Val Val Asp Glu Ala Trp Met Leu Asn Ser Phe
            2240                2245 ttcttttagg cttttaaggt gttaagttta aaggttaaga gtttttagaa gttaagatag   7256
agtttagttt ttagttttga gc                                            7278

<210> SEQ ID NO 2
<211> LENGTH: 2247
<212> TYPE: PRT
<213> ORGANISM: equine rhinovirus 1

<400> SEQUENCE: 2

Met Ala Ala Ser Lys Val Tyr Arg Val Cys Glu Gln Thr Leu Leu Ala
  1               5                  10                  15

Gly Ala Val Arg Met Met Asp Lys Phe Leu Gln Lys Arg Thr Val Phe
             20                  25                  30

Val Pro His Leu Asp Lys Thr Ile Arg Leu Thr Gly Leu His Asn Tyr
         35                  40                  45

Asp Asn Thr Cys Trp Leu Asn Ala Leu Thr Gln Leu Thr Gln Ile Leu
     50                  55                  60

Gly Ile Arg Leu Phe Asp Glu His Phe Gly Asn Arg Gly Leu Phe Thr
 65                  70                  75                  80

Arg Lys Thr Ile Asp Trp Val Ser Asp Gln Thr Gly Ile Lys Asp Leu
                 85                  90                  95

Lys Ser Gly Ala Pro Pro Leu Val Val Val Tyr Lys Leu Trp Gln His
            100                 105                 110

Gly His Leu Asp Val Gly Thr Met Glu Lys Pro Arg Ser Ile Thr Leu
        115                 120                 125

Trp Ser Gly Pro Lys Val Cys Leu Ser Asp Phe Trp Ala Cys Val Ser
    130                 135                 140

Ala Lys Pro Gly His Ala Val Phe Tyr Leu Leu Thr Ser Glu Gly Trp
145                 150                 155                 160

Ile Cys Val Asp Asp Lys Lys Ile Tyr Pro Glu Thr Pro Lys Thr Glu
                165                 170                 175

Asp Val Leu Val Phe Ala Pro Tyr Asp Phe Glu Ser Leu Gly Lys Asp
            180                 185                 190

Pro Pro Lys Leu His Gln Arg Tyr Glu Lys Ala Phe Glu Leu Ser Gly
        195                 200                 205

Gly Gly Thr Ser Thr Pro Thr Thr Gly Asn Gln Asn Met Ser Gly Asn
    210                 215                 220
```

-continued

```
Ser Gly Ser Ile Val Gln Asn Phe Tyr Met Gln Gln Tyr Gln Asn Ser
225                 230                 235                 240

Ile Asp Ala Asp Leu Gly Asp Asn Val Ile Ser Pro Glu Gly Gln Gly
            245                 250                 255

Ser Asn Thr Ser Ser Thr Ser Ser Ser Gln Ser Ser Gly Leu Gly
            260                 265                 270

Gly Trp Phe Ser Ser Leu Leu Asn Leu Gly Thr Lys Leu Leu Ala Asp
            275                 280                 285

Lys Lys Thr Glu Glu Thr Thr Asn Ile Glu Asp Arg Ile Glu Thr Thr
290                 295                 300

Val Val Gly Val Thr Ile Ile Asn Ser Gln Gly Ser Val Gly Thr Thr
305                 310                 315                 320

Tyr Cys Tyr Ser Lys Pro Asp Gly Arg Pro Pro Ser Thr Val Ser Asp
            325                 330                 335

Pro Val Thr Arg Leu Gly Pro Thr Leu Ser Arg His Tyr Thr Phe Lys
            340                 345                 350

Val Gly Glu Trp Pro His Ser Gln Ser His Gly His Ala Trp Ile Cys
            355                 360                 365

Pro Leu Pro Gly Asp Lys Leu Lys Lys Met Gly Ser Phe His Glu Val
370                 375                 380

Val Lys Ala His His Leu Val Lys Asn Gly Trp Asp Val Val Gln
385                 390                 395                 400

Val Asn Pro Ser Phe Ala His Ser Gly Pro Leu Cys Val Ala Ala Val
            405                 410                 415

Pro Glu Tyr Glu His Thr His Glu Lys Ala Leu Lys Trp Ser Glu Leu
            420                 425                 430

Glu Glu Pro Ala Tyr Thr Tyr Gln Gln Leu Ser Val Phe Pro His Gln
            435                 440                 445

Leu Leu Asn Leu Arg Thr Asn Ser Ser Val His Leu Val Met Pro Tyr
            450                 455                 460

Ile Gly Pro Gly Gln Pro Thr Asn Leu Thr Leu His Asn Pro Trp Thr
465                 470                 475                 480

Ile Val Ile Leu Ile Leu Ser Glu Leu Thr Gly Pro Gly Gln Thr Val
            485                 490                 495

Pro Val Thr Met Ser Val Ala Pro Ile Asp Ala Met Val Asn Gly Pro
            500                 505                 510

Leu Pro Asn Pro Glu Ala Pro Ile Arg Val Val Ser Val Pro Glu Ser
            515                 520                 525

Asp Ser Phe Met Ser Ser Val Pro Asp Asn Ser Thr Pro Leu Tyr Pro
            530                 535                 540

Lys Val Val Pro Pro Arg Gln Val Pro Gly Arg Phe Thr Asn Phe
545                 550                 555                 560

Ile Asp Val Ala Lys Gln Thr Tyr Ser Phe Cys Ser Ile Ser Gly Lys
            565                 570                 575

Pro Tyr Phe Glu Val Thr Asn Thr Ser Gly Asp Glu Pro Leu Phe Gln
            580                 585                 590

Met Asp Val Ser Leu Ser Ala Ala Glu Leu His Gly Thr Tyr Val Ala
            595                 600                 605

Ser Leu Ser Ser Phe Phe Ala Gln Tyr Arg Gly Ser Leu Asn Phe Asn
            610                 615                 620

Phe Ile Phe Thr Gly Ala Ala Ala Thr Lys Ala Lys Phe Leu Val Ala
625                 630                 635                 640
```

-continued

```
Phe Val Pro Pro His Ser Ala Ala Pro Lys Thr Arg Asp Glu Ala Met
            645                 650                 655
Ala Cys Ile His Ala Val Trp Asp Val Gly Leu Asn Ser Ala Phe Ser
            660                 665                 670
Phe Asn Val Pro Tyr Pro Ser Pro Ala Asp Phe Met Ala Val Tyr Ser
            675                 680                 685
Ala Glu Arg Thr Val Val Asn Val Ser Gly Trp Leu Gln Val Tyr Ala
            690                 695                 700
Leu Thr Ala Leu Thr Ser Thr Asp Ile Ala Val Asn Ser Lys Gly Arg
705                 710                 715                 720
Val Leu Val Ala Val Ser Ala Gly Pro Asp Phe Ser Leu Arg His Pro
            725                 730                 735
Ala Asp Leu Pro Asp Lys Gln Val Thr Asn Val Gly Glu Asp Gly Glu
            740                 745                 750
Pro Gly Glu Thr Glu Pro Arg His Ala Leu Ser Pro Val Asp Met His
            755                 760                 765
Val His Thr Asp Val Ser Phe Leu Leu Asp Arg Phe Phe Asp Val Glu
            770                 775                 780
Thr Leu Glu Leu Ser Asn Leu Thr Gly Ser Pro Ala Thr His Val Leu
785                 790                 795                 800
Asp Pro Phe Gly Ser Thr Ala Gln Leu Ala Trp Ala Arg Leu Leu Asn
            805                 810                 815
Thr Cys Thr Tyr Phe Phe Ser Asp Leu Glu Leu Ser Ile Gln Phe Lys
            820                 825                 830
Phe Thr Thr Thr Pro Ser Ser Val Gly Glu Gly Phe Val Trp Val Lys
            835                 840                 845
Trp Leu Pro Val Gly Ala Pro Thr Lys Thr Thr Asp Ala Trp Gln Leu
850                 855                 860
Glu Gly Gly Gly Asn Ser Val Arg Ile Gln Lys Leu Ala Val Ala Gly
865                 870                 875                 880
Met Cys Pro Thr Val Val Phe Lys Ile Ala Gly Ser Arg Ser Gln Ala
            885                 890                 895
Cys Ala Ser Ala Leu Pro Tyr Thr Ser Met Trp Arg Val Val Pro Val
            900                 905                 910
Phe Tyr Asn Gly Trp Gly Ala Pro Thr Lys Glu Lys Ala Thr Tyr Asn
            915                 920                 925
Trp Leu Pro Gly Ala His Phe Gly Ser Ile Leu Leu Thr Ser Asp Ala
            930                 935                 940
His Asp Lys Gly Gly Cys Tyr Leu Arg Tyr Ala Phe Arg Ala Pro Ala
945                 950                 955                 960
Met Tyr Cys Pro Arg Pro Ile Pro Pro Ala Phe Thr Arg Pro Ala Asp
            965                 970                 975
Lys Thr Arg His Lys Phe Pro Asn Ile Asn Lys Gln Cys Thr Asn
            980                 985                 990
Tyr Ser Leu Leu Lys Leu Ala Gly Asp Val Glu Ser Asn Pro Gly Pro
            995                1000                1005
Thr Ile Phe Ser Lys Ala Ser Ala Asp Leu Asn Ala Leu Ser Thr Ser
           1010                1015                1020
Leu Gly Glu Leu Thr Gly Met Leu Lys Asp Leu Lys Ala Lys Ala Glu
025                1030                1035                1040
Thr Tyr Ser Pro Phe Tyr Lys Met Ala Lys Met Leu Phe Lys Leu Ala
           1045                1050                1055
```

```
Thr Leu Ala Val Ala Ala Met Arg Thr Lys Asp Pro Val Val Val
        1060                1065                1070

Met Leu Ile Ala Asp Phe Gly Leu Glu Val Phe Asp Thr Gly Phe Phe
        1075                1080                1085

Phe Ser Tyr Phe Gln Glu Lys Leu Gln Pro Tyr Met Lys Thr Ile Pro
        1090                1095                1100

Gly Lys Ile Ser Asp Leu Val Thr Asp Ala Ala Thr Ala Ala Ala Gln
105                 1110                1115                1120

Ile Pro Lys Gly Val Tyr Ser Phe Val Ser Ser Phe Glu Thr Pro
        1125                1130                1135

Glu Gly Val Val Glu Lys Gln Val Ser Leu Arg Thr Val Asn Asp Ile
        1140                1145                1150

Phe Ala Leu Leu Lys Asn Ser Asp Trp Phe Ile Lys Thr Leu Val Ala
        1155                1160                1165

Leu Lys Lys Trp Leu Thr Ser Trp Phe Ala Gln Glu Gln Gln Ala Asp
        1170                1175                1180

Asp Ala Leu Tyr Ser Glu Leu Glu Lys Tyr Pro Leu Tyr Lys Leu Lys
185                 1190                1195                1200

Leu Lys Glu Pro Asp Thr Gln Glu Glu Ala Arg Gln Trp Phe Lys Asp
        1205                1210                1215

Met Gln Gln Arg Ala Leu Ala Val Lys Asp Lys Gly Leu Phe Ser Leu
        1220                1225                1230

Leu Gln Ile Pro Leu Val Asn Leu Pro Gln Ser Arg Pro Glu Pro Val
        1235                1240                1245

Val Cys Val Leu Arg Gly Ala Ser Gly Gln Gly Lys Ser Tyr Leu Ala
        1250                1255                1260

Asn Leu Met Ala Gln Ala Ile Ser Leu Leu Leu Val Gly Lys Gln Asp
265                 1270                1275                1280

Ser Val Trp Ser Cys Pro Pro Asp Pro Thr Tyr Phe Asp Gly Tyr Asn
        1285                1290                1295

Gly Gln Ala Val Val Ile Met Asp Ala Leu Gly Gln Asp Pro Asn Gly
        1300                1305                1310

Ala Asp Phe Lys Tyr Phe Cys Gln Met Val Ser Thr Thr Ala Phe Val
        1315                1320                1325

Pro Pro Met Ala His Leu Asp Asp Lys Gly Ile Pro Phe Thr Ser Pro
        1330                1335                1340

Val Val Ile Cys Thr Thr Asn Leu His Ser Ser Phe Thr Pro Ile Thr
345                 1350                1355                1360

Val Ser Cys Pro Glu Ala Leu Lys Arg Arg Phe Arg Phe Asp Val Thr
        1365                1370                1375

Val Ser Ala Lys Pro Gly Phe Val Arg Thr Val Gly Ser Asn Gln Leu
        1380                1385                1390

Leu Asn Leu Pro Leu Ala Leu Lys Pro Ala Gly Leu Pro Pro His Pro
        1395                1400                1405

Ile Phe Glu Asn Asp Met Pro Ile Ile Asn Gly Gln Ala Val Lys Leu
        1410                1415                1420

Ala Leu Ser Gly Gly Glu Val Thr Ala Phe Glu Leu Ile Glu Met Ile
425                 1430                1435                1440

Leu Ser Glu Val Gln Asn Arg Gln Asp Thr His Lys Met Pro Ile Phe
        1445                1450                1455

Lys Gln Ser Trp Ser Asp Leu Phe Arg Lys Cys Thr Thr Asp Glu Glu
        1460                1465                1470
```

```
-continued

Gln Lys Met Leu Gln Phe Leu Ile Asp Asn Lys Asp Ser Glu Ile Leu
        1475                1480                1485

Arg Ala Phe Val Ser Glu Arg Ser Ile Leu Leu His Glu Glu Tyr Leu
        1490                1495                1500

Lys Trp Glu Ser Tyr Met Thr Arg Arg Ala Lys Phe His Arg Leu Ala
505                 1510                1515                1520

Ala Asp Phe Ala Met Phe Leu Ser Ile Leu Thr Ser Leu Ile Val Ile
                1525                1530                1535

Phe Cys Leu Val Tyr Ser Met Tyr Gln Leu Phe Lys Thr Pro Asp Glu
                1540                1545                1550

Gln Ser Ala Tyr Asp Pro Ser Thr Lys Pro Lys Pro Lys Thr Gln Glu
                1555                1560                1565

Val Lys Thr Leu Lys Ile Arg Thr Glu Thr Gly Val Pro Ala Thr Asp
        1570                1575                1580

Leu Gln Gln Ser Ile Met Lys Asn Val Gln Pro Ile Glu Leu Tyr Leu
585                 1590                1595                1600

Asp Asn Glu Leu Val Thr Asp Cys Ser Ala Leu Gly Val Tyr Asp Asn
                1605                1610                1615

Ser Tyr Leu Val Pro Leu His Leu Phe Glu Phe Asp Phe Asp Thr Ile
                1620                1625                1630

Val Leu Gly Gly Arg His Tyr Lys Lys Ala Glu Cys Glu Lys Val Glu
        1635                1640                1645

Phe Glu Leu Glu Val Asn Gly Asp Val Val Ser Ser Asp Ala Cys Leu
        1650                1655                1660

Leu Arg Val Ser Ser Gly Pro Lys Val Arg Asn Ile Val His Leu Phe
665                 1670                1675                1680

Thr Asn Glu Ile Glu Leu Lys Lys Met Thr Gln Val Thr Gly Ile Met
                1685                1690                1695

Asn Ser Pro His Gln Ala Arg Thr Val Phe Phe Gly Ser Phe Leu Thr
                1700                1705                1710

Val Arg Lys Ser Ile Leu Thr Ser Asp Gly Thr Val Met Pro Asn Val
        1715                1720                1725

Leu Ser Tyr Ala Ala Gln Thr Ser Arg Gly Tyr Cys Gly Ala Ala Ile
        1730                1735                1740

Val Ala Gly Ser Pro Ala Arg Ile Ile Gly Ile His Ser Ala Gly Thr
745                 1750                1755                1760

Gly Ser Val Ala Phe Cys Ser Leu Val Ser Arg Asp Ala Leu Glu Gln
                1765                1770                1775

Leu Trp Pro Gln Lys Gln Gly Asn Val Ser Arg Leu Asp Asp Asp Val
        1780                1785                1790

Arg Val Ser Val Pro Arg Arg Ser Lys Leu Val Lys Ser Leu Ala Tyr
        1795                1800                1805

Pro Ile Phe Lys Pro Asp Tyr Gly Pro Ala Pro Leu Ser Gln Phe Asp
        1810                1815                1820

Lys Arg Leu Ser Asp Gly Val Lys Leu Asp Glu Val Val Phe Ala Lys
825                 1830                1835                1840

His Thr Gly Asp Lys Glu Ile Ser Ala Gln Asp Gln Lys Trp Leu Leu
                1845                1850                1855

Arg Ala Ala His Val Tyr Ala Gln Lys Val Phe Ser Arg Ile Gly Phe
                1860                1865                1870

Asp Asn Gln Ala Leu Thr Glu Lys Glu Ala Ile Cys Gly Ile Pro Gly
        1875                1880                1885
```

-continued

```
Leu Asp Lys Met Glu Gln Asp Thr Ala Pro Gly Leu Pro Tyr Ala Gln
    1890                1895                1900
Gln Asn Lys Arg Arg Lys Asp Ile Cys Asp Phe Glu Gly Arg Leu
905                 1910                1915                1920
Lys Gly Ala Glu Leu Gln Lys Asp Arg Phe Met Ala Gly Asp Tyr Ser
            1925                1930                1935
Asn Leu Val Tyr Gln Ser Phe Leu Lys Asp Glu Ile Arg Pro Leu Glu
        1940                1945                1950
Lys Val Arg Ala Gly Lys Thr Arg Leu Ile Asp Val Pro Pro Met Pro
    1955                1960                1965
His Val Val Gly Arg Gln Leu Leu Gly Arg Phe Val Ala Lys Phe
    1970                1975                1980
His Glu Ala Asn Gly Phe Asp Ile Gly Ser Ala Ile Gly Cys Asp Pro
985                 1990                1995                2000
Asp Val Asp Trp Thr Arg Phe Gly Leu Glu Leu Glu Arg Phe Arg Tyr
                2005                2010                2015
Val Tyr Ala Cys Asp Tyr Ser Arg Phe Asp Ala Asn His Ala Ala Asp
            2020                2025                2030
Ala Met Arg Val Val Leu Asn Tyr Phe Phe Ser Glu Asp His Gly Phe
        2035                2040                2045
Asp Pro Gly Val Pro Ala Phe Ile Glu Ser Leu Val Asp Ser Val His
    2050                2055                2060
Ala Tyr Glu Glu Lys Arg Tyr Asn Ile Tyr Gly Gly Leu Pro Ser Gly
065                 2070                2075                2080
Cys Ser Cys Thr Ser Ile Leu Asn Thr Ile Leu Asn Asn Val Tyr Ile
                2085                2090                2095
Leu Ala Ala Met Met Lys Ala Tyr Glu Asn Phe Glu Pro Asp Asp Ile
            2100                2105                2110
Gln Val Ile Cys Tyr Gly Asp Asp Cys Leu Ile Ala Ser Asp Phe Glu
        2115                2120                2125
Ile Asp Phe Gln Gln Leu Val Pro Val Phe Ser Ser Phe Gly Gln Val
    2130                2135                2140
Ile Thr Thr Ala Asp Lys Thr Asp Phe Phe Lys Leu Thr Thr Leu Ser
145                 2150                2155                2160
Glu Val Thr Phe Leu Lys Arg Ala Phe Val Leu Thr Ala Phe Tyr Lys
                2165                2170                2175
Pro Val Met Asp Val Lys Thr Leu Glu Ala Ile Leu Ser Phe Val Arg
            2180                2185                2190
Pro Gly Thr Gln Ala Glu Lys Leu Leu Ser Val Ala Gln Leu Ala Gly
        2195                2200                2205
His Cys Glu Pro Glu Gln Tyr Glu Arg Leu Phe Glu Pro Phe Ala Gly
    2210                2215                2220
Met Tyr Phe Val Pro Thr Trp Arg Leu Ala Pro Ala Val Val Asp Glu
225                 2230                2235                2240
Ala Trp Met Leu Asn Ser Phe
            2245

<210> SEQ ID NO 3
<211> LENGTH: 248
<212> TYPE: PRT
<213> ORGANISM: equine rhinovirus 1

<400> SEQUENCE: 3

Val Thr Asn Val Gly Glu Asp Gly Glu Pro Gly Glu Thr Glu Pro Arg
  1               5                  10                  15
```

```
His Ala Leu Ser Pro Val Asp Met His Val His Thr Asp Val Ser Phe
             20                  25                  30

Leu Leu Asp Arg Phe Phe Asp Val Glu Thr Leu Glu Leu Ser Asn Leu
         35                  40                  45

Thr Gly Ser Pro Ala Thr His Val Leu Asp Pro Phe Gly Ser Thr Ala
     50                  55                  60

Gln Leu Ala Trp Ala Arg Leu Leu Asn Thr Cys Thr Tyr Phe Phe Ser
 65                  70                  75                  80

Asp Leu Glu Leu Ser Ile Gln Phe Lys Phe Thr Thr Pro Ser Ser
                 85                  90                  95

Val Gly Glu Gly Phe Val Trp Val Lys Trp Leu Pro Val Gly Ala Pro
             100                 105                 110

Thr Lys Thr Thr Asp Ala Trp Gln Leu Glu Gly Gly Asn Ser Val
         115                 120                 125

Arg Ile Gln Lys Leu Ala Val Ala Gly Met Cys Pro Thr Val Val Phe
     130                 135                 140

Lys Ile Ala Gly Ser Arg Ser Gln Ala Cys Ala Ser Ala Leu Pro Tyr
145                 150                 155                 160

Thr Ser Met Trp Arg Val Val Pro Val Phe Tyr Asn Gly Trp Gly Ala
             165                 170                 175

Pro Thr Lys Glu Lys Ala Thr Tyr Asn Trp Leu Pro Gly Ala His Phe
         180                 185                 190

Gly Ser Ile Leu Leu Thr Ser Asp Ala His Asp Lys Gly Gly Cys Tyr
     195                 200                 205

Leu Arg Tyr Ala Phe Arg Ala Pro Ala Met Tyr Cys Pro Arg Pro Ile
     210                 215                 220

Pro Pro Ala Phe Thr Arg Pro Ala Asp Lys Thr Arg His Lys Phe Pro
225                 230                 235                 240

Thr Asn Ile Asn Lys Gln Cys Thr
                245

<210> SEQ ID NO 4
<211> LENGTH: 230
<212> TYPE: PRT
<213> ORGANISM: equine rhinovirus 1

<400> SEQUENCE: 4

Asp Lys Lys Thr Glu Glu Thr Thr Asn Ile Glu Asp Arg Ile Glu Thr
 1               5                  10                  15

Thr Val Val Gly Val Thr Ile Ile Asn Ser Gln Gly Ser Val Gly Thr
             20                  25                  30

Thr Tyr Cys Tyr Ser Lys Pro Asp Gly Arg Pro Pro Ser Thr Val Ser
         35                  40                  45

Asp Pro Val Thr Arg Leu Gly Pro Thr Leu Ser Arg His Tyr Thr Phe
     50                  55                  60

Lys Val Gly Glu Trp Pro His Ser Gln Ser His Gly His Ala Trp Ile
 65                  70                  75                  80

Cys Pro Leu Pro Gly Asp Lys Leu Lys Lys Met Gly Ser Phe His Glu
             85                  90                  95

Val Val Lys Ala His His Leu Val Lys Asn Gly Trp Asp Val Val Val
         100                 105                 110

Gln Val Asn Pro Ser Phe Ala His Ser Gly Pro Leu Cys Val Ala Ala
     115                 120                 125

Val Pro Glu Tyr Glu His Thr His Glu Lys Ala Leu Lys Trp Ser Glu
     130                 135                 140
```

```
Leu Glu Glu Pro Ala Tyr Thr Tyr Gln Gln Leu Ser Val Phe Pro His
145                 150                 155                 160

Gln Leu Leu Asn Leu Arg Thr Asn Ser Ser Val His Leu Val Met Pro
                165                 170                 175

Tyr Ile Gly Pro Gly Gln Pro Thr Asn Leu Thr Leu His Asn Pro Trp
            180                 185                 190

Thr Ile Val Ile Leu Ile Leu Ser Glu Leu Thr Gly Pro Gly Gln Thr
        195                 200                 205

Val Pro Val Thr Met Ser Val Ala Pro Ile Asp Ala Met Val Asn Gly
    210                 215                 220

Pro Leu Pro Asn Pro Glu
225                 230

<210> SEQ ID NO 5
<211> LENGTH: 226
<212> TYPE: PRT
<213> ORGANISM: equine rhinovirus 1

<400> SEQUENCE: 5

Ala Pro Ile Arg Val Val Ser Val Pro Glu Ser Asp Ser Phe Met Ser
1               5                   10                  15

Ser Val Pro Asp Asn Ser Thr Pro Leu Tyr Pro Lys Val Val Pro
            20                  25                  30

Pro Arg Gln Val Pro Gly Arg Phe Thr Asn Phe Ile Asp Val Ala Lys
        35                  40                  45

Gln Thr Tyr Ser Phe Cys Ser Ile Ser Gly Lys Pro Tyr Phe Glu Val
    50                  55                  60

Thr Asn Thr Ser Gly Asp Glu Pro Leu Phe Gln Met Asp Val Ser Leu
65                  70                  75                  80

Ser Ala Ala Glu Leu His Gly Thr Tyr Val Ala Ser Leu Ser Ser Phe
                85                  90                  95

Phe Ala Gln Tyr Arg Gly Ser Leu Asn Phe Asn Phe Ile Phe Thr Gly
            100                 105                 110

Ala Ala Ala Thr Lys Ala Lys Phe Leu Val Ala Phe Val Pro Pro His
        115                 120                 125

Ser Ala Ala Pro Lys Thr Arg Asp Glu Ala Met Ala Cys Ile His Ala
    130                 135                 140

Val Trp Asp Val Gly Leu Asn Ser Ala Phe Ser Phe Asn Val Pro Tyr
145                 150                 155                 160

Pro Ser Pro Ala Asp Phe Met Ala Val Tyr Ser Ala Glu Arg Thr Val
                165                 170                 175

Val Asn Val Ser Gly Trp Leu Gln Val Tyr Ala Leu Thr Ala Leu Thr
            180                 185                 190

Ser Thr Asp Ile Ala Val Asn Ser Lys Gly Arg Val Leu Val Ala Val
        195                 200                 205

Ser Ala Gly Pro Asp Phe Ser Leu Arg His Pro Ala Asp Leu Pro Asp
    210                 215                 220

Lys Gln
225

<210> SEQ ID NO 6
<211> LENGTH: 80
<212> TYPE: PRT
<213> ORGANISM: equine rhinovirus 1
```

-continued

```
<400> SEQUENCE: 6

Gly Gly Gly Thr Ser Thr Pro Thr Thr Gly Asn Gln Asn Met Ser Gly
 1               5                  10                  15

Asn Ser Gly Ser Ile Val Gln Asn Phe Tyr Met Gln Gln Tyr Gln Asn
            20                  25                  30

Ser Ile Asp Ala Asp Leu Gly Asp Asn Val Ile Ser Pro Glu Gly Gln
        35                  40                  45

Gly Ser Asn Thr Ser Ser Thr Ser Ser Gln Ser Ser Gly Leu
    50                  55                  60

Gly Gly Trp Phe Ser Ser Leu Leu Asn Leu Gly Thr Lys Leu Leu Ala
 65                 70                  75                  80

<210> SEQ ID NO 7
<211> LENGTH: 744
<212> TYPE: DNA
<213> ORGANISM: equine rhinovirus 1

<400> SEQUENCE: 7
gttaccaatg tgggagagga tggtgaaccc ggtgagacag agcctcgtca tgctttgtca      60
cccgtggaca tgcacgtgca cacagatgtc agtttcttgc ttgaccggtt ctttgatgtt     120
gagacacttg agctttcaaa tttgacaggt tctcctgcca cacatgttct ggatccgttt     180
ggctcgactg cccaactggc ttgggcacgt ctgctaaaca cttgcaccta cttcttttct     240
gatttggaat tgtcaatcca gtttaaattt accaccactc cgtcctctgt tggagagggc     300
tttgtgtggg tgaagtggct ccctgttgga gcaccaacca agaccacaga tgcttggcag     360
ttagaaggag gtggaaattc agttagaatt caaaaattgg ccgttgcagg gatgtgcccc     420
actgttgtgt tcaagattgc aggctcccgt tcacaagcct gtgcttcagc gttgccatat     480
acatcaatgt ggcgtgttgt gccagtcttt tacaatggct ggggtgcacc taccaaagaa     540
aaggcaacct acaattggct tcctggtgca cactttggtt ccatcttgct gacttctgat     600
gcgcatgata aggagggtg ctacttgcgg tatgctttcc gcgcgccagc gatgtattgc     660
cctcgaccca ttccgccggc ttttacgcgt ccagcggaca aaaccagaca taaatttccc     720
actaacatca acaaacagtg tact                                             744

<210> SEQ ID NO 8
<211> LENGTH: 690
<212> TYPE: DNA
<213> ORGANISM: equine rhinovirus 1

<400> SEQUENCE: 8
gacaagaaga cagaagagac tacaaacatt gaagacagaa ttgaaacaac agtggttgga      60
gtcactatta ttaattcaca aggatctgtt ggaacaacct actgttactc caaaccggat     120
ggtagaccac catccacagt gtcagaccca gttaccagac ttggacccac gctttccagg     180
cactacacat ttaaggtagg tgagtggccc cattctcaat cacatggtca cgcatggatc     240
tgtccgttgc caggtgacaa actcaagaag atgggcagtt tcatgaggt tgtcaaagcc     300 caccacctgg tcaagaacgg ctgggatgtg ttgtgcagg tgaatccctc atttgctcac     360
tccgggccgc tgtgtgtagc agcagtgccg gagtacgaac acacacatga aaagcactc     420 aagtggtctg agcttgagga accagcttac acataccaac aactttcagt ttttccccac     480
cagttgctaa atttgaggac aaattcatca gtgcatttgg tgatgcccta cattgggcca     540
ggccaaccaa caaatctgac tttgcacaac ccgtggacca ttgttatttt aattttgtct     600
```

-continued

```
gaattgacag gacctggcca aactgtgcct gtgaccatgt cggtggctcc catcgatgca    660
atggttaatg ggcctcttcc aaatccagag                                      690

<210> SEQ ID NO 9
<211> LENGTH: 678
<212> TYPE: DNA
<213> ORGANISM: equine rhinovirus 1

<400> SEQUENCE: 9
gcaccgatta gagtggtgtc tgtgcctgaa tcagattctt ttatgtcttc agtacctgat     60
aattcgactc cactataccc caaggttgtg gtcccaccgc gccaagttcc tggccggttt    120
acaaatttca ttgatgtggc aaaacagaca tattcatttt gttccatttc tggaaaacct    180
tattttgagg ttaccaacac ctctggggac gagccactgt ttcagatgga tgtgtcgctc    240
agtgcggcag agctacatgg cacttacgta gctagtttgt catcattttt tgcacagtac    300
agaggctcac ttaatttcaa ctttattttc actggtgcag cagccactaa ggcaaagttt    360
ctggttgctt ttgtgcctcc ccacagtgca gcgcccaaaa cgcgcgatga agcaatggcg    420
tgcatccatg ccgtgtggga tgttggcttg aactcagctt tttcttttaa tgtaccttat    480
ccctcccctg ctgacttcat ggccgtttat tctgcggaac ggacggttgt gaatgtctct    540
ggatggcttc aagtttatgc actaacagct ctaacttcaa ctgacattgc cgtgaacagt    600
aaaggccgtg tgctggttgc tgtttccgcc ggcccagact tctcccttcg tcacccggcg    660
gacctgcccg acaagcag                                                   678

<210> SEQ ID NO 10
<211> LENGTH: 240
<212> TYPE: DNA
<213> ORGANISM: equine rhinovirus 1

<400> SEQUENCE: 10
ggcggaggta catccactcc aacaactggc aaccaaaaca tgtccggaaa cagtggttca     60
attgttcaaa atttttacat gcaacagtac cagaattcaa ttgacgcaga cctgggagac    120
aatgtgatta gccctgaagg ccagggcagc aacactagta gttcaacctc atcaagccaa    180
tcctctggct tgggcgggtg gttctctagt ttgctgaacc ttggaacaaa actactggct    240

<210> SEQ ID NO 11
<211> LENGTH: 21
<212> TYPE: DNA
<213> ORGANISM: equine rhinovirus 1

<400> SEQUENCE: 11
gttgtgttca agattgcagg c                                                21

<210> SEQ ID NO 12
<211> LENGTH: 20
<212> TYPE: DNA
<213> ORGANISM: equine rhinovirus 1

<400> SEQUENCE: 12
ttgctctcaa catctccagc                                                  20

<210> SEQ ID NO 13
<211> LENGTH: 22
<212> TYPE: DNA
<213> ORGANISM: equine rhinovirus 1
```

-continued

```
<210> SEQ ID NO 14
<211> LENGTH: 33
<212> TYPE: DNA
<213> ORGANISM: equine rhinovirus 1

<400> SEQUENCE: 14
gctggatcca tgagtggcgg aggtacatcc act                                    33

<210> SEQ ID NO 15
<211> LENGTH: 30
<212> TYPE: DNA
<213> ORGANISM: equine rhinovirus 1

<400> SEQUENCE: 15
gctctgcagc aggtctgctg atgctttgga                                       30

<210> SEQ ID NO 16
<211> LENGTH: 32
<212> TYPE: DNA
<213> ORGANISM: equine rhinovirus 1

<400> SEQUENCE: 16
gctctgcaga tgattaggac tgagactggt gt                                    32

<210> SEQ ID NO 17
<211> LENGTH: 30
<212> TYPE: DNA
<213> ORGANISM: equine rhinovirus 1

<400> SEQUENCE: 17
gctggatcct tagccatagt caggtttgaa                                       30

<210> SEQ ID NO 18
<211> LENGTH: 25
<212> TYPE: DNA
<213> ORGANISM: equine rhinovirus 1

<400> SEQUENCE: 18
atccagcaag ccgctgtccg gttac                                            25

<210> SEQ ID NO 19
<211> LENGTH: 18
<212> TYPE: DNA
<213> ORGANISM: equine rhinovirus 1

<400> SEQUENCE: 19
cgaagagaca cctgcttc                                                    18

<210> SEQ ID NO 20
<211> LENGTH: 21
<212> TYPE: DNA
<213> ORGANISM: equine rhinovirus 1

<400> SEQUENCE: 20
ttctggtgga gaagtgacag c                                                21

<210> SEQ ID NO 21
<211> LENGTH: 19
<212> TYPE: DNA
<213> ORGANISM: equine rhinovirus 1
```

Sequence preceding SEQ ID NO 14:

```
<400> SEQUENCE: 13
tagcaccctc ctttatcatg cg                                               22
```

<400> SEQUENCE: 21
gtgagccagc aacaattgc                                                    19

<210> SEQ ID NO 22
<211> LENGTH: 865
<212> TYPE: DNA
<213> ORGANISM: equine rhinovirus 1
<220> FEATURE:
<221> NAME/KEY: CDS
<222> LOCATION: (794)..(865)

<400> SEQUENCE: 22

| | |
|---|---|
| taagtaaaac gctgtaactg catgatttgc gcctgtagcg ccagtaaaac gcagaaacca | 60 |
| caagcaaaaa cctgtagcgt cagtaaaacg cgcacattca catacagagc ttcccggctt | 120 |
| taagggttac tgctcgtaat gagagcacat gacaacttgt cgagattacg caactgtca | 180 |
| cgggagagag gagcccgttt tcgggcactt gtctcctaaa caatgttggc gcgcatttgc | 240 |
| gcgccccccc ccttttttcag cccctgtca ttgactggtc gaagcgttcg caataagact | 300 |
| ggtcgtcact tggctgttct atcgtttcag gctttagcgc gcccttgcgc ggcgggccgt | 360 |
| caagcccgtg cgctgtatag cgccaggtaa ccggacagcg gcgtgctgga ttttcccggt | 420 |
| gccattgctc tggatggtgt caccaagctg acaaatgcgg agtgaacctc acaaagcgac | 480 |
| acgcctgtgg tagcgctgcc caaaagggag cggaactccc cgccgaggcg gtcctctctg | 540 |
| gccaaaagcc cagcgttgat agcgcctttt gggatgcagg aaccccacct gccaggtgtg | 600 |
| aagtggagtg agcggatctc caatttggtc tgttctgaac tacaccattt actgctgtga | 660 |
| agaatgccct ggaggcaagc tggttacagc cctgaccagg ccctgcccgt gactctcgac | 720 |
| cggcgcaggg tcaaaaattg tctaagcagc agcaggaacg cgggagcgtt tcttttcctt | 780 |
| ttgtactgac atg atg gcg gcg tct aag gtg tat aga gtt tgc gag cag | 829 |
|                Met Ala Ala Ser Lys Val Tyr Arg Val Cys Glu Gln | |
|                 1       5           10 | |
| act ctg ctg gca ggt gcc gtt cgc atg atg gac aaa | 865 |
| Thr Leu Leu Ala Gly Ala Val Arg Met Met Asp Lys | |
|    15            20 | |

<210> SEQ ID NO 23
<211> LENGTH: 24
<212> TYPE: PRT
<213> ORGANISM: equine rhinovirus 1

<400> SEQUENCE: 23

Met Ala Ala Ser Lys Val Tyr Arg Val Cys Glu Gln Thr Leu Leu Ala
  1               5                  10                  15

Gly Ala Val Arg Met Met Asp Lys
            20

<210> SEQ ID NO 24
<211> LENGTH: 2318
<212> TYPE: PRT
<213> ORGANISM: Foot-and-mouth disease virus

<400> SEQUENCE: 24

Met Asn Thr Thr Asp Cys Phe Ile Ala Leu Val Gln Ala Ile Arg Glu
  1               5                  10                  15

Ile Lys Ala Leu Phe Leu Ser Arg Thr Thr Gly Lys Met Glu Leu Thr
            20                  25                  30

Leu Tyr Asn Gly Glu Lys Lys Thr Phe Tyr Ser Arg Pro Asn Asn His
        35                  40                  45

-continued

```
Asp Asn Cys Trp Leu Asn Ala Ile Leu Gln Leu Phe Arg Tyr Val Glu
 50                  55                  60
Glu Pro Phe Phe Asp Trp Val Tyr Ser Ser Pro Glu Asn Leu Thr Leu
 65                  70                  75                  80
Glu Ala Ile Lys Gln Leu Glu Asp Leu Thr Gly Leu Glu Leu His Glu
                 85                  90                  95
Gly Gly Pro Pro Ala Leu Val Ile Trp Asn Ile Lys His Leu Leu His
            100                 105                 110
Thr Gly Ile Gly Thr Ala Ser Arg Pro Ser Glu Val Cys Met Val Asp
        115                 120                 125
Gly Thr Asp Met Cys Leu Ala Asp Phe His Ala Gly Ile Phe Leu Lys
    130                 135                 140
Gly Gln Glu His Ala Val Phe Ala Cys Val Thr Ser Asn Gln Trp Tyr
145                 150                 155                 160
Ala Ile Asp Asp Glu Asp Phe Tyr Pro Trp Thr Pro Asp Pro Ser Asp
                165                 170                 175
Val Leu Val Phe Val Pro Tyr Asp Gln Glu Pro Leu Asn Gly Glu Trp
            180                 185                 190
Lys Ala Lys Val Gln Arg Lys Leu Lys Gly Ala Gly Gln Ser Ser Pro
        195                 200                 205
Ala Thr Gly Ser Gln Asn Gln Ser Gly Asn Thr Gly Ser Ile Ile Asn
    210                 215                 220
Asn Tyr Tyr Met Gln Gln Tyr Gln Asn Ser Met Asp Thr Gln Leu Gly
225                 230                 235                 240
Asp Asn Ala Ile Ser Gly Gly Ser Asn Glu Gly Ser Thr Asp Thr Thr
                245                 250                 255
Ser Thr His Thr Thr Asn Thr Gln Asn Asn Asp Trp Phe Ser Lys Leu
            260                 265                 270
Ala Ser Ser Ala Phe Ser Gly Leu Phe Gly Ala Leu Leu Ala Asp Lys
        275                 280                 285
Lys Thr Glu Glu Thr Thr Leu Leu Glu Asp Arg Ile Leu Thr Thr Arg
    290                 295                 300
Asn Gly His Thr Thr Ser Thr Thr Gln Ser Ser Val Gly Val Thr Tyr
305                 310                 315                 320
Gly Tyr Ala Thr Ala Glu Asp Phe Val Ser Gly Pro Asn Thr Ser Gly
                325                 330                 335
Leu Glu Thr Arg Val Val Gln Ala Glu Arg Phe Phe Lys Thr His Leu
            340                 345                 350
Phe Asp Trp Val Thr Ser Asp Ser Phe Gly Arg Cys His Leu Leu Glu
        355                 360                 365
Leu Pro Thr Asp His Lys Gly Val Tyr Gly Ser Leu Thr Asp Ser Tyr
    370                 375                 380
Ala Tyr Met Arg Asn Gly Trp Asp Val Glu Val Thr Ala Val Gly Asn
385                 390                 395                 400
Gln Phe Asn Gly Gly Cys Leu Leu Val Ala Met Val Pro Glu Leu Tyr
                405                 410                 415
Ser Ile Gln Lys Arg Glu Leu Tyr Gln Leu Thr Leu Phe Pro His Gln
            420                 425                 430
Phe Ile Asn Pro Arg Thr Asn Met Thr Ala His Ile Thr Val Pro Phe
        435                 440                 445
Val Gly Val Asn Arg Tyr Asp Gln Tyr Lys Val His Lys Pro Trp Thr
    450                 455                 460
```

```
Leu Val Met Val Val Ala Pro Leu Thr Val Asn Thr Glu Gly Ala
465                 470                 475                 480

Pro Gln Ile Lys Val Tyr Ala Asn Ile Ala Pro Thr Asn Val His Val
                485                 490                 495

Ala Gly Glu Phe Pro Ser Lys Glu Gly Ile Phe Pro Val Ala Cys Ser
            500                 505                 510

Asp Gly Tyr Gly Gly Leu Val Thr Thr Asp Pro Lys Thr Ala Asp Pro
        515                 520                 525

Val Tyr Gly Lys Val Phe Asn Pro Pro Arg Asn Gln Leu Pro Gly Arg
    530                 535                 540

Phe Thr Asn Leu Leu Asp Val Ala Glu Ala Cys Pro Thr Phe Leu Arg
545                 550                 555                 560

Phe Glu Gly Gly Val Pro Tyr Val Thr Thr Lys Thr Asp Ser Asp Arg
                565                 570                 575

Val Leu Ala Gln Phe Asp Met Ser Leu Ala Ala Lys Gln Met Ser Asn
            580                 585                 590

Thr Phe Leu Ala Gly Leu Ala Gln Tyr Tyr Thr Gln Tyr Ser Gly Thr
        595                 600                 605

Ile Asn Leu His Phe Met Phe Thr Gly Pro Thr Asp Ala Lys Ala Arg
    610                 615                 620

Tyr Met Val Ala Tyr Ala Pro Pro Gly Met Glu Pro Pro Lys Thr Pro
625                 630                 635                 640

Glu Ala Ala Ala His Cys Ile His Ala Glu Trp Asp Thr Gly Leu Asn
                645                 650                 655

Ser Lys Phe Thr Phe Ser Ile Pro Tyr Leu Ser Ala Ala Asp Tyr Ala
            660                 665                 670

Tyr Thr Ala Ser Gly Val Ala Glu Thr Thr Asn Val Gln Gly Trp Val
        675                 680                 685

Cys Leu Phe Gln Ile Thr His Gly Lys Ala Asp Gly Asp Ala Leu Val
    690                 695                 700

Val Leu Ala Ser Ala Gly Lys Asp Phe Glu Leu Arg Leu Pro Val Asp
705                 710                 715                 720

Ala Arg Ala Glu Thr Thr Ser Ala Gly Glu Ser Ala Asp Pro Val Thr
                725                 730                 735

Thr Thr Val Glu Asn Tyr Gly Gly Glu Thr Gln Ile Gln Arg Arg Gln
            740                 745                 750

His Thr Asp Val Ser Phe Ile Met Asp Arg Phe Val Lys Val Thr Pro
        755                 760                 765

Gln Asn Gln Ile Asn Ile Leu Asp Leu Met Gln Ile Pro Ser His Thr
    770                 775                 780

Leu Val Gly Ala Leu Leu Arg Ala Ser Thr Tyr Tyr Phe Ser Asp Leu
785                 790                 795                 800

Glu Ile Ala Val Lys His Glu Gly Asp Leu Thr Trp Val Pro Asn Gly
                805                 810                 815

Ala Pro Glu Lys Ala Leu Asp Asn Thr Thr Asn Pro Thr Ala Tyr His
            820                 825                 830

Lys Ala Pro Leu Thr Arg Leu Ala Leu Pro Tyr Thr Ala Pro His Arg
        835                 840                 845

Val Leu Ala Thr Val Tyr Asn Gly Glu Cys Arg Tyr Asn Arg Asn Ala
    850                 855                 860

Val Pro Asn Leu Arg Gly Asp Leu Gln Val Leu Ala Gln Lys Val Ala
865                 870                 875                 880
```

-continued

```
Arg Thr Leu Pro Thr Ser Phe Asn Tyr Gly Ala Ile Lys Ala Thr Arg
                885                 890                 895

Val Thr Glu Leu Leu Tyr Arg Met Lys Arg Ala Glu Thr Tyr Cys Pro
            900                 905                 910

Arg Pro Leu Leu Ala Ile His Pro Thr Glu Ala Arg His Lys Gln Lys
        915                 920                 925

Ile Val Ala Pro Val Lys Gln Thr Leu Asn Phe Asp Leu Leu Lys Leu
    930                 935                 940

Ala Gly Asp Val Glu Ser Asn Pro Gly Pro Phe Phe Phe Ser Asp Val
945                 950                 955                 960

Arg Ser Asn Phe Ser Lys Leu Val Glu Thr Ile Asn Gln Met Gln Glu
                965                 970                 975

Asp Met Ser Thr Lys His Gly Pro Asp Phe Asn Arg Leu Val Ser Ala
            980                 985                 990

Phe Glu Glu Leu Ala Ile Gly Val Lys Ala Ile Arg Thr Gly Leu Asp
        995                 1000                1005

Glu Ala Lys Pro Trp Tyr Lys Leu Ile Lys Leu Leu Ser Arg Leu Ser
    1010                1015                1020

Cys Met Ala Ala Val Ala Ala Arg Ser Lys Asp Pro Val Leu Val Ala
1025                1030                1035                1040

Ile Met Leu Ala Asp Thr Gly Leu Glu Ile Leu Asp Ser Thr Phe Val
                1045                1050                1055

Val Lys Lys Ile Ser Asp Ser Leu Ser Ser Leu Phe His Val Pro Ala
            1060                1065                1070

Pro Val Phe Ser Phe Gly Ala Pro Val Leu Leu Ala Gly Leu Val Lys
        1075                1080                1085

Val Ala Ser Ser Phe Phe Arg Ser Thr Pro Glu Asp Leu Glu Arg Ala
    1090                1095                1100

Glu Lys Gln Leu Lys Ala Arg Asp Ile Asn Asp Ile Phe Ala Ile Leu
1105                1110                1115                1120

Lys Asn Gly Glu Trp Leu Val Lys Leu Ile Leu Ala Ile Arg Asp Trp
                1125                1130                1135

Ile Lys Ala Trp Ile Ala Ser Glu Glu Lys Phe Val Thr Met Thr Asp
            1140                1145                1150

Leu Val Pro Gly Ile Leu Glu Lys Gln Arg Asp Leu Asn Asp Pro Ser
        1155                1160                1165

Lys Tyr Lys Glu Ala Lys Glu Trp Leu Asp Asn Ala Arg Gln Ala Cys
    1170                1175                1180

Leu Lys Ser Gly Asn Val His Ile Ala Asn Leu Cys Lys Val Val Ala
1185                1190                1195                1200

Pro Ala Pro Ser Lys Ser Arg Pro Glu Pro Val Val Val Cys Leu Arg
                1205                1210                1215

Gly Lys Ser Gly Gln Gly Lys Ser Phe Leu Ala Asn Val Leu Ala Gln
            1220                1225                1230

Ala Ile Ser Thr His Phe Thr Gly Arg Ile Asp Ser Val Trp Tyr Cys
        1235                1240                1245

Pro Pro Asp Pro Asp His Phe Asp Gly Tyr Asn Gln Gln Thr Val Val
    1250                1255                1260

Val Met Asp Asp Leu Gly Gln Asn Pro Asp Gly Lys Asp Phe Lys Tyr
1265                1270                1275                1280

Phe Ala Gln Met Val Ser Thr Thr Gly Phe Ile Pro Pro Met Ala Ser
                1285                1290                1295
```

```
Leu Glu Asp Lys Gly Lys Pro Phe Asn Ser Lys Val Ile Ile Ala Thr
            1300                1305                1310

Thr Asn Leu Tyr Ser Gly Phe Thr Pro Arg Thr Met Val Cys Pro Asp
        1315                1320                1325

Ala Leu Asn Arg Arg Phe His Phe Asp Ile Asp Val Ser Ala Lys Asp
    1330                1335                1340

Gly Tyr Lys Ile Asn Ser Lys Leu Asp Ile Ile Lys Ala Leu Glu Asp
1345                1350                1355                1360

Thr His Ala Asn Pro Val Ala Met Phe Gln Tyr Asp Cys Ala Leu Leu
            1365                1370                1375

Asn Gly Met Ala Val Glu Met Lys Arg Met Gln Gln Asp Met Phe Lys
        1380                1385                1390

Pro Gln Pro Pro Leu Gln Asn Val Tyr Gln Leu Val Gln Glu Val Ile
            1395                1400                1405

Asp Arg Val Glu Leu His Glu Lys Val Ser Ser His Pro Ile Phe Lys
        1410                1415                1420

Gln Ile Ser Ile Pro Ser Gln Lys Ser Val Leu Tyr Phe Leu Ile Glu
1425                1430                1435                1440

Lys Gly Gln His Glu Ala Ala Ile Glu Phe Phe Glu Gly Met Val His
            1445                1450                1455

Asp Ser Ile Lys Glu Glu Leu Arg Pro Leu Ile Gln Gln Thr Ser Phe
        1460                1465                1470

Val Lys Arg Ala Phe Lys Arg Leu Lys Glu Asn Phe Glu Ile Val Ala
    1475                1480                1485

Leu Cys Leu Thr Leu Leu Ala Asn Ile Val Ile Met Ile Arg Glu Thr
        1490                1495                1500

Arg Lys Arg Gln Lys Met Val Asp Asp Ala Val Asn Glu Tyr Ile Glu
1505                1510                1515                1520

Lys Ala Asn Ile Thr Thr Asp Asp Lys Thr Leu Asp Glu Ala Glu Lys
            1525                1530                1535

Ser Pro Leu Glu Thr Ser Gly Ala Ser Thr Val Gly Phe Arg Glu Arg
        1540                1545                1550

Thr Leu Pro Gly Gln Lys Ala Cys Asp Asp Val Asn Ser Glu Pro Ala
    1555                1560                1565

Gln Pro Val Glu Glu Gln Pro Gln Ala Glu Gly Pro Tyr Ala Gly Pro
        1570                1575                1580

Leu Glu Arg Gln Lys Pro Leu Lys Val Arg Ala Lys Leu Pro Gln Gln
1585                1590                1595                1600

Glu Gly Pro Tyr Ala Gly Pro Met Glu Arg Gln Lys Pro Leu Lys Val
            1605                1610                1615

Lys Ala Lys Ala Pro Val Val Lys Glu Gly Pro Tyr Glu Gly Pro Val
        1620                1625                1630

Lys Lys Pro Val Ala Leu Lys Val Lys Ala Lys Asn Leu Ile Val Thr
    1635                1640                1645

Glu Ser Gly Ala Pro Pro Thr Asp Leu Gln Lys Met Val Met Gly Asn
        1650                1655                1660

Thr Lys Pro Val Glu Leu Ile Leu Asp Gly Lys Thr Val Ala Ile Cys
1665                1670                1675                1680

Cys Ala Thr Gly Val Phe Gly Thr Ala Tyr Leu Val Pro Arg His Leu
            1685                1690                1695

Phe Ala Glu Lys Tyr Asp Lys Ile Met Val Asp Gly Arg Ala Met Thr
        1700                1705                1710
```

-continued

```
Asp Ser Asp Tyr Arg Val Phe Glu Phe Glu Ile Lys Val Lys Gly Gln
    1715                1720                1725

Asp Met Leu Ser Asp Ala Ala Leu Met Val Leu His Arg Gly Asn Arg
    1730                1735                1740

Val Arg Asp Ile Thr Lys His Phe Arg Asp Thr Ala Arg Met Lys Lys
1745                1750                1755                1760

Gly Thr Pro Val Val Gly Val Ile Asn Asn Ala Asp Val Gly Arg Leu
            1765                1770                1775

Ile Phe Ser Gly Glu Ala Leu Thr Tyr Lys Asp Ile Val Val Cys Met
            1780                1785                1790

Asp Gly Asp Thr Met Pro Gly Leu Phe Ala Tyr Arg Ala Ala Thr Lys
            1795                1800                1805

Ala Gly Tyr Cys Gly Gly Ala Val Leu Ala Lys Asp Gly Ala Asp Thr
    1810                1815                1820

Phe Ile Val Gly Thr His Ser Ala Gly Gly Asn Gly Val Gly Tyr Cys
1825                1830                1835                1840

Ser Cys Val Ser Arg Ser Met Leu Leu Lys Met Lys Ala His Ile Asp
            1845                1850                1855

Pro Glu Pro His His Glu Gly Leu Ile Val Asp Thr Arg Asp Val Glu
            1860                1865                1870

Glu Arg Val His Val Met Arg Lys Thr Lys Leu Ala Pro Thr Val Ala
    1875                1880                1885

His Gly Val Phe Asn Pro Glu Phe Gly Pro Ala Ala Leu Ser Asn Lys
    1890                1895                1900

Asp Pro Arg Leu Asn Glu Gly Val Val Leu Asp Glu Val Ile Phe Ser
1905                1910                1915                1920

Lys His Lys Gly Asp Thr Lys Met Ser Glu Glu Asp Lys Ala Leu Phe
            1925                1930                1935

Arg Arg Cys Ala Ala Asp Tyr Ala Ser Arg Leu His Ser Val Leu Gly
            1940                1945                1950

Thr Ala Asn Ala Pro Leu Ser Ile Tyr Glu Ala Ile Lys Gly Val Asp
    1955                1960                1965

Gly Leu Asp Ala Met Glu Pro Asp Thr Ala Pro Gly Leu Pro Trp Ala
    1970                1975                1980

Leu Gln Gly Lys Arg Arg Gly Ala Leu Ile Asp Phe Glu Asn Gly Thr
1985                1990                1995                2000

Val Gly Pro Glu Val Glu Ala Ala Leu Lys Leu Met Glu Lys Arg Glu
            2005                2010                2015

Tyr Lys Phe Val Cys Gln Thr Phe Leu Lys Asp Glu Ile Arg Pro Leu
            2020                2025                2030

Glu Lys Val Arg Ala Gly Lys Thr Arg Ile Val Asp Val Leu Pro Val
    2035                2040                2045

Glu His Ile Leu Tyr Thr Arg Met Met Ile Gly Arg Phe Cys Ala Gln
    2050                2055                2060

Met His Ser Asn Asn Gly Pro Gln Ile Gly Ser Ala Val Gly Cys Asn
2065                2070                2075                2080

Pro Asp Val Asp Trp Gln Arg Phe Gly Thr His Phe Ala Gln Tyr Arg
            2085                2090                2095

Asn Val Trp Asp Val Asp Tyr Ser Ala Phe Asp Ala Asn His Cys Ser
            2100                2105                2110

Asp Ala Met Asn Ile Met Phe Glu Glu Val Phe Arg Thr Glu Phe Gly
    2115                2120                2125
```

-continued

```
Phe His Pro Asn Ala Glu Trp Ile Leu Lys Thr Leu Val Asn Thr Glu
   2130                2135                2140

His Ala Tyr Glu Asn Lys Arg Ile Thr Val Gly Gly Gly Met Pro Ser
2145                2150                2155                2160

Gly Cys Ser Ala Thr Ser Ile Ile Asn Thr Ile Leu Asn Asn Ile Tyr
                2165                2170                2175

Val Leu Tyr Ala Leu Arg Arg His Tyr Glu Gly Val Glu Leu Asp Thr
            2180                2185                2190

Tyr Thr Met Ile Ser Tyr Gly Asp Asp Ile Val Val Ala Ser Asp Tyr
        2195                2200                2205

Asp Leu Asp Phe Glu Ala Leu Lys Pro His Phe Lys Ser Leu Gly Gln
   2210                2215                2220

Thr Ile Thr Pro Ala Asp Lys Ser Asp Lys Gly Phe Val Leu Gly His
2225                2230                2235                2240

Ser Ile Thr Asp Val Thr Phe Leu Lys Arg His Phe His Met Asp Tyr
                2245                2250                2255

Gly Thr Gly Phe Tyr Lys Pro Val Met Ala Ser Lys Thr Leu Glu Ala
            2260                2265                2270

Ile Leu Ser Phe Ala Arg Arg Gly Thr Ile Gln Glu Lys Leu Ile Ser
        2275                2280                2285

Val Ala Gly Leu Ala Val His Ser Gly Pro Asp Glu Tyr Arg Arg Leu
   2290                2295                2300

Phe Glu Pro Phe Gln Gly Leu Phe Glu Ile Pro Ser Tyr Arg
2305                2310                2315

<210> SEQ ID NO 25
<211> LENGTH: 2232
<212> TYPE: PRT
<213> ORGANISM: equine rhinovirus 1

<400> SEQUENCE: 25

Met Ala Ala Ser Lys Val Tyr Arg Val Cys Glu Gln Thr Leu Leu Ala
  1               5                  10                  15

Gly Ala Val Arg Met Met Asp Lys Phe Leu Gln Lys Arg Thr Val Phe
             20                  25                  30

Val Pro His Leu Asp Lys Thr Ile Arg Leu Thr Gly Leu His Asn Tyr
         35                  40                  45

Asp Asn Thr Cys Trp Leu Asn Ala Leu Thr Gln Leu Thr Gln Ile Leu
     50                  55                  60

Gly Ile Arg Leu Phe Asp Glu His Phe Gly Asn Arg Gly Leu Phe Thr
 65                  70                  75                  80

Arg Lys Thr Ile Asp Trp Val Ser Asp Gln Thr Gly Ile Lys Asp Leu
                 85                  90                  95

Lys Ser Gly Ala Pro Pro Leu Val Val Val Tyr Lys Leu Trp Gln His
            100                 105                 110

Gly His Leu Asp Val Gly Thr Met Glu Lys Pro Arg Ser Ile Thr Leu
        115                 120                 125

Trp Ser Gly Pro Lys Val Cys Leu Ser Asp Phe Trp Ala Cys Val Ser
    130                 135                 140

Ala Lys Pro Gly His Ala Val Phe Tyr Leu Leu Thr Ser Glu Gly Trp
145                 150                 155                 160

Ile Cys Val Asp Asp Lys Lys Ile Tyr Pro Glu Thr Pro Lys Thr Glu
                165                 170                 175

Asp Val Leu Val Phe Ala Pro Tyr Asp Phe Glu Ser Leu Gly Lys Asp
            180                 185                 190
```

-continued

```
Pro Pro Lys Leu His Gln Arg Tyr Glu Lys Ala Phe Glu Leu Ser Gly
        195                 200                 205
Gly Gly Thr Ser Thr Pro Thr Thr Gly Asn Gln Asn Met Ser Gly Asn
        210                 215                 220
Ser Gly Ser Ile Val Gln Asn Phe Tyr Met Gln Gln Tyr Gln Asn Ser
225                 230                 235                 240
Ile Asp Ala Asp Leu Gly Asp Asn Val Ile Ser Pro Glu Gly Gln Gly
                245                 250                 255
Ser Asn Thr Ser Ser Ser Thr Ser Ser Ser Gln Ser Ser Gly Leu Gly
                260                 265                 270
Gly Trp Phe Ser Ser Leu Leu Asn Leu Gly Thr Lys Leu Leu Ala Asp
            275                 280                 285
Lys Lys Thr Glu Glu Thr Thr Asn Ile Glu Asp Arg Ile Glu Thr Thr
        290                 295                 300
Val Val Gly Val Thr Ile Ile Asn Ser Gln Gly Ser Val Gly Thr Thr
305                 310                 315                 320
Tyr Cys Tyr Ser Lys Pro Asp Gly Arg Pro Ser Thr Val Ser Asp
                325                 330                 335
Pro Val Thr Arg Leu Gly Pro Thr Leu Ser Arg His Tyr Thr Phe Lys
                340                 345                 350
Val Gly Glu Trp Pro His Ser Gln Ser His Gly His Ala Trp Ile Cys
            355                 360                 365
Pro Leu Pro Gly Asp Lys Leu Lys Lys Met Gly Ser Phe His Glu Val
        370                 375                 380
Val Lys Ala His His Leu Val Lys Asn Gly Trp Asp Val Val Val Gln
385                 390                 395                 400
Val Asn Pro Ser Phe Ala His Ser Gly Pro Leu Cys Val Ala Ala Val
                405                 410                 415
Pro Glu Tyr Glu His Thr His Glu Lys Ala Leu Lys Trp Ser Glu Leu
                420                 425                 430
Glu Glu Pro Ala Tyr Thr Tyr Gln Gln Leu Ser Val Phe Pro His Gln
            435                 440                 445
Leu Leu Asn Leu Arg Thr Asn Ser Ser Val His Leu Val Met Pro Tyr
        450                 455                 460
Ile Gly Pro Gly Gln Pro Thr Asn Leu Thr Leu His Asn Pro Trp Thr
465                 470                 475                 480
Ile Val Ile Leu Ile Leu Ser Glu Leu Thr Gly Pro Gly Gln Thr Val
                485                 490                 495
Pro Val Thr Met Ser Val Ala Pro Ile Asp Ala Met Val Asn Gly Pro
            500                 505                 510
Leu Pro Asn Pro Glu Ala Pro Ile Arg Val Val Ser Val Pro Glu Ser
        515                 520                 525
Asp Ser Phe Met Ser Ser Val Pro Asp Asn Ser Thr Pro Leu Tyr Pro
    530                 535                 540
Lys Val Val Pro Pro Arg Gln Val Pro Gly Arg Phe Thr Asn Phe
545                 550                 555                 560
Ile Asp Val Ala Lys Gln Thr Tyr Ser Phe Cys Ser Ile Ser Gly Lys
                565                 570                 575
Pro Tyr Phe Glu Val Thr Asn Thr Ser Gly Asp Glu Pro Leu Phe Gln
                580                 585                 590
Met Asp Val Ser Leu Ser Ala Ala Glu Leu His Gly Thr Tyr Val Ala
        595                 600                 605
```

-continued

```
Ser Leu Ser Ser Phe Phe Ala Gln Tyr Arg Gly Ser Leu Asn Phe Asn
    610                 615                 620

Phe Ile Phe Thr Gly Ala Ala Thr Lys Ala Lys Phe Leu Val Ala
625                 630                 635                 640

Phe Val Pro Pro His Ser Ala Pro Lys Thr Arg Asp Glu Ala Met
                    645                 650                 655

Ala Cys Ile His Ala Val Trp Asp Val Gly Leu Asn Ser Ala Phe Ser
                660                 665                 670

Phe Asn Val Pro Tyr Pro Ser Pro Ala Asp Phe Met Ala Val Tyr Ser
            675                 680                 685

Ala Glu Arg Thr Val Val Asn Val Ser Gly Trp Leu Gln Val Tyr Ala
    690                 695                 700

Leu Thr Ala Leu Thr Ser Thr Asp Ile Ala Val Asn Ser Lys Gly Arg
705                 710                 715                 720

Val Leu Val Ala Val Ser Ala Gly Pro Asp Phe Ser Leu Arg His Pro
                    725                 730                 735

Ala Asp Leu Pro Asp Lys Gln Val Thr Asn Val Gly Glu Asp Gly Glu
                740                 745                 750

Pro Gly Glu Thr Glu Pro Arg His Ala Leu Ser Pro Val Asp Met His
            755                 760                 765

Val His Thr Asp Val Ser Phe Leu Leu Asp Arg Phe Phe Asp Val Glu
    770                 775                 780

Thr Leu Glu Leu Ser Asn Leu Thr Gly Ser Pro Ala Thr His Val Leu
785                 790                 795                 800

Asp Pro Phe Gly Ser Thr Ala Gln Leu Ala Trp Ala Arg Leu Leu Asn
                    805                 810                 815

Thr Cys Thr Tyr Phe Phe Ser Asp Leu Glu Leu Ser Ile Gln Phe Lys
                820                 825                 830

Phe Thr Thr Thr Pro Ser Ser Val Gly Glu Gly Phe Val Trp Val Lys
            835                 840                 845

Trp Leu Pro Val Gly Ala Pro Thr Lys Thr Thr Asp Ala Trp Gln Leu
    850                 855                 860

Glu Gly Gly Gly Asn Ser Val Arg Ile Gln Lys Leu Ala Val Ala Gly
865                 870                 875                 880

Met Cys Pro Thr Val Val Phe Lys Ile Ala Gly Ser Arg Ser Gln Ala
                    885                 890                 895

Cys Ala Ser Ala Leu Pro Tyr Thr Ser Met Trp Arg Val Val Pro Val
                900                 905                 910

Phe Tyr Asn Gly Trp Gly Ala Pro Thr Lys Glu Lys Ala Thr Tyr Asn
            915                 920                 925

Trp Leu Pro Gly Ala His Phe Gly Ser Ile Leu Leu Thr Ser Asp Ala
    930                 935                 940

His Asp Lys Gly Gly Cys Tyr Leu Arg Tyr Ala Phe Arg Ala Pro Ala
945                 950                 955                 960

Met Tyr Cys Pro Arg Pro Ile Pro Pro Ala Phe Thr Arg Pro Ala Asp
                    965                 970                 975

Lys Thr Arg His Lys Phe Pro Thr Asn Ile Asn Lys Gln Cys Thr Asn
                980                 985                 990

Tyr Ser Leu Leu Lys Leu Ala Gly Asp Val Glu Ser Asn Pro Gly Pro
            995                 1000                1005

Thr Ile Phe Ser Lys Ala Ser Ala Asp Leu Asn Ala Leu Ser Thr Ser
    1010                1015                1020
```

-continued

```
Leu Gly Glu Leu Thr Gly Met Leu Lys Asp Leu Lys Ala Lys Ala Glu
1025                1030                1035                1040

Thr Tyr Ser Pro Phe Tyr Lys Met Ala Lys Met Leu Phe Lys Leu Ala
            1045                1050                1055

Thr Leu Ala Val Ala Ala Met Arg Thr Lys Asp Pro Val Val Val
        1060                1065                1070

Met Leu Ile Ala Asp Phe Gly Leu Glu Val Phe Asp Thr Gly Phe Phe
        1075                1080                1085

Phe Ser Tyr Phe Gln Glu Lys Leu Gln Pro Tyr Met Lys Thr Ile Pro
    1090                1095                1100

Gly Lys Ile Ser Asp Leu Val Thr Asp Ala Ala Thr Ala Ala Ala Gln
1105                1110                1115                1120

Ile Pro Lys Gly Val Tyr Ser Phe Val Ser Ser Phe Glu Thr Pro
            1125                1130                1135

Glu Gly Val Val Glu Lys Gln Val Ser Leu Arg Thr Val Asn Asp Ile
        1140                1145                1150

Phe Ala Leu Leu Lys Asn Ser Asp Trp Phe Ile Lys Thr Leu Val Ala
1155                1160                1165

Leu Lys Lys Trp Leu Thr Ser Trp Phe Ala Gln Glu Gln Gln Ala Asp
    1170                1175                1180

Asp Ala Leu Tyr Ser Glu Leu Glu Lys Tyr Pro Leu Tyr Lys Leu Lys
1185                1190                1195                1200

Leu Lys Glu Pro Asp Thr Gln Glu Glu Ala Arg Gln Trp Phe Lys Asp
            1205                1210                1215

Met Gln Gln Arg Ala Leu Ala Val Lys Asp Lys Gly Leu Phe Ser Leu
        1220                1225                1230

Leu Gln Ile Pro Leu Val Asn Leu Pro Gln Ser Arg Pro Glu Pro Val
    1235                1240                1245

Val Cys Val Leu Arg Gly Ala Ser Gly Gln Gly Lys Ser Tyr Leu Ala
1250                1255                1260

Asn Leu Met Ala Gln Ala Ile Ser Leu Leu Leu Val Gly Lys Gln Asp
1265                1270                1275                1280

Ser Val Trp Ser Cys Pro Pro Asp Pro Thr Tyr Phe Asp Gly Tyr Asn
            1285                1290                1295

Gly Gln Ala Val Val Ile Met Asp Ala Leu Gly Gln Asp Pro Asn Gly
        1300                1305                1310

Ala Asp Phe Lys Tyr Phe Cys Gln Met Val Ser Thr Thr Ala Phe Val
        1315                1320                1325

Pro Pro Met Ala His Leu Asp Asp Lys Gly Ile Pro Phe Thr Ser Pro
    1330                1335                1340

Val Val Ile Cys Thr Thr Asn Leu His Ser Ser Phe Thr Pro Ile Thr
1345                1350                1355                1360

Val Ser Cys Pro Glu Ala Leu Lys Arg Arg Phe Arg Phe Asp Val Thr
            1365                1370                1375

Val Ser Ala Lys Pro Gly Phe Val Arg Thr Val Gly Ser Asn Gln Leu
        1380                1385                1390

Leu Asn Leu Pro Leu Ala Leu Lys Pro Ala Gly Leu Pro Pro His Pro
    1395                1400                1405

Ile Phe Glu Asn Asp Met Pro Ile Ile Asn Gly Gln Ala Val Lys Leu
    1410                1415                1420

Ala Leu Ser Gly Gly Glu Val Thr Ala Phe Glu Leu Ile Glu Met Ile
1425                1430                1435                1440
```

```
Leu Ser Glu Val Gln Asn Arg Gln Asp Thr His Lys Met Pro Ile Phe
            1445                1450                1455

Lys Gln Ser Trp Ser Asp Leu Phe Arg Lys Cys Thr Thr Asp Glu Glu
            1460                1465                1470

Gln Lys Met Leu Gln Phe Leu Ile Asp Asn Lys Asp Ser Glu Ile Leu
            1475                1480                1485

Arg Ala Phe Val Ser Glu Arg Ser Ile Leu Leu His Glu Glu Tyr Leu
            1490                1495                1500

Lys Trp Glu Ser Tyr Met Thr Arg Arg Ala Lys Phe His Arg Leu Ala
1505                1510                1515                1520

Ala Asp Phe Ala Met Phe Leu Ser Ile Leu Thr Ser Leu Ile Val Ile
            1525                1530                1535

Phe Cys Leu Val Tyr Ser Met Tyr Gln Leu Phe Lys Thr Pro Asp Glu
            1540                1545                1550

Gln Ser Ala Tyr Asp Pro Ser Thr Lys Pro Lys Pro Lys Thr Gln Glu
            1555                1560                1565

Val Lys Thr Leu Lys Ile Arg Thr Glu Thr Gly Val Pro Ala Thr Asp
            1570                1575                1580

Leu Gln Gln Ser Ile Met Lys Asn Val Gln Pro Ile Glu Leu Tyr Leu
1585                1590                1595                1600

Asp Asn Glu Leu Val Thr Asp Cys Ser Ala Leu Gly Val Tyr Asp Asn
            1605                1610                1615

Ser Tyr Leu Val Pro Leu His Leu Phe Glu Phe Asp Phe Asp Thr Ile
            1620                1625                1630

Val Leu Gly Gly Arg His Tyr Lys Lys Ala Glu Cys Glu Lys Val Glu
            1635                1640                1645

Phe Glu Leu Glu Val Asn Gly Asp Val Val Ser Ser Asp Ala Cys Leu
1650                1655                1660

Leu Arg Val Ser Ser Gly Pro Lys Val Arg Asn Ile Val His Leu Phe
1665                1670                1675                1680

Thr Asn Glu Ile Glu Leu Lys Lys Met Thr Gln Val Thr Gly Ile Met
            1685                1690                1695

Asn Ser Pro His Gln Ala Arg Thr Val Phe Phe Gly Ser Phe Leu Thr
            1700                1705                1710

Val Arg Lys Ser Ile Leu Thr Ser Asp Gly Thr Val Met Pro Asn Val
            1715                1720                1725

Leu Ser Tyr Ala Ala Gln Thr Ser Arg Gly Tyr Cys Gly Ala Ala Ile
            1730                1735                1740

Val Ala Gly Ser Pro Ala Arg Ile Ile Gly Ile His Ser Ala Gly Thr
1745                1750                1755                1760

Gly Ser Val Ala Phe Cys Ser Leu Val Ser Arg Asp Ala Leu Glu Gln
            1765                1770                1775

Leu Trp Pro Gln Lys Gln Gly Asn Val Ser Arg Leu Asp Asp Asp Val
            1780                1785                1790

Arg Val Ser Val Pro Arg Arg Ser Lys Leu Val Lys Ser Leu Ala Tyr
            1795                1800                1805

Pro Ile Phe Lys Pro Asp Tyr Gly Pro Ala Pro Leu Ser Gln Phe Asp
            1810                1815                1820

Lys Arg Leu Ser Asp Gly Val Lys Leu Asp Glu Val Val Phe Ala Lys
1825                1830                1835                1840
```

-continued

His Thr Gly Asp Lys Glu Ile Ser Ala Gln Asp Gln Lys Trp Leu Leu
            1845                1850                1855

Arg Ala Ala His Val Tyr Ala Gln Lys Val Phe Ser Arg Ile Gly Phe
            1860                1865                1870

Asp Asn Gln Ala Leu Thr Glu Lys Glu Ala Ile Cys Gly Ile Pro Gly
            1875                1880                1885

Leu Asp Lys Met Glu Gln Asp Thr Ala Pro Gly Leu Pro Tyr Ala Gln
    1890                1895                1900

Gln Asn Lys Arg Arg Lys Asp Ile Cys Asp Phe Glu Glu Gly Arg Leu
1905                1910                1915                1920

Lys Gly Ala Glu Leu Gln Lys Asp Arg Phe Met Ala Gly Asp Tyr Ser
            1925                1930                1935

Asn Leu Val Tyr Gln Ser Phe Leu Lys Asp Glu Ile Arg Pro Leu Glu
            1940                1945                1950

Lys Val Arg Ala Gly Lys Thr Arg Leu Ile Asp Val Pro Pro Met Pro
            1955                1960                1965

His Val Val Val Gly Arg Gln Leu Leu Gly Arg Phe Val Ala Lys Phe
        1970                1975                1980

His Glu Ala Asn Gly Phe Asp Ile Gly Ser Ala Ile Gly Cys Asp Pro
1985                1990                1995                2000

Asp Val Asp Trp Thr Arg Phe Gly Leu Glu Leu Glu Arg Phe Arg Tyr
            2005                2010                2015

Val Tyr Ala Cys Asp Tyr Ser Arg Phe Asp Ala Asn His Ala Ala Asp
            2020                2025                2030

Ala Met Arg Val Val Leu Asn Tyr Phe Phe Ser Glu Asp His Gly Phe
        2035                2040                2045

Asp Pro Gly Val Pro Ala Phe Ile Glu Ser Leu Val Asp Ser Val His
            2050                2055                2060

Ala Tyr Glu Glu Lys Arg Tyr Asn Ile Tyr Gly Gly Leu Pro Ser Gly
2065                2070                2075                2080

Cys Ser Cys Thr Ser Ile Leu Asn Thr Ile Leu Asn Asn Val Tyr Ile
            2085                2090                2095

Leu Ala Ala Met Met Lys Ala Tyr Glu Asn Phe Glu Pro Asp Asp Ile
            2100                2105                2110

Gln Val Ile Cys Tyr Gly Asp Asp Cys Leu Ile Ala Ser Asp Phe Glu
        2115                2120                2125

Ile Asp Phe Gln Gln Leu Val Pro Val Phe Ser Ser Phe Gly Gln Val
2130                2135                2140

Ile Thr Thr Ala Asp Lys Thr Asp Phe Lys Leu Thr Thr Leu Ser
2145                2150                2155                2160

Glu Val Thr Phe Leu Lys Arg Ala Phe Val Leu Thr Ala Phe Tyr Lys
            2165                2170                2175

Pro Val Met Asp Val Lys Thr Leu Glu Ala Ile Leu Ser Phe Val Arg
        2180                2185                2190

Pro Gly Thr Gln Ala Glu Lys Leu Leu Ser Val Ala Gln Leu Ala Gly
        2195                2200                2205

His Cys Glu Pro Glu Gln Tyr Glu Arg Leu Phe Glu Pro Phe Ala Gly
    2210                2215                2220

Met Tyr Phe Val Pro Thr Trp Arg
2225                2230

EQUINE RHINOVIRUS 1 PROTEINS

INTRODUCTION TO INVENTION

This invention relates to the equine rhinovirus 1 (ERhV1) which has been sequenced and characterized. In particular, the invention relates to nucleotide and protein sequences of ERhV1 and a range of clinical and diagnostic products derived from ERhV1.

BACKGROUND OF INVENTION

Equine rhinovirus 1 (ERhV1) was first isolated from horses in the United Kingdom and subsequently from horses in mainland Europe, the USA and Australia. Most isolates were from the nasopharynx of horses with an acute, febrile respiratory disease. Virions had the characteristic size and morphology of picornaviruses and were acid-labile. Two other serologically distinct, acid-labile picornaviruses, ERhV2 and ERhV3, have also been isolated from horses.

Considerable uncertainty has surrounded the classification of ERhV1. Physicochemical studies have shown that the nucleic acid density and base composition of ERhV1 differ from those of rhinoviruses. In contrast to rhinoviruses, ERhV1 has a broad host-cell range in vitro and in vivo and there is no evidence of extensive antigenic variation. Infection of horses with ERhV1 causes a disease characterized by an acute febrile respiratory disease accompanied by anemia, fecal and urine shedding and viral persistence. The signs of systemic infection and persistence are not characteristic of rhinovirus infections in other species. The known host range of ERhV1 is broad and includes rabbits, guinea pigs, monkeys and humans, although in these species the virus does not appear to spread horizontally. There is both experimental and epidemiological evidence of ERhV1 infection of humans. A human volunteer inoculated intranasally with ERhV1 developed severe pharyngitis, lymphadenitis, fever and viremia, and high ERhV1 antibody titers were found in the sera of 3 of 12 stable workers whereas no ERhV1 antibody was found in the sera of 159 non-stable workers.

In order to clarify the taxonomic status of ERhV1, a detailed study was undertaken to determine the nucleotide and amino acid sequence of ERhV1. The resultant studies provided the complete nucleotide sequence of the gene encoding the ERhV1 polyprotein and the 3'-nontranslated region (NTR) as well as part of the nucleotide sequence of the 5'NTR. The amino acid sequence of the various ERhV1 proteins was deduced from the nucleotide sequence.

The analysis of the nucleotide sequence of ERhV1 confirmed previous studies which indicated that many properties of ERhV1 are not consistent with those of other members of the genus Rhinovirus. Indeed many of the physicochemical and biological properties of ERhV1 have suggested ERhV1 is more closely related to foot-and-mouth disease virus (FMDV) the sole member of the Alpthovirus genus. In addition to the overall sequence similarity, several features of the ERhV1 genome are similar to those of FMDV. The ERhV1 L protein is most similar to its counterpart in aphthoviruses in both length, 207 amino acids in ERhV1 and 201 in FMDV, and in amino acid sequence identity. In aphthoviruses, the L protein catalyses its own cleavage from the polyprotein, and mediates cleavage of the p220 component of the cap-binding complex leading to inhibition of translation of capped mRNAs. Cardiovirus L proteins are only 67–76 amino acids long and are not auto catalytic. In contrast to the cardioviruses, aphthoviruses utilize two distinct initiation codons, which results in different forms of the L protein, Lab and Lb, differing from each other by 28 amino acids at their N-termini.

The second initiation codon occurs in a more favourable context, which is presumably the reason why Lb, the smaller of the two proteins, is the predominant species. Thus far, differences in the function of the two FMDV L proteins have not been detected. ERhV1 also possesses a second ATG, 63 bases downstream from the first optimal ATG, which is also present in a context optimal for initiation of translation. Translation from this ATG would result in an L protein with 21 fewer amino acids at its N-terminus. Therefore, it is probable that ERhV1 possesses a second species of L protein, similar to the FMDV Lb protein. If so, the reason for the existence and conservation of two forms of the L protein in ERhV1 and FMDV is an intriguing question. Curiously, ERhV1 has tandemly repeated ATG codons at each of the possible initiation sites, where the first ATG in each case does not occur in a context optimal for translation. The role of these ATGs may be to ensure that translation is initiated from both possible initiation sites.

The 2A protease is only 16 amino acids in length in both FVDV and ERhV1, compared to 142–149 amino acids in other picornaviruses. In FMDV 2A protease cleaves at its C-terminus but, unlike the 2A protease of other picornaviruses, appears not to have a role in shut down of host cell macromolecular synthesis. The high degree of conservation of the FMDV and ERhV1 2A proteins is intriguing and suggests an important role for this protein in the diseases produced by these viruses.

It may be expected that the tree derived from the complete polyprotein coding sequence would provide the most representative view of the taxonomic status of ERhV1 by reducing any bias imparted by using restricted parts of the genome with highly variable evolutionary rates. However, such analysis is restricted because there are only a few complete polyprotein sequences available. The polymerase genes are the most conserved genes in positive strand RNA viruses and they have been used to construct a taxonomy, and to predict the ancient roots, of these viruses. In contrast to the polymerase gene, the VP1 gene encodes the major antigenic determinants of the virus and evolves more rapidly than other regions in the genome. The diversity of VP1 regions make them useful for the study of closely related picornaviruses. Thus, trees based on the polymerase and VP1 genes presumably reflect the extremes of evolutionary rates from which the taxonomic status and evolutionary origin of ERhV1 could be identified. The ERhV1 VP1 amino acid sequence was more similar to FMDV than to any other sequence in the data base; this was true even when representative segments across the entire sequence were separately analysed.

Therefore, we consider that the difference in the topology of the VP1, compared to the other two trees, is most unlikely to be a consequence of genetic recombination. The topographic differences between the three ERhV1 trees compared to those of aphthoviruses, particularly the VP1 derived trees, as well as the presence of only one VPg gene in ERhV1 genome, leads us to conclude that ERhV1 is probably a member of a distinct genus proposed to be called Equirhinovirus.

The reassessment of the taxonomic status of ERhV1 focuses on a requirement to reassess the biology of the virus particularly with respect to the nature of clinical disease as well as means for control by vaccination and improved methods of diagnosis. For example, cardioviruses and aphthoviruses cause viremic infections accompanied by myocarditis. Clinical disease caused by ERhV1 is generally considered to be confined to the respiratory tract even though there is a viremia and the virus is shed in faeces and urine. Whether ERhV1 infection produces systemic disease similar to that observed in aphthovirus or cardiovirus infections, including the production of myocarditis, needs to be investigated. There is serological evidence that the incidence of ERhV1 infection is as high as 50% in some horse populations however, the number of reported isolations of ERhV1 is very small. We have clear evidence that primary isolation of the virus from clinical specimens is known to be difficult, suggesting that the true incidence of ERhV1 disease is much greater than reported.

The determination of the complete nucleotide sequence of ERhV1 polyprotein has important practical applications in developing novel methods for the diagnosis and control of ERhV disease in horses and other species.

OBJECT AND STATEMENT OF INVENTION

In one aspect, the invention provides a substantially pure nucleotide sequence for ERhV1 being:

a substantially pure nucleotide sequence for ERhV1 (SEQ ID NO:1) being:

```
CCGTCAAGCC CGTTGCCTGT ATAGCCAGGT AACCGGACAG CGGCTTGCTG GATTTTCCCG  -375
GTGCCATTGC TCTGGATGGT GTCACCAAGC TGACAAATGC GGAGTGAACC TCACAAAGCG  -315
ACACGCCTGT GGTAGCGCTG CCCAAAAGGG AGCGGAACTC CCCGCCGAGG CGGTCCTCTC  -255
TGGCCAAAAG CCCAGCGTTG ATAGCGCCTT TTGGGATGCA GGAACCCCAC CTGCCAGGTG  -195
TGAAGTGGAG TGAGCGGATC TCCAATTTGG TCTGTTCTGA ACTACACCAT TTACTGCTGT  -135
GAAGAATGCC CTGGAGGCAA GCTGGTTACA GCCCTGACCA GGCCCTGCCC GTGACTCTCG   -75
ACCGGCGCAG GGTCAAAAAT TGTCTAAGCA GCAGCAGGAA CGCGGGAGCG TTTCTTTTCC   -15
TTTTGTACTG ACATGATGGC GGCGTCTAAG GTGTATAGAG TTTGCGAGCA GACTCTGCTG    45
GCAGGTGCCG TTCGCATGAT GGACAAATTC TTGCAAAAGA GAACTGTTTT TGTCCCCCAT   105
CTTGACAAAA CAATTCGTTT GACTGGACTC CACAATTATG ACAATACTTG CTGGTTGAAT   165
GCCTTGACAC AACTGACACA GATTCTTGGA ATTCGGCTTT TTGATGAACA CTTCGGCAAT   225
AGAGGTCTGT TCACTCGGAA AACAATTGAT TGGGTGAGTG ACCAGACTGG TATAAAAGAT   265
CTAAAATCAG GAGCACCGCC ACTCGTGGTG GTGTACAAAC TGTGGCAACA TGGACACTTG   345
GATGTCGGTA CGATGGAGAA ACCCCGGTCG ATTACTCTAT GGTCTGGCCC CAAAGTGTGT   405
CTTTCTGATT TCTGGGCCTG TGTTTCGGCA AAACCGGGAC ATGCAGTATT CTACCTTCTC   463
ACAAGCGAGG GTTGGATCTG TGTTGATGAC AAGAAAATAT ACCCAGAAAC ACCCAAAACA   525
GAGGATGTAC TTGTTTTTGC GCCCTATGAC TTTGAGTCAC TGGGCAAGGA CCCACCAAAG   585
CTACACCAGA GATATGAAAA AGCATTTGAG CTCAGTGGCG GAGGTACATC CACTCCAACA   645
ACTGGCAACC AAAACATGTC CGGAAACAGT GGTTCAATTG TTCAAAATTT TTACATGCAA   705
CAGTACCAGA ATTCAATTGA CGCAGACCTG GGAGACAATG TGATTAGCCC TGAAGGCCAG   765
GGCAGCAACA CTAGTAGTTC AACCTCATCA AGCCAATCCT CTGGCTTGGG CGGGTGGTTC   825
TCTAGTTTGC TGAACCTTGG AACAAAACTA CTGGCTGACA AGAAGACAGA AGAGACTACA   885
AACATTGAAG ACAGAATTGA AACAACAGTG GTTGGAGTCA CTATTATTAA TTCACAAGGA   945
TCTGTTGGAA CAACCTACTG TTACTCCAAA CCGGATGGTA GACCACCATC CACAGTGTCA  1005
GACCCAGTTA CCAGACTTGG ACCCACGCTT TCCAGGCACT ACACATTTAA GGTAGGTGAG  1065
TGGCCCCATT CTCAATCACA TGGTCACGCA TGGATCTGTC CGTTGCCAGG TGACAAACTC  1125
AAGAAGATGG GCAGTTTTCA TGAGGTTGTC AAAGCCCACC ACCTGGTCAA GAACGGCTGG  1185
GATGTGGTTG TGCAGGTGAA TCCCTCATTT GCTCACTCCG GGCCGCTGTG TGTAGCAGCA  1245
GTGCCGGAGT ACGAACACAC ACATGAGAAA GCACTCAAGT GGTCTGAGCT TGAGGAACCA  1305
GCTTACACAT ACCAACAACT TTCAGTTTTT CCCCACCAGT TGCTAAATTT GAGGACAAAT  1365
TCATCAGTGC ATTTGGTGAT GCCCTACATT GGGCCAGGCC AACCAACAAA TCTGACTTTG  1425
CACAACCCGT GGACCATTGT TATTTTAATT TTGTCTGAAT TGACAGGACC TGGCCAAACT  1485
GTGCCTGTGA CCATGTCGGT GGCTCCCATC GATGCAATGG TTAATGGGCC TCTTCCAAAT  1545
```

-continued

```
CCAGAGGCAC CGATTAGAGT GGTGTCTGTG CCTGAATCAG ATTCTTTTAT GTCTTCAGTA    1605

CCTGATAATT CGACTCCACT ATACCCCAAG GTTGTGGTCC CACCGCGCCA AGTTCCTGGC    1665

CGGTTTACAA ATTTCATTGA TGTGGCAAAA CAGACATATT CATTTTGTTC CATTTCTGGA    1725

AAACCTTATT TTGAGGTTAC CAACACCTCT GGGGACGAGC CACTGTTTCA GATGGATGTG    1765

TCGCTCAGTG CGGCAGAGCT ACATGGCACT TACGTAGCTA GTTTGTCATC ATTTTTTGCA    1845

CAGTACAGAG GCTCACTTAA TTTCAACTTT ATTTTCACTG GTGCAGCAGC CACTAAGGCA    1905

AAGTTTCTGG TTGCTTTTGT GCCTCCCCAC AGTGCAGCGC CCAAAACGCG CGATGAAGCA    1965

ATGGCGTGCA TCCATGCCGT GTGGGATGTT GGCTTGAACT CAGCTTTTTC TTTTAATGTA    2025

CCTTATCCCT CCCCTGCTGA CTTCATGGCC GTTTATTCTG CGGAACGGAC GGTTGTGAAT    2085

GTCTCTGGAT GGCTTCAAGT TTATGCACTA ACAGCTCTAA CTTCAACTGA CATTGCCGTG    2145

AACAGTAAAG GCCGTGTGCT GGTTGCTGTT TCCGCCGGCC CAGACTTCTC CCTTCGTCAC    2205

CCGGCGGACC TGCCCGACAA GCAGGTTACC AATGTGGGAG AGGATGGTGA ACCCGGTGAG    2265

ACAGAGCCTC GTCATGCTTT GTCACCCGTG GACATGCACG TGCACACAGA TGTCAGTTTC    2325

TTGCTTGACC GGTTCTTTGA TGTTGAGACA CTTGAGCTTT CAAATTTGAC AGGTTCTCCT    2385

GCCACACATG TTCTGGATCC GTTTGGCTCG ACTGCCCAAC TGGCTTGGGC ACGTCTGCTA    2445

AACACTTGCA CCTACTTCTT TTCTGATTTG GAATTGTCAA TCCAGTTTAA ATTTACCACC    2505

ACTCCGTCCT CTGTTGGAGA GGGCTTTGTG TGGGTGAAGT GGCTCCCTGT TGGAGCACCA    2565

ACCAAGACCA CAGATGCTTG GCAGTTAGAA GGAGGTGGAA ATTCAGTTAG AATTCAAAAA    2625

TTGGCCGTTG CAGGGATGTG CCCCACTGTT GTGTTCAAGA TTGCAGGCTC CCGTTCACAA    2685

GCCTGTGCTT CAGCGTTGCC ATATACATCA ATGTGGCGTG TTGTGCCAGT CTTTTACAAT    2745

GGCTGGGGTG CACCTACCAA AGAAAAGGCA ACCTACAATT GGCTTCCTGG TGCACACTTT    2605

GGTTCCATCT TGCTGACTTC TGATGCGCAT GATAAAGGAG GGTGCTACTT GCGGTATGCT    2865

TTCCGCGCGC CAGCGATGTA TTGCCCTCGA CCCATTCCGC CGGCTTTTAC GCGTCCAGCG    2925

GACAAAACCA GACATAAATT TCCCACTAAC ATCAACAAAC AGTGTACTAA TTACTCTCTC    2985

CTCAAATTGG CTGGAGATGT TGAGAGCAAC CCTGGCCCCA CTATTTTTTC CAAAGCATCA    3045

GCAGACCTGA ATGCCTTGTC AACGTCGCTA GGTGAATTGA CTGGCATGCT AAAAGATCTT    3105

AAAGCCAAGG CAGAAACTTA TTCCCCGTTT TACAAAATGG CCAAAATGCT TTTCAAACTT    3165

GCAACACTAG CTGTGGCAGC TATGAGGACA AAGGACCCAG TAGTGGTGGT TATGTTGATT    3225

GCTGATTTCG GATTGGAGGT CTTTGACACT GGGTTTTTCT TTTCCTACTT TCAAGAGAAG    3295

TTGCAGCCTT ATATGAAAAC TATTCCTGGT AAGATTTCTG ATTTGGTCAC TGATGCGGCT    3345

ACGGCTGCCG CCCAAATTCC AAAGGGAGTG TATTCTTTTG TGTCGTCATT TTTCGAAACG    3405

CCTGAAGGAG TGGTTGAGAA GCAGGTGTCT CTTCGGACAG TGAATGACAT ATTTGCTTTG    3465

CTTAAAAATT CTGATTGGTT CATAAAGACT CTTGTTGCCC TCAAGAAATG GCTGACATCC    3525

TGGTTTGCTC AAGAACAACA GGCAGATGAT GCGCTCTATT CAGAATTGGA AAAATATCCC    3565

TTGTACAAGT TAAAATTGAA GGAACCTGAT ACTCAAGAGG AAGCGCGCCA GTGGTTTAAA    3645

GACATGCAGC AGCGTGCTCT CGCTGTGAAG GACAAAGGTC TCTTTTCCCT CCTGCAAATT    3705

CCATTAGTTA ACTTGCCCCA GAGCCGTCCA GAGCCCGTTG TATGCGTCCT TCGGGGCGCA    3765

TCAGGGCAAG GCAAATCTTA TTTGGCAAAT CTGATGGCTC AAGCAATTTC GCTTCTCTTG    3825

GTTGGCAAGC AGGACAGTGT GTGGAGTTGT CCTCCTGACC CCACATATTT TGATGGCTAT    3885

AACGGACAGG CTGTGGTGAT TATGGATGCA TTGGGCCAGG ATCCGAATGG TGCTGACTTT    3945
```

-continued

```
AAATATTTTT GCCAGATGGT CTCTACAACA GCTTTTGTAC CACCTATGGC CCATTTGGAT    4005

GATAAAGGCA TTCCATTTAC TTCTCCTGTT GTTATTTGTA CTACAAATTT GCATTCATCT    4065

TTTACCCCTA TTACTGTTTC TTGTCCTGAA GCTCTTAAGA GGAGGTTTCG GTTTGATGTG    4125

ACGGTGTCCG CTAAACCGGG CTTTGTGCGC ACTGTTGGTT CAAACCAGCT TTTGAATCTC    4195

CCACTTGCTC TTAAGCCAGC TGGTCTTCCC CCACACCCTA TCTTTGAAAA TGACATGCCC    4245

ATTATAAATG GGCAGGCTGT TAAATTGGCT CTTTCTGGTG GAGAAGTGAC AGCTTTTGAG    4305

CTTATTGAGA TGATACTGTC AGAAGTTCAA AACAGACAAG ACACACACAA AATGCCCATT    4365

TTTAAACAAT CATGGTCTGA TTTGTTCAGA AAGTGTACAA CTGATGAGGA ACAGAAAATG    4425

TTGCAGTTTT TAATTGACAA TAAAGATTCA GAAATTCTCA GGGCGTTTGT TTCAGAACGC    4485

TCCATTTTAC TACATGAAGA GTATCTTAAA TGGGAGTCAT ATATGACCAG AGAGCCAAG     4545

TTTCACCGCC TGGCTGCTGA TTTTGCTATG TTTCTATCCA TTCTTACTTC ACTGATTGTT    4605

ATTTTTTGTT TAGTTTATTC TATGTATCAA CTTTTTAAGA CCCCTGACGA GCAATCAGCT    4665

TATGATCCTT CAACTAAGCC AAAACCAAAG ACCCAGGAAG TGAAAACACT GAAGATTAGG    4725

ACTGAGACTG GTGTACCAGC AACTGACTTG CAACAATCCA TCATCAAAAA TGTTCAGCCA    4785

ATTGAGCTTT ACCTTGACAA TGAATTGGTT ACTGACTGCT CTGCCTTGGG TGTTTATGAC    4845

AATTCATATT TGGTGCCCCT TCATTTGTTT GAATTTGATT TTGATACCAT TGTGCTTGGT    4905

GGACGTCATT ACAAGAAAGC TGAGTGTGAG AAGGTAGAGT TTGAGCTTGA AGTGAATGGA    4965

GACGTGGTGT CATCAGATGC GTGTCTACTT CGAGTGTCAT CGGGGCCTAA AGTTAGAAAT    5025

ATTGTTCATC TTTTTACAAA TGAAATTGAA TTGAAGAAAA TGACCCAAGT GACAGGAATC    5085

ATGAATTCAC CACACCAGGC ACGCACTGTG TTTTTTGGCA GTTTTTTGAC AGTGAGGAAG    5145

TCCATCTTAA CATCGGATGG GACTGTAATG CCCAATGTTT TGTCCTATGC CGCTCAGACC    5205

TCGCGTGGGT ATTGTGGCGC TGCAATTGTT GCTGGCTCAC CTGCCCGCAT AATTGGTATC    5265

CATTCAGCTG GCACTGGATC TGTTGCATTT TGCTCCCTGG TGTCCAGAGA CGCGCTGGAG    5325

CAACTCTGGC CCCAGAAACA GGGCAACGTT AGTCGCCTTG ATGACGATGT GAGGGTGTCT    5385

GTTCCGCGCC GCTCCAAATT GGTGAAATCA TTGGCTTACC CCATTTTCAA ACCTGACTAT    5445

GGCCCAGCGC CACTCTCTCA ATTTGACAAG CGCCTGTCAG ACGGCGTGAA GCTGGATGAA    5505

GTGGTTTTTG CTAAACATAC TGGAGACAAG GAGATTTCCG CACAGGACCA GAAATGGCTC    5565

TTGCGTGCGG CGCATGTATA CGCCCAGAAG GTTTTCTCCC GGATTGGATT TGACAACCAG    5625

GCTTTGACTG AAAAAGAGGC CATTTGTGGC ATTCCTGGCC TTGACAAGAT GGAGCAGGAC    5685

ACCGCTCCCG GGCTGCCCTA TGCTCAGCAA AATAAGAGAA GGAAAGACAT CTGTGATTTT    5745

GAAGAGGGCC GGCTGAAGGG CGCCGAACTC CAAAAGGACA GATTTATGGC TGGTGACTAC    5605

TCTAATTTGG TCTATCAATC ATTTTTGAAA GATGAGATCC GCCCACTTGA GAAAGTTAGG    5665

GCTGGAAAGA CCCGCCTGAT TGACGTGCCG CCGATGCCCC ATGTGGTGGT TGGTAGGCAG    5925

CTCTTGGGCC GGTTTGTGGC AAAATTTCAT GAAGCAAATG GATTTGACAT TGGCTCAGCC    5985

ATTGGATGTG ACCCAGATGT GGACTGGACT CGGTTTGGCC TCGAGTTGGA GCGTTTCAGG    6045

TATGTATATG CCTGTGACTA CTCACGGTTC GATGCCAACC ATGCAGCTGA TGCAATGAGA    6105

GTTGTGCTTA ACTACTTTTT CTCTGAGGAC CACGGTTTCG ACCCTGGTGT GCCTGCTTTT    6165

ATTGAGTCAC TGGTTGATTC AGTGCATGCC TATGAAGAGA AAAGGTATAA CATCTACGGT    6225

GGCTTGCCAT CCGGGTGTTC CTGCACATCA ATTTTGAATA CCATCTTGAA CAATGTTTAC    6285

ATTCTTGCAG CTATGATGAA GGCTTATGAG AATTTTGAGC CAGATGACAT TCAGGTCATT    6345
```

-continued

```
TGCTATGGGG ACGACTGCCT CATTGCTTCT GATTTTGAAA TTGATTTCCA ACAACTGGTG    6405

CCTGTCTTTT CTAGTTTTGG ACAGGTAATA ACTACAGCTG ACAAGACTGA TTTTTTTAAA    6465

CTGACAACGC TTTCGGAGGT GACCTTCCTT AAGCGCGCTT TTGTTCTGAC GGCCTTTTAC    6525

AAGCCAGTGA TGGATGTGAA GACCCTTGAA GCAATCTTAA GCTTTGTTCG CCCAGGCACA    6585

CAGGCTGAAA AGCTCCTGTC CGTGGCGCAG TTGGCAGGCC ACTGCGAACC GGAGCAGTAT    6645

GAGCGCCTGT TTGAGCCCTT TGCTGGGATG TATTTCGTCC CTACTTGGCG ACTTGCGCCT    6705

GCAGTGGTTG ATGAAGCTTG GATGCTAAAT TCTTTTTGAC TTTGTTTTTC TTTGTTTTCT    6765

TTTAGGCTTT TAAGGTGTTA AGTTTAAAGG TTAAGAGTTT TTAGAAGTTA AGATAGAGTT    6825

TAGTTTTTAG TTTTGAGC-poly (A)
``` as disclosed in FIG. 2 and functional equivalents of said nucleotide sequence including naturally occurring derivatives, variants, degeneracy equivalents and deletion mutants thereof.

In another aspect, the invention provides a substantially pure amino acid sequence being:

a substantially pure amino acid sequence (SEQ ID NO:2) being:

M A A S K V Y R V C E Q T L L A G A V R M M D K F

L Q K R T V F V P H L D K T I R L T G L H N Y D N

T C W L N A L T Q L T Q I L G I R L F D E H F G N

R G L F T R K T I D W V S D Q T G I K D L K S G A

P P L V V V Y K L W Q H G H L D V G T M E K P R S

I T L W S G P K V C L S D F W A C V S A K P G H A

V F Y L L T S E G W I C V D D K K I Y P E T P K T

E D V L V F A P Y D F E S L G K D P P K L H Q R Y
           L ↓ VP4

E K A F E L S G G G T S T P T T G N Q N M S G N S

G S I V Q N F Y M Q Q Y Q N S I D A D L G D N V I

S P E G Q G S N T S S S T S S S Q S S G L G G W F
             VP4 ↓ VP2

S S L L N L G T K L L A D K K T E E T T N I E D R

I E T T V V G V T I I N S Q G S V G T T Y C Y S K

P D G R P P S T V S D P V T R L G P T L S R H Y T

F K V G E W P H S Q S H G H A W I C P L P G D K L

K K M G S F H E V V K A H H L V K N G W D V V V Q

V N P S F A H S G P L C V A A V P E Y E H T H E K

A L K W S E L E E P A Y T Y Q Q L S V F P H Q L L

N L R T N S S V H L V M P Y I G P G Q P T N L T L

H N P W T I V I L I L S E L T G P G Q T V P V T M
             VP2 ↓ VP3

S V A P I D A M V N G P L P N P E A P I R V V S V

P E S D S F M S S V P D N S T P L Y P K V V V P P

R Q V P G R F T N F I D V A K Q T Y S F C S I S G

-continued

K P Y F E V T N T S G D E P L F Q M D V S L S A A

E L H G T Y V A S L S S F F A Q Y R G S L N F N F

I F T G A A A T K A K F L V A F V P P H S A A P K

T R D E A M A C I H A V W D V G L N S A F S F N V

P Y P S P A D F M A V Y S A E R T V V N V S G W L

Q V Y A L T A L T S T D I A V N S K G R V L V A V
             VP3 ↓ VP1

S A G P D F S L R H P A D L P D K Q V T N V G E D

G E P G E T E P R H A L S P V D M H V H T D V S F

L L D R F F D V E T L E L S N L T G S P A T H V L

D P F G S T A Q L A W A R L L N T C T Y F F S D L

E L S I Q F K F T T T P S S V G E G F V W V K W L

P V G A P T K T T D A W Q L E G G G N S V R I Q K

L A V A G M C P T V V F K I A G S R S Q A C A S A

L P Y T S M W R V V P V F Y N G W G A P T K E K A

T Y N W L P G A H F G S I L L T S D A H D K G G C

Y L R Y A F R A P A M Y C P R P I P P A F T R P A
             VP1 ↓ 2A

D K T R H K F P T N I N K Q C T N Y S L L K L A G
      2A ↓ 2B

D V E S N P G P T I F S K A S A D L N A L S T S L

G E L T G M L K D L K A K A E T Y S P F Y K M A K

M L F K L A T L A V A A M R T K D P V V V V M L I

A D F G L E V F D T G F F F S Y F Q E K L Q P Y M

K T I P G K I S D L V T D A A T A A A Q I P K G V
             2B ↓ 2C

Y S F V S S F F E T P E G V V E K Q V S L R T V N

D I F A L L K N S D W F I K T L V A L K K W L T S

W F A Q E Q Q A D D A L Y S E L E K Y P L Y K L K

L K E P D T Q E E A R Q W F K D M Q Q R A L A V K

-continued

D K G L F S L L Q I P L V N L P Q S R P E P V V C

V L R G A S G Q G K S Y L A N L M A Q A I S L L L

V G K Q D S V W S C P P D P T Y F D G Y N G Q A V

V I M D A L G Q D P N G A D F K Y F C Q M V S T T

A F V P P M A H L D D K G I P F T S P V V I C T T

N L H S S F T P I T V S C P E A L K R R F R F D V

T V S A K P G F V R T V G S N Q L L N L P L A L K

P A G L P P H P I F E N D M P I I N G Q A V K L A

L S G G E V T A F E L I E M I L S E V Q N R Q D T
         2C ↓ 3A

H K M P I F K Q S W S D L F R K C T T D E E Q K M

L Q F L I D N K D S E I L R A F V S E R S I L L H

E E Y L K W E S Y M T R R A K F H R L A A D F A M

F L S I L T S L I V I F C L V Y S M Y Q L F K T P
   3A ↓ 3B

D E Q S A Y D P S T K P K P K T Q E V K T L K I R
 3B ↓ 3C

T E T G V P A T D L Q Q S I M K N V Q P I E L Y L

D N E L V T D C S A L G V Y D N S Y L V P L H L F

E F D F D T I V L G G R H Y K K A E C E K V E F E

L E V N G D V V S S D A C L L R V S S G P K V R N

I V H L F T N E I E L K K M T Q V T G I M N S P H

Q A R T V F F G S F L T V R K S I L T S D G T V M

P N V L S Y A A Q T S R G Y C G A A I V A G S P A

R I I G I H S A G T G S V A F C S L V S R D A L E
     3C ↓ 3D

Q L W P Q K Q G N V S R L D D D V R V S V P R R S

K L V K S L A Y P I F K P D Y G P A P L S Q F D K

R L S D G V K L D E V V F A K H T G D K E I S A Q

D Q K W L L R A A H V Y A Q K V F S R I G F D N Q

A L T E K E A I C G I P G L D K M E Q D T A P G L

P Y A Q Q N K R R K D I C D F E E G R L K G A E L

Q K D R F M A G D Y S N L V Y Q S F L K D E I R P

L E K V R A G K T R L I D V P P M P H V V V G R Q

L L G R F V A K F H E A N G F D I G S A I G C D P

D V D W T R F G L E L E R F R Y V Y A C D Y S R F

D A N H A A D A M R V V L N Y F F S E D H G F D P

G V P A F I E S L V D S V H A Y E E K R Y N I Y G

G L P S G C S C T S I L N T I L N N V Y I L A A M

M K A Y E N F E P D D I Q V I C Y G D D C L I A S

D F E I D F Q Q L V P V F S S F G Q V I T T A D K

T D F F K L T T L S E V T F L K R A F V L T A F Y

-continued

K P V M D V K T L E A I L S F V R P G T Q A E K L

L S V A Q L A G H C E P E Q Y E R L F E P F A G M
                              3D

Y F V P T W R L A P A V V D E A W M L N S F as disclosed in FIG. 2.

In another aspect, the invention provides proteins derived from ERhV1 which exhibit virus like particle characteristics incorporating VP1 and having the following amino acid sequence:

a protein or virus like particle incorporating VP1, derived from ERhV1 and having the following amino acid sequence (SEQ ID NO:3):

V T N V G E D G E P G E T E P R H A L S P V D M H

V H T D V S F L L D R F F D V E T L E L S N L T G

S P A T H V L D P F G S T A Q L A W A R L L N T C

T Y F F S D L E L S I Q F K F T T T P S S V G E G

F V W V K W L P V G A P T K T T D A W Q L E G G G

N S V R I Q K L A V A G M C P T V V F K I A G S R

S Q A C A S A L P Y T S M W R V V P V F Y N G W G

A P T K E K A T Y N W L P G A H F G S I L L T S D

A H D K G G C Y L R Y A F R A P A M Y C P R P I P

P A F T R P A D K T R H K F P T N I N K Q C T

In another aspect, the invention provides proteins derived from ERhV1 which exhibit virus like particle characteristics incorporating VP2 and having the following amino acid sequence:

a protein or virus like particle incorporating VP2, derived from ERhV1 and having the following amino acid sequence (SEQ ID NO:4):

D K K T E E T T N I E D R I E T T V V G V T I I N

S Q G S V G T T Y C Y S K P D G R P P S T V S D P

V T R L G P T L S R H Y T F K V G E W P H S Q S H

G H A W I C P L P G D K L K K M G S F H E V V K A

H H L V K N G W D V V V Q V N P S F A H S G P L C

V A A V P E Y E H T H E K A L K W S E L E E P A Y

T Y Q Q L S V F P H Q L L N L R T N S S V H L V M

P Y I G P G Q P T N L T L H N P W T I V I L I L S

E L T G P G Q T V P V T M S V A P I D A M V N G P

L P N P E

In another aspect, the invention provides proteins derived from ERhV1 which exhibit virus like particle characteristics incorporating VP3 and having the following amino acid sequence:

a protein or virus like particle incorporating VP3, derived from ERhV1 and having the following amino acid sequence (SEQ ID NO:5):

A P I R V V S V P E S D S F M S S V P D N S T P L

Y P K V V V P P R Q V P G R F T N F I D V A K Q T

Y S F C S I S G K P Y F E V T N T S G D E P L F Q

M D V S L S A A E L H G

-continued

```
AAGTGGTCTG  AGCTTGAGGA  ACCAGCTTAC  ACATACCAAC  AACTTTCAGT  TTTTCCCCAC

CAGTTGCTAA  ATTTGAGGAC  AAATTCATCA  GTGCATTTGG  TGATGCCCTA  CATTGGGCCA

GGCCAACCAA  CAAATCTGAC  TTTGCACAAC  CCGTGGACCA  TTGTTATTTT  AATTTTGTCT

GAATTGACAG  GACCTGGCCA  AACTGTGCCT  GTGACCATGT  CGGTGGCTCC  CATCGATGCA

ATGGTTAATG  GGCCTCTTCC  AAATCCAGAG
``` and functional equivalents of said nucleotide sequence including naturally occurring derivatives, variants and degeneracy equivalents.

In another aspect, the invention provides a substantially pure nucleotide sequence for VP3 (SEQ ID NO:9) being:

```
GCACCGATTA  GAGTGGTGTC  TGTGCCTGAA  TCAGATTCTT  TTATGTCTTC  AGTACCTGAT

AATTCGACTC  CACTATACCC  CAAGGTTGTG  GTCCCACCGC  GCCAAGTTCC  TGGCCGGTTT

ACAAATTTCA  TTGATGTGGC  AAAACAGACA  TATTCATTTT  GTTCCATTTC  TGGAAAACCT

TATTTTGAGG  TTACCAACAC  CTCTGGGGAC  GAGCCACTGT  TTCAGATGGA  TGTGTCGCTC

AGTGCGGCAG  AGCTACATGG  CACTTACGTA  GCTAGTTTGT  CATCATTTTT  TGCACAGTAC

AGAGGCTCAC  TTAATTTCAA  CTTTATTTTC  ACTGGTGCAG  CAGCCACTAA  GGCAAAGTTT

CTGGTTGCTT  TTGTGCCTCC  CCACAGTGCA  GCGCCCAAAA  CGCGCGATGA  AGCAATGGCG

TGCATCCATG  CCGTGTGGGA  TGTTGGCTTG  AACTCAGCTT  TTTCTTTTAA  TGTACCTTAT

CCCTCCCCTG  CTGACTTCAT  GGCCGTTTAT  TCTGCGGAAC  GGACGGTTGT  GAATGTCTCT

GGATGGCTTC  AAGTTTATGC  ACTAACAGCT  CTAACTTCAA  CTGACATTGC  CGTGAACAGT

AAAGGCCGTG  TGCTGGTTGC  TGTTTCCGCC  GGCCCAGACT  TCTCCCTTCG  TCACCCGGCG

GACCTGCCCG  ACAAGCAG
``` and functional equivalents of said nucleotide sequence including naturally occurring derivatives, variants and degeneracy equivalents.

In another aspect, the invention provides a substantially pure nucleotide sequence for VP4 (SEQ ID NO:10) being:

```
GGCGGAGGTA  CATCCACTCC  AACAACTGGC  AACCAAAACA  TGTCCGGAAA  CAGTGGTTCA

ATTGTTCAAA  ATTTTTACAT  GCAACAGTAC  CAGAATTCAA  TTGACGCAGA  CCTGGGAGAC

AATGTGATTA  GCCCTGAAGG  CCAGGGCAGC  AACACTAGTA  GTTCAACCTC  ATCAAGCCAA

TCCTCTGGCT  TGGGCGGGTG  GTTCTCTAGT  TTGCTGAACC  TTGGAACAAA  ACTACTGGCT
``` and functional equivalents of said nucleotide sequence including naturally occurring derivatives, variants and degeneracy equivalents.

In another aspect, the invention provides oligonucleotide primers derived from the nucleotide sequence of FIG. 2 being highly specific for ERhV1 or cross reactive with other ERhV types.

The oligonucleotide primers may have any one of the following nucleotide sequences:

VP1F (SEQ ID NO: 11) 5' GTTGTGTTCAAGATTGCAGGC 3'

VP1R1 (SEQ ID NO: 12) 5' TTGCTCTCAACATCTCCAGC 3'

VP1R2 (SEQ ID NO: 13) 5' TAGCACCCTCCTTTATCATGCG 3'

In another aspect, the invention provides an oligonucleotide probe derived from the sequence of FIG. 2.

In another aspect, the invention provides diagnostic reagents, methods and kits characterised by the aforesaid oligonucleotide primers and probes.

In another aspect, the invention provides antigens comprising any one or a combination of the non-capsid proteins, being other than the individual VP1 to VP4 proteins, that are cleavage products of the polypeptide of FIG. 2.

In another aspect, the invention provides vaccines and vectors incorporating any one or a combination of virion proteins VP1 to VP4.

In another aspect, the invention provides diagnostic tests for the detection of antibodies to ERhV1 in blood of horses or other animals characterised by the use of the aforesaid antigens. Such diagnostic tests may be ELISA based.

In a particularly preferred embodiment, the invention provides a test to distinguish horses infected with ERhV1 in which said virus had replicated from horses which have been vaccinated with the vaccine incorporating any one or a combination of virion proteins VP1 to VP4; comprising the steps of applying an antigen being any one or a combination of non-capsid proteins, being other than VP1 to VP4, that are cleavage products of the polypeptide of FIG. 2 to a horse and testing for an immunoreaction thereto, wherein a positive immunoreaction would indicate that said horse had been infected with ERhV1 and a negative immunoreaction would indicate that said horse has not been infected with ERhV1.

In another aspect, the invention provides recombinant plasmids incorporating nucleotide sequences and subsequences derived from the nucleotide sequences of FIG. 2. The recombinant plasmid may comprise the P1-2A-3C region of the ERhV1 genome.

In another aspect, the invention provides a host system characterised by incorporating the nucleotide sequence of FIG. 2 or part thereof. The host may be E.coli, vaccinia virus, baculovirus or yeast.

In another aspect, the invention provides a process for producing a protein product derived from ERhV1 comprising the steps of selecting out a gene of interest from the ERhV1 nucleotide sequence of FIG. 2 and expressing said protein product in a suitable host system.

DETAILED DESCRIPTION OF INVENTION

Figure 1B:
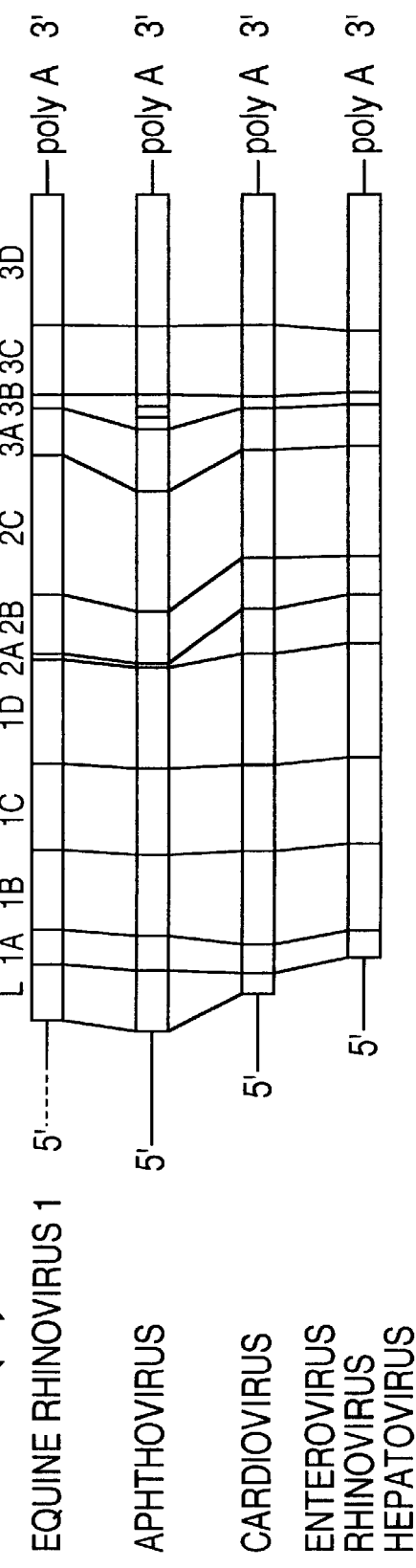

The invention will now be described in detail with reference to FIGS. 1 to 6:

FIG. 1 (A) Schematic representation of the ERhV1 genome and (B) comparison of the genomic structures of picornaviruses showing the predicted proteolytic cleavage pattern of the polyprotein. The lengths of individual regions are drawn approximately to scale. The dashed line represents the unsequenced region of the ERhV1 5'-NTR.

FIGS. 2A–1–2G–2 Nucleotide and predicted amino acid sequence of the ERhV1 polyprotein (SEQ ID NOS:1 & 2). The nucleotide sequences of the 3'-NTR and part of the 5'-NTR are also shown. Numbering is from the first ATG codon that occurs in a context optimal for translational initiation (Kozak, 1989). A polypyrimidine tract upstream of the putative initiating ATG and the two pairs of in-frame ATG codons are underlined. The predicted proteolytic cleavage sites are indicated by arrows.

FIGS. 2H–1–2H–2 Nucleotide sequence of the ERhV1 5'-nontranslated region (SEQ ID NO:22). The polyC tract (dotted underline), polypyrimidine tract (underline) and potential initiation codons (double underline) are indicated.

Predicted coding sequence is shown in bold type (SEQ ID NO:23). Numbering is from the ATG considered most likely to be used for translation initiation.

FIG. 3 Alignment of the predicted amino acid sequences of ERhV1.393176 (SEQ ID NO:25) and FMDV.O1K (SEQ ID NO:24) polyprotein. Proteolytic cleavage sites, which are predicted in the case of ERhV1, are indicated by the arrows. Identical residues (*), highly conserved residues (:), and less conserved residues (.), are indicated.

FIG. 4 Unrooted phylogenetic trees inferred using the picornavirus nucleotide sequences of (A) the complete polyprotein gene, (B) the polymerase gene and (C) VP1 gene of viruses representing the five recognised genera of the family Picornaviridae. The viruses used were: FMDV.A10, FMDV.O1K, FMDV.A12, FMDV.C3, FMDV.SAT3, EMCV, TMEV, Mengovirus, poliovirus 1.Mahoney (Polio 1), poliovirus 2.Sabin (Polio 2), poliovirus 3.Leon (Polio 2), coxsackievirus A9 (CV.A9), CV.B3, echovirus 22 (Echo 22), swine vesicular disease virus (SVDV), bovine enterovirus (BEV) hepatitis A virus (HAV) human rhinovirus 1B (HRV1B), HRV89 and HRV14.

Note: The branch lengths represent proportionate change only within each tree; they do not allow direct comparisons to be made between the three trees.

Figures 5A, 5B:
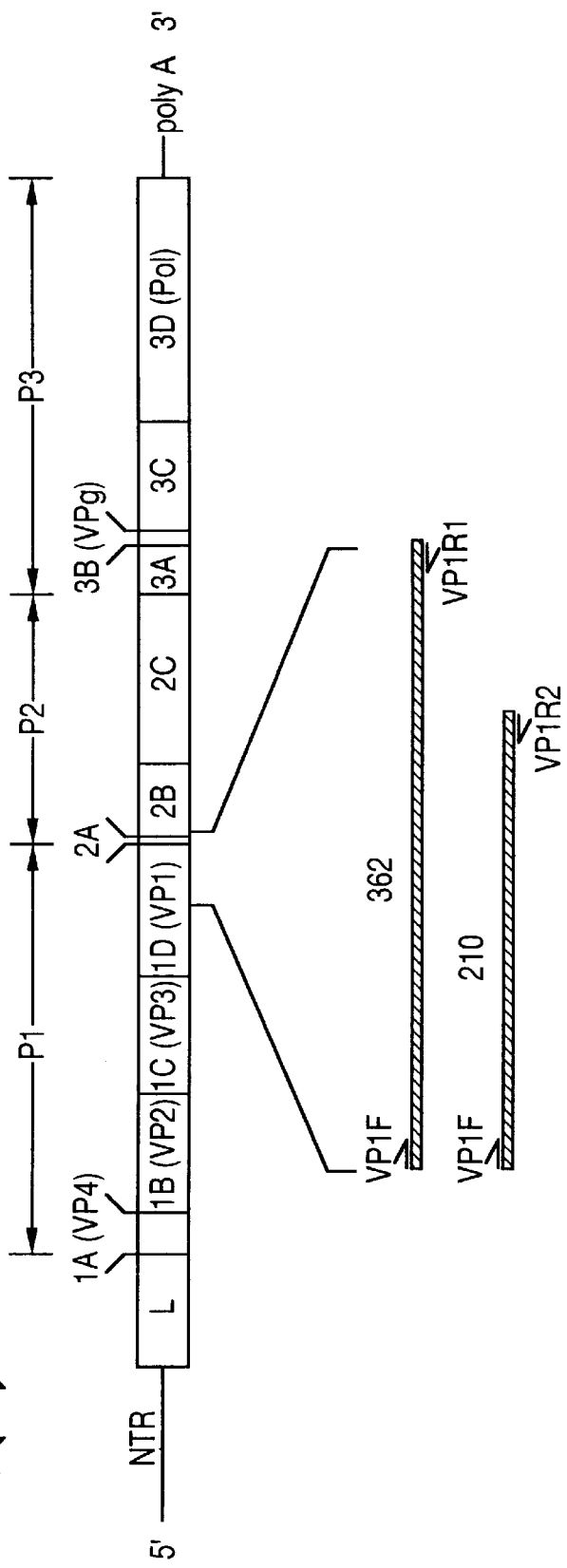

FIG. 5(A) Diagram outlining the strategy for nested, reverse transcription-polymerase chain reaction (RT-PCR) for the detection of ERhV genome. The genome structure of ERhV1 is shown schematically (top), and the first round PCR product (362 bp), corresponding to VP1 and 2A regions, and the second round PCR product (210 bp), corresponding to part of VP1, are represented as black lines.

(B) the sequence of specific oligonucleotide primers used for RT-PCR are shown (SEQ ID NO:11, 12 & 13). VP1R1 was used for the RT reaction.

Figure 6:
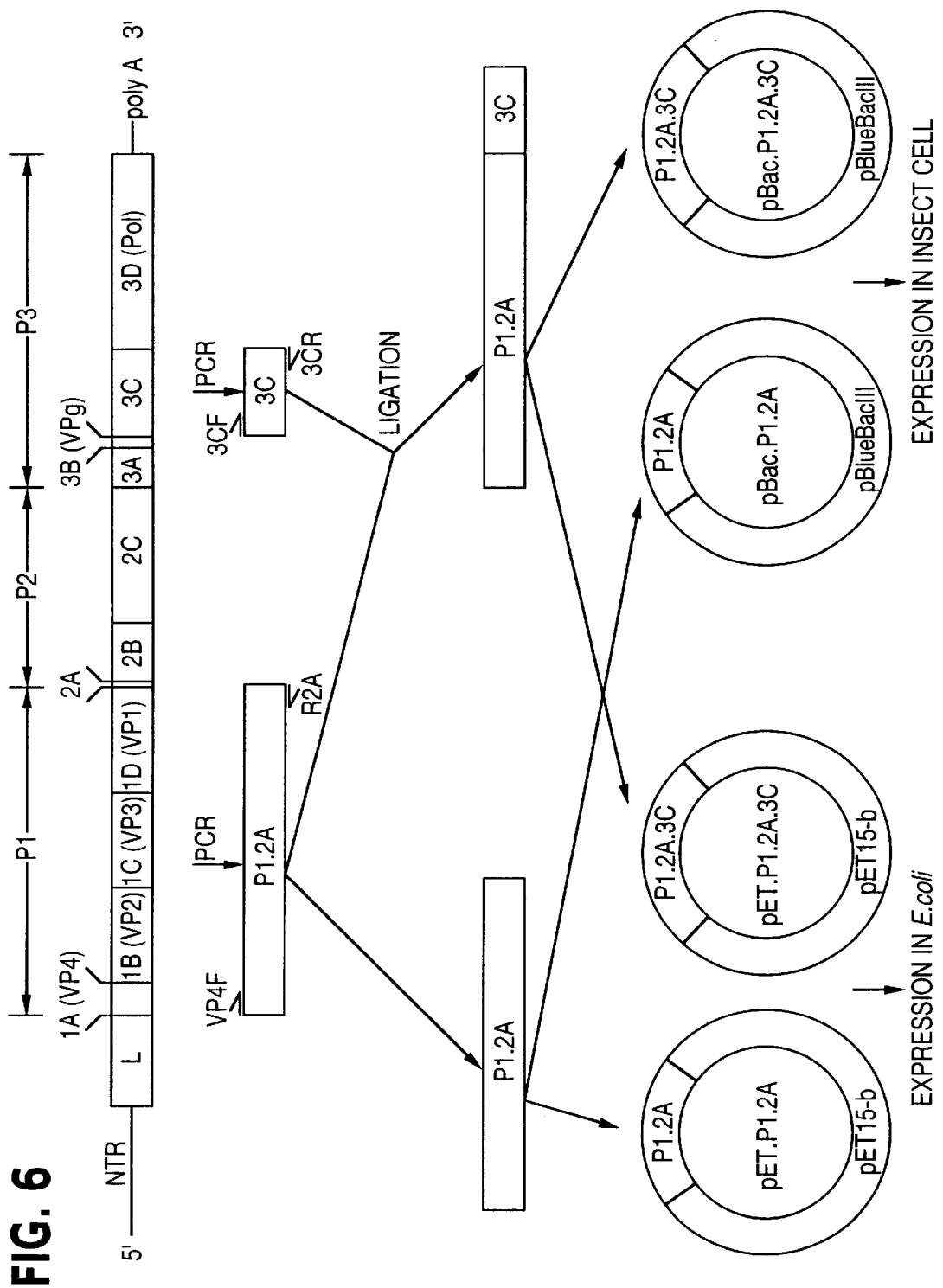

FIG. 6 Construction of ERhV1 expression plasmid for E. coli and baculovirus transfer vector for insect cells. The ERhV1 genome is shown (top) and oligonucleotide primers used to amplify P1.2A and 3C regions are depicted as arrows. The Pt1.2A fragment and subsequently the P1.2A.3C fragment, obtained through the ligation of P1.2A and 3C, were cloned separately into the multiple cloning sites of the pET15b and pBacbluIII plasmid vectors to construct pET.P1.2A and pET.P1.2A.3C respectively for expression in E. coli and pBac.P1.2A and pBac.P1.2A.3C respectively for expression in insect cells.

The sequence of specific oligonucleotide primers used for the construction of expression plasmids are:

```
VP4F (SEQ ID NO: 14)   5'  GCTGGATCCATGAGTGGCGGAGGTACATCCACT   3'

R2A  (SEQ ID NO: 15)   5'  GCTCTGCAGCAGGTCTGCTGATGCTTTGGA      3'

3CF  (SEQ ID NO: 16)   5'  GCTCTGCAGATGATTAGGACTGAGACTGGTGT    3'

3CR  (SEQ ID NO: 17)   5'  GCTGGATCCTTAGCCATAGTCAGGTTTGAA      3'
```

Virus Growth and Purification

ERhV1 strain 393/76 was isolated from a nasal swab taken from a thoroughbred horse in South Australia while it was being held in quarantine following importation from the United Kingdom. The mare had an acute, systemic febrile illness. The virus was passaged 14 times in equine fetal kidney (EFK) monolayer cell cultures and then once in Vero cells. ERhV1 virions were purified by a modification of the procedure described by Abraham and Colonno. Cells were harvested 48 hours after infection. The infected cells and supernatant fluid were frozen and thawed three times and clarified by centrifuging at 2,000×g for 20 min at 4 C. Polyethylene glycol 6000 and NaCl were added to the supernatant to final concentrations of 7% and 380 mM, respectively, and the mixture was stirred overnight at 4 C. The precipitated virions were recovered by centrifuging at 10,000×g for 15 min at 4 C. and resuspended in 200–400 μl TNE buffer (10 mM Tris-HCI pH 8.0, 100 mM NaCl, 1 mM EDTA) containing 1% NP40. The suspension was clarified by centrifuging at 12,000×g for 3 min before layering onto 15% to 45% (wt/vol) linear sucrose gradients (35 ml) in TNE buffer and centrifuging at 100,000×g for 4 h at 4 C. Gradients were fractionated and the fractions analyzed by SDS-PAGE. Viral fractions were pooled, centrifuged at 200,000×g for 2 h at 4 C., and the viral pellet was resuspended in a small volume of TNE buffer, cDNA synthesis and cloning. Viral RNA was reverse transcribed using an oligo-dT primer (Amersham) or ERhV1 specific primers P1 (SEQ ID NO:18) (5'-ATCCAGCAAGCCGCTGTCCGGTTAC-3') and P5 (SEQ ID NO:19) (5'-CGAAGAGACACCTGCTTC-3'). Viral RNA was prepared as described in (1987) Anal-Biochem. 162, 156–159.

Viral RNA and 100 pmol of primer were mixed, boiled for 2 min and cooled at room temperature. First strand cDNA was synthesized using 200 U of Maloney murine leukemia virus reverse transcriptase (Promega) in the presence of 0.8 mM dNTPs and 30 U of human placental RNAse inhibitor (Pharmacia) in a reaction volume of 25 μd. Second strand cDNA was synthesized using a cDNA synthesis kit (Amersham). The cDNA fragments were ligated into pUC18, either as blunt ended fragments or after ligating BamH I adaptors (Pharmacia), and the lighted products used to transform E. coli strain DH5α (Stratagene). Colonies were selected by hybridization, initially with an [32P]-dCTP-labelled cDNA probe derived from reverse transcribed viral RNA, and subsequently with [32P]-dCTP-labelled cloned viral cDNA (16). The sequence between two cDNA clones was obtained using the oligonucleotide primers P6 (SEQ ID NO:20) (5'-TTCTGGTGGAGAAGTGACAGC-3') and P7 (SEQ ID NO:21) (5'-GTGAGCCAGCAACAATTGC-3') in a polymerase chain reaction (PCR; 17) using the polymerase, Vent Exo+(New England Biolabs).

DNA Sequencing and Analyses

Double-stranded DNA was prepared using the alkaline lysis method and sequenced by dideoxy chain termination using modified T7 DNA polymerase (Pharmacia) and [35S]-dATP (Amersham). Sequence was read and analyzed using the GeneWorks software package (IntelliGenetics, Mountain View, Calif.). The GenBank database was searched using the FASTA searching and comparison program. The protein alignment shown in FIG. 3 was performed using the Genetics Computer Group, Inc. (Madison, Wis., USA, 1994) GAP program with a gap creation penalty (GCP) of 3.0 and a gap extension penalty (GEP) of 0.1. The multiple alignments of nucleotide sequences were performed using ClustalW. For pairwise alignments the slow method was used with a GCP of 10 and a GEP of 0.1. For multiple alignments a GCP of 10 and a GEP of 0.05 was used, with alignment of sequences which were more than 60% divergent delayed and using weighted transitions. Phylogenetic relationships were examined using the maximum likelihood method with the DNAML program of the Phylogeny inference Package (Phylip) version 3.5c (1993, J. Felsenstein, Department of Genetics, University of Washington, Seattle). The model used allowed for unequal expected frequencies of the four nucleotides, with the frequencies determined empirically from those present in the sequences analysed, and unequal rates of transitions and transversions. A single rate of change was assumed for all sites. The program was allowed to perform global rearrangements to optimise the tree. Initial analyses were performed on polymerase sequences using a range of transition/transversion ratios to determine that which gave the maximal log likelihood. A ratio of 2.0 gave the maximal log likelihood and thus this ratio was used for all subsequent analyses of other sequences.

Cloning and Sequencing of the ERhV1 Genome

Sixty seven overlapping cDNA clones and one PCR product clone were obtained and sequenced from both ends. The nucleotide in each position was determined at least twice, and 95% of the sequence was obtained by sequencing in both directions. The predicted genomic structure of ERhV1 was characteristic of picornaviruses, possessing one long open reading frame (ORF) flanked by 5'- and 3'-NTR's (FIG. 1).

The nucleotide and predicted amino acid sequences of the ERhV1 polyprotein are shown in FIG. 2a. Partial sequence of the 5'-NTR (433 bases) was also obtained FIG. 2b. There was a tract of 9 Cs at position −550 to −542. PolyC tracts of various lengths have been observed in similar locations in FMDV and EMCV. The actual length of the ERhV1 polyC tract is uncertain as these sequences are known to be unstable when propagated in E. coli. A 14 nucleotide polypyrimidine tract, which possessed the TTTC motif common to all picornaviruses, was present near the potential translation initiation codons. A region of 450 nucleotides upstream of the most likely initiation codon is predicted to contain an internal ribosome entry site (IRES). This region showed most sequence identity (48–50%) with corresponding sequences in FMDV and EMCV. The 3'-NTR of ERhV1 was 102 nucleotides excluding the polyA tail (data not shown).

In picornaviruses, there are two factors that influence which ATG codon initiates translation, a requirement for the ATG to be located at the 3'-end of the IRES, and that this ATG occurs in a sequence optimal for initiating translation, that is, a purine at position −3 and a G in position +4. Two pairs of in-frame ATG codons were identified in the ERhV1 genome. The second ATG of the first pair is separated by 25 nucleotides from the beginning of the polypyrimidine tract (FIG. 2b), similar to the distance (25 to 27 nucleotides) found in the corresponding regions in FMDV and EMCV (24). The second ATG of each pair occurs in an optimal context. Therefore, the second ATG of the first pair is most likely to be the translation initiation codon but it is possible that translation is also initiated from the second optimal ATG, by a process of leaky scanning, or even from the other two, non-optimal ATG codons. The predicted ERhV1 coding sequence, beginning at the most likely initiation ATG, extended for 6,741 bases and would encode a polyprotein of 2,247 amino acids.

Alignment of the ERhV1 amino acid sequence with those of other picornaviruses showed that it was most similar to aphthoviruses and, to a lesser extent, to cardioviruses in all regions of the genome (data not shown). FIG. 3 shows a comparison of the predicted amino acid sequence of ERhV1 with that of FMDV.O1K. The two sequences were 40% identical. The more conserved regions include: the 3D/polymerase (50% identity), VP4 (49% identity) and some regions of the 2C protein. ERhV1 encoded a 2A protein of 16 amino acids. 14 of which were identical with those of FMDV 2A. ERhV1 possessed only one copy of the VPg sequence. This is in contrast to FMDV which has 3 tandemly repeated, non-identical VPg sequences (27–29).

Table 1 shows the proteolytic cleavage sites of ERhV1 predicted from the amino acid alignment (FIG. 3), and compares these with those of FMDV, EMCV and Theiler's murine encephalomyelitis virus (TMEV). Most of the ERhV1 cleavage sites could be assigned with reasonable confidence because of significant amino acid similarity with FMDV in the regions flanking the predicted cleavage site, an exception was the 3A/3B cleavage site where there was less sequence similarity. As is the case with FMDV, the predicted ERhV1 3C protease cleavage sites were more variable than those of the cardioviruses, EMCV and TMEV.

TABLE 1

Comparison of the predicted proteolytic cleavage sites of the ERhV1 polyprotein with those of FMDV, EMCV and TMEV.

| Proteins | Cleavage sites* | | | |
|---|---|---|---|---|
| | ERhV1 | FMDV | EMCV | TMEV |
| Leader/1A(VP4) | S/G | K/G | Q/G | Q/G |
| 1A(VP4)/1B(VP2) | A/D | A/D | A/D | L/D |
| 1B(VP2)/1C(VP3) | E/A | E/G | Q/S | Q/S |
| 1C(VP3)/1D(VP1) | Q/V | E/T | Q/G | Q/G |
| 1D(VP1)/2A | T/N | L/N | E/S | E/N |
| 2A/2B | NPG/P | NPG/P | NPG/P | NPG/P |
| 2B/2C | Q/V | Q/L | Q/S | Q/G |
| 2C/3A | Q/S | Q/I | Q/G | Q/S |
| 3A/3B | Q/S | E/G | Q/G | Q/G |
| 3B/3C | E/T | E/S | Q/G | Q/G |
| 3C/3D | Q/G | E/G | Q/G | Q/G |

*Cleavage data from: FMDV.O1K (Forss et al. 1984), TMEV (Pevear et al. 1987) and EMCV (Palmenberg et al. 1984). The single amino acid code is used.

Phylogenetic Analyses

Figure 4A:
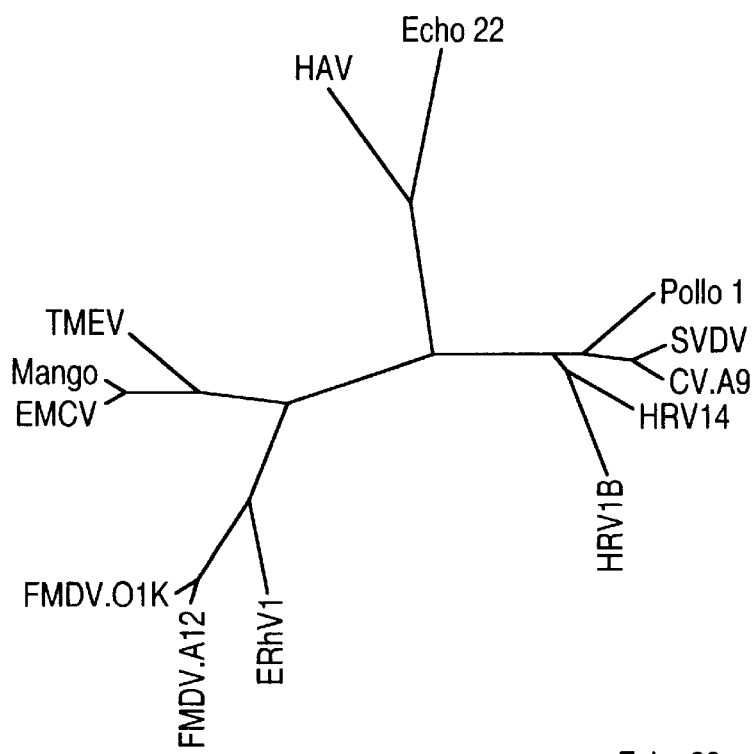
Figure 4B:
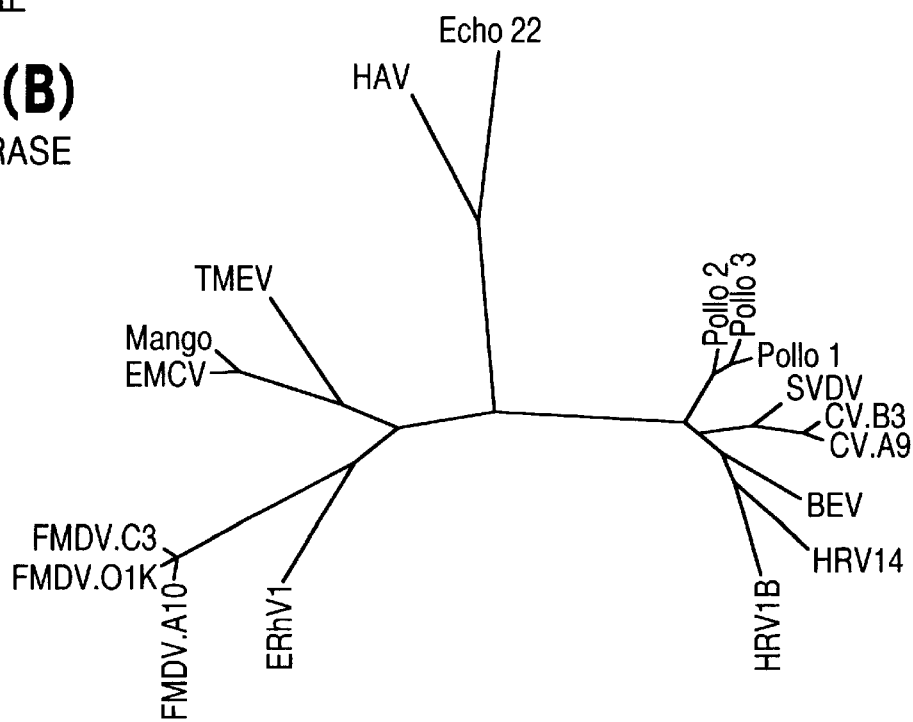
Figure 4C:
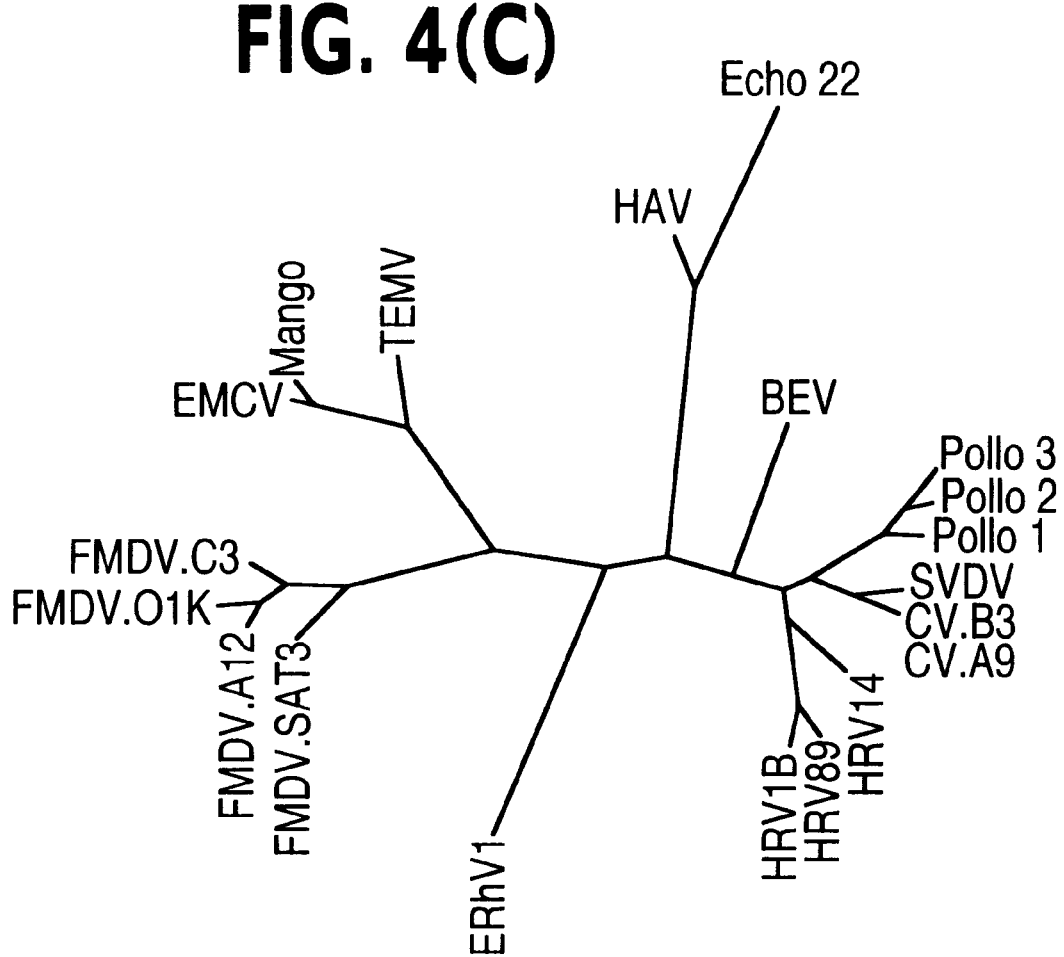

A phylogenetic tree was derived from the nucleotide sequences of complete picornavirus polyproteins (FIG. 4a). Each branch of this tree was statistically, highly significant (P<0.01), with the 95% confidence limits ranging from ±7% to ±15% of branch lengths. ERhV1 was found to be most closely related to the aphthoviruses, although it was clear that ERhV1 was considerably more distant from individual members of this genus than the aphthoviruses were from each other. A phylogenetic tree was also derived from the nucleotide sequences of picornavirus polymerase genes (FIG. 4b). Each branch of this tree was statistically, highly significant (P<0.01) with 95% confidence limits ranging from ±14% to ±38% of the branch lengths. Again. ERhV1 grouped with the aphthoviruses and the topology of the tree was the same as that obtained using data of the entire polyprotein (FIG. 4a). The VP1 nucleotide sequences were also similarly analyzed (FIG. 4c). Most branches were statistically, highly significant (P<0.01), although, that between the ERhV1 branch point and the branch point for the echovirus 22-hepatovirus cluster was less so (P<0.05). The 95% confidence limits of the branch lengths of this tree were considerably greater than for the other two trees, ranging from ±18% to ±69%. This tree did not group ERhV1 with the aphthoviruses. With the exception of bovine enterovirus (BEV), the tree had the same topology as those derived from the complete polyprotein and the polymerase sequences. It was also apparent that picornaviruses formed three clusters: enteroviruses-rhinoviruses, echovirus 22-hepatovirus and cardioviruses-aphthoviruses-ERhV 1.

(1) Diagnostic Reagents

Oligonucleotide primers: We have designed short oligonucleotide primers and used them in polymerase chain reactions (PCR) for the diagnosis of ERhV infected horses. Any of the ERhV nucleotide sequence may be used for the design primer sets for use as diagnostic reagents. They may be highly specific for ERhV1 or they may be designed to be more cross reactive so as to amplify single strand RNA template from other ERhV types e.g., ERhV 2, 3 and 4. As a specific example we have used the primer set shown in FIG. 5 to diagnose ERhV disease in several groups of seriously ill horses in circumstances in which, despite exhaustive efforts, we could not isolate the virus using conventional cell culture procedures. We now consider ERhV a very under reported disease simply because, most of the time, nasal samples collected from horses experiencing severe, systemic clinical disease because of ERhV infection do not yield the virus in cell culture. In one particular group of horses, we detected the presence of ERhV by PCR and confirmed that the horses were both actively infected and seriously ill with ERhV by use of paired serum samples which showed that there was a concomitant rise in ERhV1 serum neutralising antibody. Vigorous attempts to isolate the virus in cell cultures yielded negative results.

Oligonucleotide probes: Virus specific oligonucleotides are used as probes to detect the presence of the virus in infected samples from diseased horses and other animals. This may be especially important given the systemic nature of the illness i.e., it is a foot-and-mouth-like, generalized disease with virus distributed throughout the body in many organs and tissues; it is not just a simple "common cold-like" illness as the name rhinovirus implies The significance of the sequence in moving the virus out of the Rhinovirus genus and into a new genus proposed to be called "Equirhinovirus" in the Picornaviridae family does not represent merely a taxonomic change but represents a paradigm shift in how ERhV1 and related viruses must now be regarded as pathogens for the horse and other animal species.

Diagnostic antigens: Individual virion proteins, in particular VP 1, VP2 and VP3, can be expressed in any one of a number of heterologous expression systems to provide antigens to detect specific antibody to ERhV1 present in blood. Such expression systems, which are well established for E. coli, yeast, vaccinia virus and baculovirus, allow for the production of large quantities of protein to a high degree of purity. The expressed virion proteins may be used in simple immunoassays, such as ELISA, to detect ERhV1 specific antibody. Virion proteins expressed in this way also serve as effective vaccines against ERhV1 disease.

(2) Vaccines

Production of virus like particles (VLPs): We have used the sequence information to construct recombinant plasmids containing the P1-2A-3C region of the genome (see FIG. 1a and FIG. 6). These plasmid constructions are of course critically dependent on the ERhV1 sequence that has been determined although the strategy that we are adopting, in general, is similar to that described in J. Virol 66, 4557–4564. Some early plasmid constructions have been inserted into E. coli and baculovirus expression systems based on prior art with similar viruses such as poliomyelitis of humans and foot-and-mouth disease virus of cattle and other cloven hoofed animals. The RT PCR double stranded DNA of the P1-2A-3C region of the ERhV1 genome is transcribed, within the transformed E. coli or insect cell for baculovirus, into messenger RNA as a single transcript which is then translated into a mini polyprotein. The 3C protease activity results in the cleavage of the mini polyprotein into its constituent parts namely 1A (VP4), 1B (VP2), 1C (VP3) and 1D(VP1), 2A and 3C (see FIG. 1a and FIG. 6) and that the VP component parts then self assemble into VLPs i.e., virus particles that lack nucleic acid and are therefore non infectious i.e., are unable to cause disease. Two important applications of ERhV VLPs are as follows:

(a) The VLPs are very useful as highly effective, safe, high antigen-mass vaccines for the control ERhV1 disease. If ERhV1 disease is confirmed, as we believe to be the case, as significant and responsible for much hither to undiagnosed illness that results in many lost training days, many expensive treatments, much serious illness because of secondary infections following on the primary ERhV1 infection, and much poor performance, then the utility of the vaccine based on the VLPs that are the subject of this invention will be very great and likely to have world-wide application.

With improved methods for the diagnosis of ERhV1 infection such as by PCR and ELISA as described herein, it is likely that other members of the proposed new Equirhinovirus genus within the family Picornaviridae including for example ERhV2, ERhV3, may be similarly diagnosed. Indeed suitably selected PCR primer sets based on the ERhV1 sequence could be used to detect these other equine rhinoviruses. The sequencing of these genomes could provide a basis for their specific diagnosis. It is also evident that the construction of VLP's based on expression plasmids similar to those described herein for ERhV1, could be readily adapted to these other equine rhinoviruses leading for example to production of combined ERhV vaccines to cover all antigenic types as may be extant or as may emerge by antigenic variation, as is very much a part of the biology of FMDV, in the future. Polyvalent VLP vaccines incorporating a range of ERhV antigenic types are obvious extensions based on the work described herein.

(b) ERhV VLPs can be used as a delivery vector that will provide not only protection against ERhV disease but will be used to deliver other therapeutic and useful substances to the horses following administration by parenteral or other routes. Such delivery vectors can be produced by inserting into, for example the P1 region at some appropriate site, double stranded DNA coding for antigenic epitopes of other virus and infectious agents of horse as well as epitopes derived from other non infectious sources for example reproductive hormones.

ERhV1 Diagnostic Tests

For the detection of ERhV1 antibodies in infected or vaccinated horses various standard tests can be used. VLP's may be used in such tests for example in an ELISA test for antibody.

Other diagnostic tests based on recombinant antigens derived from the ERhV1 sequence can be devised along similar lines to those reported for FMDV in which the absence of protein 2C from clarified inactivated whole virus FMD, FMDV or FMDV VLP vaccines maybe used as the basis for distinguishing infected from vaccinated animals where the vaccine is a non-replicating form of ERhV1 or a deletion mutant of ERhV1 in which a particular non-structural protein gene has been deleted. Precedent for this comes from studies of FMDV as reported in for example Lubroth, Grubman, Burrage, Newman & Brown, 1996, Absence of protein 2C from clarified foot-and-mouth disease virus vaccines provides the basis for distinguishing convalescent from vaccinated animals, Vaccine 14(5), 419–427.

Preparation and use of Virus-like Particles and Other Proteins Based on ERhV1 Sequence From the sequence of ERhV1 it is possible to clone certain segments of the viral genome into a variety of vectors for expression in a variety of different expression systems. There is a straight forward and strong literature for FMDV that provides a very clear precedent for what can be done for ERhV1. Examples include the expression of FMDV P1-2A in a baculovirus (Abrams CC & Belsham GJ, 1994, The antigenicity of foot-and-mouth disease virus P1 -2A polyprotein and empty capsids produced in vaccinia virus and baculovirus expression systems. In VIIth Meeting of the European Study Group on the Molecular Biology of Picornaviruses, Aug. 6–11, 1994, Korpilampi, Finland) or vaccina virus systems (Abrams C. C., King A. M. Q. & Beisham G. J., 1995, Assembly of foot-and-mouth disease virus empty capsides synthesized by a vaccinia virus expression system, Journal of General Virology 76:3089–3098) to obtain VLPs or viral proteins. We have prepared similar plasmids in which P1-2A. P1-2A-3C and these two sequences in a myristolated form have been inserted into p fastbac 1 baculovirus vector (Gibco/BRL) and into a PET vector (Novogene) for expression in insect cells and $E.coli$ respectively.

These expressed products either as protein antigens or as VLPs, have utility as the basis for diagnostic tests or vaccines.

Accordingly, such references are herein incorporated in support of the full description and enablement of the invention where the disclosed methods of preparing diagnostics, vaccines, vectors, host systems and kits are filly described and applicable to the like aspects of the current invention.

(3) Applications in Human Medicine:

ERhV is also a human pathogen. We have unpublished data to confirm that humans have serum neutralising antibody to ERhV1 that is indicative of infection. One of the laboratory workers concerned with the conduct of the sequencing and who handled infectious virus has specific antibody in high amounts (serum neutralising antibody titre 1:640 to ERhV1). We are currently extending these studies and anticipate finding a significant incidence of infection in humans world wide particularly among those humans who work with horses. The improved diagnostic methods outlined above, perhaps also the vaccine, are expected to have application in human medicine.

What is claimed is:

1. An isolated amino acid sequence comprising the amino acid sequence of SEQ ID NO:2.

2. The isolated amino acid sequence of claim 1, wherein the amino acid sequence consists of the amino acid sequence of SEQ ID NO:2.

3. An isolated protein or virus-like particle incorporating VP1, derived from ERhV1, and comprising the amino acid sequence of SEQ ID NO:3.

4. The isolated protein or virus-like particle of claim 3, wherein the amino acid sequence consists of the amino acid sequence of SEQ ID NO:3.

5. An isolated protein or virus-like particle incorporating VP2, derived from ERhV1, and comprising the amino acid sequence of SEQ ID NO:4.

6. The isolated protein or virus-like particle of claim 5, wherein the amino acid sequence consists of the amino acid sequence of SEQ ID NO:4.

7. An isolated protein or virus-like particle incorporating VP3, derived from ERhV1, and comprising the amino acid sequence of SEQ ID NO:5.

8. The isolated protein or virus-like particle of claim 7, wherein the amino acid sequence consists of the amino acid sequence of SEQ ID NO:5.

9. An isolated protein or virus-like particle incorporating VP4, derived from ERhV1, and comprising the amino acid sequence of SEQ ID NO:6.

10. The isolated protein or virus-like particle of claim 9, wherein the amino acid sequence consists of the amino acid sequence of SEQ ID NO:6.

* * * * *